US006451581B1

United States Patent
Falco et al.

(10) Patent No.: US 6,451,581 B1
(45) Date of Patent: Sep. 17, 2002

(54) PLANT BRANCHED-CHAIN AMINO ACID BIOSYNTHETIC ENZYMES

(75) Inventors: Saverio Carl Falco, Arden; Rebecca E. Cahoon, Greenville; William D. Hitz, Wilmington; Anthony J. Kinney, Wilmington; J. Antoni Rafalski, Wilmington, all of DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 09/173,300

(22) Filed: Oct. 15, 1998

Related U.S. Application Data

(60) Provisional application No. 60/063,423, filed on Oct. 28, 1997.

(51) Int. Cl.[7] ............................. C12N 1/20; C12N 9/88; C12N 15/00; C07H 21/04; A01H 1/00
(52) U.S. Cl. ................... 435/252.3; 536/23.2; 435/232; 435/320.1; 435/948; 435/255.1; 435/419; 435/468; 530/350; 800/278; 800/295
(58) Field of Search ........................... 435/252.3, 320.1, 435/232, 948, 468, 419, 255.1; 536/23.2; 530/350; 800/278, 295

(56) References Cited

FOREIGN PATENT DOCUMENTS

WO          WO 94/08020          4/1994

OTHER PUBLICATIONS

Sequence alignment of SEQ ID No : 1–6 and known sequences from the database.*
NCBI General Identifier No. 400054 (Accession No. Q02139) Dec. 15, 1998.
NCBI General Identifier No. 1170543 (Accession No. P39522) Oct. 01, 1996.
NCBI General Identifier No. 1176947 (Accession No. P39576) Jul. 15, 1998.
NCBI General Identifier No. 1708468 (Accession No. Q10399) Jul. 15, 1998.
NCBI General Identifier No. 3122287 (Accession No. Q58414) Jul. 15, 1998.
NCBI General Identifier No. 124380 (Accession No. P00510) Jul. 15, 1998.
NCBI General Identifier No. 3219823 (Accession No. P81291) Jul. 15, 1998.
NCBI General Identifier No. 3122347 (Accession No. Q58409) Jul. 15, 1998.
NCBI General Identifier No. 3122345 (Accession No. Q58673) Jul. 15, 1998.
NCBI General Identifier No. 400187 (Accession No. Q02144) Dec. 15, 1998.
Higgins, D.G. and Sharp, P.M. (1989) Cabrios 5:151–153.
Hein, J.J. (1990) Meth.Enz. 183:626–645.
Selkov et al. (1997) Gene 197:GC11–GC26.
Pirrung et al, Mechanism and stereochemistry of αβ–dihydroxyacid dehydratase, *J. Am. Chem. Soc.*, 113, 1020–1025, 1991.
Kanamori et al, Studies in valine biosynthesis, *The Journal of Biological Chemistry*, 238, No. 3, 998–1005, Mar. 1963.
Flint et al, Dihydroxy acid dehyratase from spinach contains a [2Fe–eS] cluster, *The Journal of Biological Chemistry*, 263, No. 8, 3558–3564, 1988.
Wallsgrove et al, Biochemical characterisation of *nicotiana plumbaginifolia* auxotrophs that require branched–chain amino acids, *Plant Cell Reports*, 3, 223–226, 1986.
Wallsgrove et al, Biochemical characterisation of an auxotroph of *Datura innoxia* requiring isoleucine and valine, *Plant Science*, 43, 109–114, 1986.
Mazur et al, Isolation and characterization of plant genes coding for acetolactate synthase, the target enzyme for two classes of herbicides, *Plant Physiology*, 85, 1110–1117, 1987.
Dumas et al, Isolation, characterization and sequence analysis of a full–length cDNA clone encoding acetohydroxy acid reductoisomerase from spinach chloroplasts, *The Biochemical Journal*, 227, No. 2, 469–475, 1991.
Velasco et al, Cloning of the dihydroxydehydratase–encoding gene (ILV3) from *Saccaromyces cerevisiae, Gene*, 137, No. 2, 179–185, 1993.
Godon et al, Branched–chain amino acid biosynthesis genes in *Lactococcus lactis* subsp. *lactis, Journal of Bacteriology*, 174, No. 20, 6580–6589, 1992.
Lawther et al, The complete nucleotide sequence of the ilvGMEDA operon of *Escherichia coli* K–12, *Nucleic Acid Research*, 15, No. 5, 2137–2155, 1987.

* cited by examiner

*Primary Examiner*—Ponnathapu Achutamurthy
*Assistant Examiner*—Tekchand Saidha

(57) ABSTRACT

This invention relates to an isolated nucleic acid fragment encoding a branched-chain biosynthetic enzyme. The invention also relates to the construction of a chimeric gene encoding all or a portion of the branched-chain biosynthetic enzyme, in sense or antisense orientation, wherein expression of the chimeric gene results in production of altered levels of the branched-chain biosynthetic enzyme in a transformed host cell.

12 Claims, 16 Drawing Sheets

Figure 1:
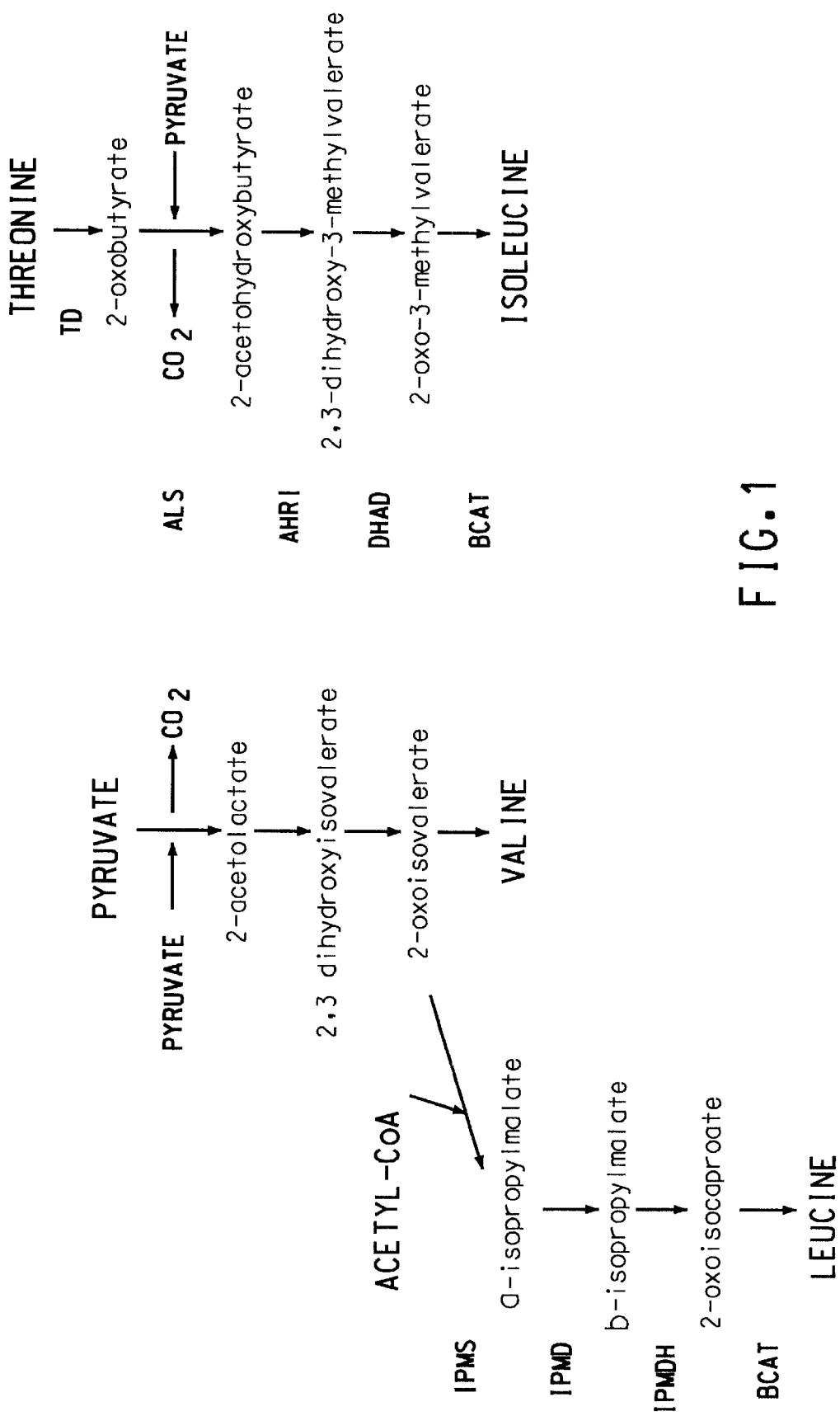

```
                       +      *           +    *   +++++++  *  +++++++++
SEQ ID NO:7    M.............GLLTKVATSRQFSTTRCVAK............KLNKYSYIITEPKGQG
SEQ ID NO:2    MQSM.......ALTSPSLPEVGPVSGRRLQRIRAT....AVSDELKLNKYSARITEPKSQG
SEQ ID NO:4    MQSTLFNPTHSLIPTSPHSIRSNSGHASLSVRASIAVETPTETVKLNKYSSRITEPKSQG
SEQ ID NO:6    ............................................................
               1                                                          60

++++++++*+++++++++   +   +++++++++++++++   *   +++  *++++   *+*+++
SEQ ID NO:7    ASQAMLYATGFKKEDEKKPQVGVGSCWWSGNPCNMHLLDLNRRCSQSIEKAGLKAMQFNT
SEQ ID NO:2    ASQAVLYGVGLTDADLRKPQVGVSSVWYEGNTCNMHLLRLAEAVRDGVREAGMVGFRFNT
SEQ ID NO:4    ASQAVLYGVGLSEDDMAKPQVGVSSVWYEGNTCNMHLLHLSEAVRDGVAAAGMVPFRFNT
SEQ ID NO:6    ............................................................
               61                                                        120

*+*     +++++++++++++++*+*   ++   +   +++++++++++++  *  ++++ 
SEQ ID NO:7    IGVSDGISMGTKGMRYSLQSREIIADSFETIMMAQHYDANIAIPSCDKNMPGVMMAMGRH
SEQ ID NO:2    VGVSDAISMGTRGMCYSLQSRDLIADSIETVMGAQHYDANISIPGCDKNMPGTIMAMGRL
SEQ ID NO:4    VGVSDAISMGTRGMCYSLQSRDLIADSIETVMAAQWYDGNISIPGCDKNMPGTIIAMGRL
SEQ ID NO:6    ............................................................
               121                                                       180

+++++++ ++++++++*   ++++++++*+++++++   *   *  *   + ** +++
SEQ ID NO:7    NRPSIMVYGGTILPGHPTCGSSKISKNIDIVSAFQSYGEYISKQFTEEEREDVVEHACPG
SEQ ID NO:2    NRPSIMIYGGTIKPGHFQ......GNSYDIVSAFQCYGEYVSGSITDEQRKNVLRNSCPG
SEQ ID NO:4    NRPSIMVYGGTIKPGHFE......GNTFDIVSAFQCYGEYVSGSINDDQRQNVIRNSCPG
SEQ ID NO:6    ............................................................
               181                                                       240
```

FIG. 2A

```
                 *+*+++++++++++++*+        +*****+++++++      ++******+++     +++*****+
SEQ ID NO:7    PGSCGGMYTANTMASAAEVLGLTIPNSSSFPAVSKEKLAECDNIGEYIKKTMELGILPRD
SEQ ID NO:2    AGACGGMYTANTMASAIETLGMSLPYSSSTPAEDPLKIEECRLAGKYLLELLKMDLKPKD
SEQ ID NO:4    AGACGGMYTANTMASAIEAMGMSLPYSSSTPAEDPLKLDECRLAGKYLLELLKMDLKPRD
SEQ ID NO:6    ...........................................................
               241                                                       300

+*+ *++*+++++++++++++++ +*+      +*+++++++  * *+++++++
SEQ ID NO:7    IILTKEAFENAITYVVATGGSTNAVLHLVAVAHSAGVKLSPDDFQRISDTTPLIGDFKPSG
SEQ ID NO:2    IITEKSLRNAMVIVMALGGSTNAVLHLIAIARSVGLHLTLDDFQKVSDQVPFLADLKPSG
SEQ ID NO:4    IITRKSLRNAMVIVMALGGSTNAVLHLIAIAKSVGIDLTLDDFQKVSDEVPFIADLKPSG
SEQ ID NO:6    ...........................................................
               301                                                       360

++++++   *+****+++*+  +++*****++++++++++++++  +*++  +++*
SEQ ID NO:7    KYVMADLINVGGTQSVIKYLYENNMLHGNTMTVTGDTLAERAKKAPSLPEGQEIIKPLSH
SEQ ID NO:2    KYVMEDLHKIGGTPAVIHYLLEQGLLDGDCMTVTGKTLAENAKIFPPLSEGQQIIRPLDN
SEQ ID NO:4    KYVMEDVHKIGGTPAVIRYLLEQGFLDGDCMTVTGKTLAENAELVPPLSNGQEIIRPVEN
SEQ ID NO:6    ...........................................................
               361                                                       420
```

FIG. 2B

```
                    +++  * +*+++++++ ++   +*++++++  +*++++++ ++*  ** *  ****
SEQ ID NO:7         PIKANGHLQILYGSLAPGGAVGKITGKEGTYFKGRARVFEEEGAFIEALERGEIKKGEKT
SEQ ID NO:2         PIKPTGHIQILYGNLAPEGSVAKITGKEGLFFSGPALVFEGEESMITAISENPANFKGK.
SEQ ID NO:4         PIKKTAHIQILYGNLAPQGSVAKITGKEGLYFSGPALVFEGEEAMIAAISEDPSSFKGK.
SEQ ID NO:6         ........APEGSVAKITGKEGLFFSGPALVFDGEESMITAISENPANFKGK.
                                                                              480

+++++ *+++++* +++++++++++++ +++*+++++++++++  +++++++ ++++
SEQ ID NO:7         VVVIRYEGPRGAPGMPEMLKPSSALMGYGLGKDVALLTDGRFSGGSHGFLIGHIVPEAAE
SEQ ID NO:2         VVVIRGEGPKGGPGMPEMLTPTSAIMGAGLGKECALLTDGRFSGGSHGFVVGHICPEAQE
SEQ ID NO:4         VVVIRGEGPKGGPGMPEMLTPTSAIMGAGLGKEVALLTDGRFSGGSHGFVVGHICPEAQE
wk05c12A.pro        VVVIRGEGPKGGPGMPEMLTPTSAIMGAGLGKECALLTDGRFSGGSHGFVVGHVCPEAQE
                                                                              540
                                    +  +                    *  *+        ++ ++
SEQ ID NO:7         GGPIGLVRDGDEIIIDADNNKIDLLVSDKEMAQRKQSWVAPPPRYTRGTLSKYAKLVSNA
SEQ ID NO:2         GGPIGLVHSGDVITIDVITIDVSKRVIDVDLTEQQLEERRKWTPPPYKSTCGALWKYIKLVAPA
SEQ ID NO:4         GGPIGLIQNGDVINVDIKNRRIDVLVSDEEMEARRKKWTAPPYKANRGALYKYIKNVTPA
SEQ ID NO:6         GGPIGLVENGDTITIDVGKKVIDVDLTEDQLEQRRRKWSPPPHKXTNGS..........
                                                                              600
                    + +++*  *
SEQ ID NO:7         SNGCVLDA
SEQ ID NO:2         SRGCVTDE
SEQ ID NO:4         SSGCVTDE
SEQ ID NO:6         ....TLE
                    601   608
```

FIG. 2C

```
                                +
SEQ ID NO:20    MTKQTIRVEL.......................................................
SEQ ID NO:09    MEYGAVLAAAPLVARPNWLLLSPPPL..APSIQIQNRLVSISSFPLK........AGPVRA
SEQ ID NO:11    ..............................................................
SEQ ID NO:13    MESIRLIYPICPSRHSSFLLSHQSPFLCEPSLSLKLR......KQFPLTSQNVLEAASPLRP
SEQ ID NO:15    ..............................................................
SEQ ID NO:17    MT..ASYNT.....................................................
SEQ ID NO:19    ..............................................................
                1                                                             60

*           *         *    ++ *++ +++ *** *     *   *
SEQ ID NO:20    ..............................................................
SEQ ID NO:09    CRALASN.YTQTSETVDLDWENLGFIVQTDYMYIAKCGTDGNFSEGEMVPFGPIALSPS..
SEQ ID NO:11    ..............................................................
SEQ ID NO:13    ..............................................................
SEQ ID NO:15    ..........................................HEGILSR...YGNIELSPS
SEQ ID NO:17    SATLSSDPYSETIELADIEWDNLGFGLQPTDYMYIMKCTRGGTFSKGELQRFGNIELNPS
SEQ ID NO:19    ........GTPDLVDFDWETLGFQLVPTDFMYIMKCSSDGVFTKGELVPYGPIELNPA
                61                                                            120

+  *+++++* +++       +           *+   *  ++  *  + +* +    +
SEQ ID NO:20    AMVYHYGQTVFEGLKAY..VSEDDHVLLFRPEKNMERLNQSNDRLCIPQIDEEQVLEGLK
SEQ ID NO:09    SGVLNYGQGLFEGLKAYK..KTDGSILLFRPEENAERMRTGAERM...............
SEQ ID NO:11    ..............................................................
SEQ ID NO:13    ..............................................................
SEQ ID NO:15    SGVINYGQGLFEGLKAYRAANQQGSYMLFRPEENARRMQHGAERMCMPSPSVEQFVHAVK
SEQ ID NO:17    AGVLNYGQLFEGLKAYR..KQDGSILLFRPEENGLRMQIGAERMCMPSPTMEQFVEAVK
SEQ ID NO:19    AAVLNYGQLLEGLRAHR..KEDGSVVVFRPKENALRMRIGADRLCMPAPSVEQFLSAVK
                121                                                           180
```

FIG. 3A

```
                  *   ***  *****  *  *** **  ++++++   ++ +  ++       +*  + *+  + *
SEQ ID NO:20  QLVAIDKDWIPNAEGTSLYIRPFIIATEPFLGVAASHTYKLLIILSPVGSYKEGIKPVK
SEQ ID NO:09  .........................................................
SEQ ID NO:11  ...................................SSFFFFFVSPVGNYFKEGLSPIN
SEQ ID NO:13  ...QTVLANRRWPPQGKGALYIRPLLIGSGPILGLAPAPEYTFLIYAAPVGTYFKEGLAPIN
SEQ ID NO:15  ...DTVLANKRWVPAGKGSLYIRPLLMGSGPVLGVAPAPEYTFLIYSPVGNYFKEGLAPIN
SEQ ID NO:17  ...HTILANKRWVPPTGKGSLYIRPLLIGSGAMLGVAPAPEYTFVVYVCPVGHYFKDGLSPIS
SEQ ID NO:19                                                                    240
              181

+    ***  *****          +    ++     +++    ** ++ +
SEQ ID NO:20  IAVESEFVRAVKGGTGNAKTAGNYASSLKAQQVAEEKGFSQVLWLDGIEKKYIEEVGSMN
SEQ ID NO:09  ............................................................
SEQ ID NO:11  LIVEDKFHRASPGTGGVKTIGNYASVLKAQKIAKGKGYSDVLYLDAVHDKYLEEVSSCN
SEQ ID NO:13  ..VVKGGVATPDTRGTILPGITRGTILPGITRKSVIELARDRGYKVEERLVSIDDLVAA
SEQ ID NO:15  LVVEDSIHRAMPGGTGGVKTITNYAPVLKAQMDAKSIGFTDVLYLDAVHKTYLEEASSCN
SEQ ID NO:17  LIVENEFHRATPGGTGA...........................................
SEQ ID NO:19  LLTEEEYHRAAPGTGDIKTIGNYASVVSAQRRAKEKGHSDVLYLDPVHKKFVEEVSSCN
              241                                                           300

*   **  ++ ++++++++*+ ++  ++  *  +   *   +    +*+
SEQ ID NO:20  IFFKINGEIVTPMLNGSILEGITRNSVIALLKHWGLQVSERKIAIDEVIQAHKDGILEEA.......
SEQ ID NO:09  .IFVVKDNVISTPAIKGTILPGITRKSIIEVAQSKGFKVEERLVCVDELINA........DEV
SEQ ID NO:11  .IFVVKDNVISTPAIKGTILPGITRKSIIEVAQSKGFKVEERLVCVDELINA........DEV
SEQ ID NO:13  ..VVKGGVATPDTRGTILPGITRKSVIELARDRGYKVEERLVSIDDLVAA..........DEV
SEQ ID NO:15  .LFIVKDGVVATPATVGTILPGITRKSVIELARDRGYQVEERLVSIDDLVGA........DEV
SEQ ID NO:17  ...............................................................
SEQ ID NO:19  ILMVKDNVISTPLLTGTILPGITRRSIIEIAQNLGIQVEERLIAIDELLDA.........DEV
              301                                                           360
```

FIG. 3B

```
                +*++++*+  ++         *            *  *              +  +  *  +  +**   *         +++
SEQ ID NO:20    FGTGTAAVISPVGELIWQDETLSINNGETGEIAKKLYDTITGIQKGAVADE.FGWTTEVA
SEQ ID NO:09    ........................................................
SEQ ID NO:11    FCTGTAVVVSPVGSVTYMGKRVEYGNQGVGVVSQQLYKSLTSLQMGNV.EDWMGWTMQLN
SEQ ID NO:13    FCTGTAVVVAPVSTVTYQGERYEF.RTGPDTVSQELYTTLTSIQMGMAAEDSXGWTVPVE
SEQ ID NO:15    FCTGTAVVVAPVSSVTYHGQRYEF.RTGHDTLSQTLHTLTSIQMGLA.EDKKGWTV...
SEQ ID NO:17    ........................................................
SEQ ID NO:19    FCTGTAVVLSPVGSIVYHGRRVEYGGGKVGAVSQQLYSALTAIQKGLV.EDSMGWSVQLN
                361                                                      420

SEQ ID NO:20    ALTESK
SEQ ID NO:09    ......
SEQ ID NO:11    ..Q...
SEQ ID NO:13    XIN..K
SEQ ID NO:15    AID...
SEQ ID NO:17    .....R
SEQ ID NO:19    ......
                421  426
```

FIG. 3C

```
                           *+***  +****+*++*+**+*+**+*****+*******+*  +*++  +*++
SEQ ID NO:29      MKIYLNGKFVDEKDAKVSVFDHGLLY.GDGVFEGIRAYDGVVFMLKEHIDRLYDSAKSLC
SEQ ID NO:22      .........................................................A.RVQPKAR
SEQ ID NO:24      ..........HEAMVIPMDDHMVHRGHGVEDTAAIMDGYLYELDQHLDRFLRSASMSK
SEQ ID NO:26      ..........MYSSIYGGIILDPAMMVIPIDDHMVHRGHGVEDTAIVLDGYLYELDVHLDRFLSSASKAK
SEQ ID NO:28      ..........................................................
                  1                                                          60

+ +*  *  +**+  +*+*  +*    *   ++  ++          +     *    +
SEQ ID NO:29      IDIPLTKEEMIDVVLETLRVNNLRDAYIRLVTRGVGDLGLDPRKCGKPTIFCIAIPMPP
SEQ ID NO:22      IGTPFPRDTLRSILVQMTAASNCRGSIRYWLSAGGGDFLLSSAGCAGPAFYAVVIPTDY
SEQ ID NO:24      IDPPFDRGSIRRILIQTVSASKCRKGSLRYWLSAGPGDFQLSPSCCHRSSLYAIVIQDLS
SEQ ID NO:26      ISSPFSRSVLHSILIQLTAASKCKKGTLRYWLSAGPGDFLLSSAGCPTSAFYAVVIDQDV
SEQ ID NO:28      ..................................TRLSSSGCTNPALYAVVIESPS
                  61                                                         120

*  *   * *     +  +*  *++++ **  *+        *    ** +  *+
SEQ ID NO:29      LLGEDGIRAITVSVRRLPVDV.LNPAVKSLNYLNSVLAKIQANYAGVDEAFLLDDKGFVV
SEQ ID NO:22      SQCRH...GVRAVTTSVPMKPPLFATMKNVNYLPNVLSIMDAEDRGAFASVWVDGEGNVA
SEQ ID NO:24      PSSPN.FRGVKVVTSSIPIKHPKFAITKSVNYLPNVLSKVEAEEAGAFVGIWLDGEGFVA
SEQ ID NO:26      SQCKE....GVKVITSNIPMKPSLFATAKNVNYLPNVLSVMEAEEKGASSSIWVDEEGYIA
SEQ ID NO:28      LQVPS...CCRVVTSSIPIKSPQFAVMKSVNYLPNALTKVEGEENGAFTGIWLDDEGFVA
                  121                                                        180
```

FIG. 4A

```
                        +          +*    *          ++  * ++  *+++*  *         *     *
SEQ ID NO:29            EGTGDNI.FIVKNGVLKTPPVYQSILKGITRDVIKLAKEEGIEVVEEPLTLHDLYT...
SEQ ID NO:22            EGPMVNVAFVTAAGELVLPA.FDKILAGCTAKRLLALAPRLVESGLLKAVTTRHIAADEA
SEQ ID NO:24            EGPNMNVAFVTKDKELIMPH.FDKILSGCTAKRVLTLAESLLREGKLKGIRVKTVTVEEG
SEQ ID NO:26            EGPNVNVAFITQDKELVMPP.FDNILHGCTAKRLLELAPKLVDQGLLKGVATKKLTVEEA
SEQ ID NO:28            EGSNMNVGFVTKNKELLMPR.FDKILSGCTARRVLTLAEHLVAHGKLSRVISRNVSVEEG
                        181                                                      240

* +    + *   **   +*  +      +           * ** + *** **
SEQ ID NO:29            ...ADELFITGTAAEIVPVFEIDGRVINNKQVGEITKKLKEKFKDIR.....TKWGIKVY
SEQ ID NO:22            KRCSAEMAFVGSGLPVLPIVEWDDQLIGDGKVGKTMALSDLLWEDMKSGP..DRIAVPY
SEQ ID NO:24            KQ.ADEMMLLGSGVLVCPVVQWDEQVIGDGKEGPITQALLNLIVEDMKSGPSTVRIPVPY
SEQ ID NO:26            KA.AAEMMYVGSTLPLLPIIVWDDQPIGNGRVGELTMLLSDMLWDDMVAGPGTQRIPVPY
SEQ ID NO:28            KM.ADEMMLIGSGILVKPVVQWDDKIIGSGQEGPIAQA..................
                        241                                                      300

SEQ ID NO:29            .DE
SEQ ID NO:22            .K.
SEQ ID NO:24            ...
SEQ ID NO:26            VE.
SEQ ID NO:28            ...
                        301 303
```

FIG. 4B

```
SEQ ID NO:34   ................MTTKKADYIWFNGEMVRWEDAKVHVMSHALHYGTSVFEGIRCYDSHKGPV
SEQ ID NO:31   QPPLSDPPLPVPANKNILVWVGDELLPRNSAKVSVFDSVVQGGDAVWEGLRIYDGK.....
SEQ ID NO:33   ...................................A......R................
               1                                                           60

++**  ++++++ ++  +++++ *++++++ ******  ++++++ ******* +**+*+***
SEQ ID NO:34   VFRHREHMQRLHDSAKIYRFPVSQSIDELMEAC.RDVIRKNNLTSAYIR.PLIFVGDVGM
SEQ ID NO:31   VFKLDEHLDRLFDSAKAMAFSNVPTRDWIKDAIFKTLIANGMFNNAHIRLTLTRGKKVTS
SEQ ID NO:33   V.KLEEHLDRLFDSTKAMAFSNVPSRDWIKDAIFKTLNANGMFNNAHIRLTLTRGKKVTS
               61                                                         120

+  +  *  *+++*   * *+ +++ +   *++++++*+      ++*++*++   *+ *
SEQ ID NO:34   GVNPPAG.YSTDVIIAAFPWGAYLGAEALEQGIDAMVSSWNRAAPNTIPTAAKAGGNYLS
SEQ ID NO:31   GMSPAFNLYGCALIVLA.EWKPPVYDNS..HGIKLVTATTRRNSPNSIDPKIHHN.NLIN
SEQ ID NO:33   GMSPTFNLYGCVLIVLA.EWKPPVYDNS..HGIKLVTAATRRNSPNSVDSKIHHN.NLIN
               121                                                        180

*+*+++*+**   *+**+*+ +++++** +++ ++  * *+++*++++ ***+++++++*
SEQ ID NO:34   SLLVGSEARRHGYQEGIALDVNGYISEGAGENLFEVKDGVLFTPPFTSSALPGITRDAII
SEQ ID NO:31   NILAKIEGNLAQAEDAIMLDKDGFVSETNATNIFMVKKGIVLTPH.ADYCLPGITRATVM
SEQ ID NO:33   NILAKIEGNLAQAEDAIMLDQDGFVSETNATNIFMVKKGIVLTPH.ADYCLPGITRATVK
               181                                                        240
```

FIG. 5A

```
                   *+******* *+*+**++**+++++++++++***+*+++++*+ ++*+++
SEQ ID NO:34      KLAKELGIEVREQVLSRESLYLADEVFMSGTAAEITPVRSVDGIQVGEGRCGPVTKRIQQ
SEQ ID NO:31      DLVVKENFVLHERRISLSEFHAADEVWTTGTMGEITPVVMIDGREIGDGKIGPVTRQIQK
SEQ ID NO:33      DLVVKENLVLHERRISLSEFHAADEVWTTGTMGEITPVVMIDGREIGDKIGLVTRQIQS
                  241                                                          300

+*** +*** *** ** **
SEQ ID NO:34      AFFGLFTGETEDKWGWLDQVNQ
SEQ ID NO:31      AYKILTAGQGVPIPG..VAEV.
SEQ ID NO:33      AYKVLTAGLGVTIPR..NAEA.
                  301                 322
```

FIG. 5B

```
                   +  ++    +++++  ++      *    ++++*+   ++++ *+    *+*+*+++++++*  ++++++*++
SEQ ID NO:45       MGMTIVEKILAKASGKKEVSPGDIVMANIDVAMVHDITGPLTVNTLK.EYGIE.KVWNPE
SEQ ID NO:36       ..........AREPGENVWVDIDVLMTHDVCGPGTIGIFKKEFGEDAKVWDRE
SEQ ID NO:38       MTMT..EKILARASERAALEPGENVWVDVDVLMTHDVCGPGAFDIFKKEFGEDARVWDRE
SEQ ID NO:40       ............................................................
SEQ ID NO:42       ............................................................
SEQ ID NO:44       ............................................................
                   1                                                          60

+*+  *****+****     *+  ++*+++++++++*****+++*+       *     +*
SEQ ID NO:45       KIVILEDHQVPADSIKAAENHILMRKFVKEQGIKYFYDIRE.........GVCHQVLP
SEQ ID NO:36       KVVIIPDHYIFTSDERANRNVDILRDFCLEQNIKYFYDIKDLSDFRANPDYKGVCHIALA
SEQ ID NO:38       KLVVIPDHYIFTSDGRAKRNVDILRDFCAEQNIKYFYDIKDLSDFRANPDYKGVCHIALA
SEQ ID NO:40       ........................................................VCHVALA
SEQ ID NO:42       ............................................................
SEQ ID NO:44       ............................................................
                   61                                                         120

**  +*+++++++++++ ++  + *+++++++++++++*  *+++++++++  *  +*+
SEQ ID NO:45       EKGHVAPGEVVVGADSHTCTHGAFGAFATGIGSTDMAHVFATGKLWFKVPETIYFNITGD
SEQ ID NO:36       QEGHCRPGEVLLGTDSHTCNAGAFGQFATGIGNTDAGFVMGTGKALLKVPPTIRFVLDGE
SEQ ID NO:38       QEAHCRPGEVLLGTDSHTCNAGAFGQFATGIGNTDAGFVMGTGKALLKVPPTIRFILDGE
SEQ ID NO:40       QEGHCRPGEVLLGTDSHTCNAGAFGQFATGIGNTDAGFVMGTGKALLKVPPTIRFVLDGE
SEQ ID NO:42       ............................................................
SEQ ID NO:44       ............................................................
                   121                                                        180
```

FIG. 6A

```
                   *++*+++*+++*+++++++++++++++ ** * ** ** *+**+*+**+*+**+**+*
SEQ ID NO:45  LQPYVTSKDVILSITGEVGVDGATYKACQFGGETVKKMSIASRMTMTNMAIEMGGKTGII
SEQ ID NO:36  MPPYLLAKDLILQIIGEISVSGATYKSMEFVGSTVESLTMEERMTLCNMVEAGGKNGVV
SEQ ID NO:38  MPPYLLAKDLILQIIGEISVSGATYKSMEFVGSTVESLTMEERMTLCNMVIEAGGKNGVV
SEQ ID NO:40  MPPYLLAKDLILQIIGEISVSGATYKSMEFVGSTVESLNMEXRMTLCNMVIEAGGKNGVV
SEQ ID NO:42  ............................................................
SEQ ID NO:44  ............................................................
              181                                                          240

*+++*+*+*+**          +* * ***** +      *  ***+**+++**++*
SEQ ID NO:45  EPDEKTIQYVKEAMKKHGTERPFEVIKGDEDAEFAEVYEIEADKIEPVFACPHNVDNVKQ
SEQ ID NO:36  PADETTFKYLEGR......TSVDYQPVYSDAEARFFSDYRFDVSKLEPVVAKPHSPDNRAL
SEQ ID NO:38  PADETTFKYLEGK......TSVDYEPVYSDAQARFFSDYRFDVSKLEPVVAKPHSPDNRAP
SEQ ID NO:40  ..........LEGK......TSLPYEPVYSDDQARFLAEYRFDVSKLEPVVAKPHSPDNRAL
SEQ ID NO:42  ............................................................
SEQ ID NO:44  ............................................................
              241                                                          300

+++*+****+***+++++++ *******+++ *++ *+*+****+ *+***** ***
SEQ ID NO:45  AREVAGKPIDQVFIGSCTNGRLEDLRMAIKIIEKHGGIADDVRVVTPASREEYLKALKE.
SEQ ID NO:36  ARECKDVKIDRVYIGSCTGGKTEDFLAAAKVFLA.SGKKVKVPTFLVPATQKVWMDVYSL
SEQ ID NO:38  ARECKDVKIDRVYIGSCTGGKTEDFLAAAKVFLA.SGKKVKVPTFLVPATQKVWLDIYSL
SEQ ID NO:40  ARECKDVKIDRVYIGSCTGGKTEDFMAAAKVFLA.SGKQVKVPTFLVXATQKVWMDLYSL
SEQ ID NO:42  ............................................................
SEQ ID NO:44  ..................FIAAAKVFLA.SGKKVKVPTFLVPATQKVWMDVYSL
              301                                                          360
```

FIG. 6B

```
                    * *  ************* *** ++  ********* *+  *************
SEQ ID NO:45        GI.........IEKFLKYGC-VVTNPSCSACMGS...LYGVLGPGEVCVSTSNRNFRGRQG
SEQ ID NO:36        PVPGSGGKTCAQIFEEAGCDTPASPNCGACLGGPRDTYARMNEPTVCVSTTNRNFPGRMG
SEQ ID NO:38        PVPGSGGKTCSQIFEEAGCDTPASPNCGACLGGPRDTYARMNEPTVCVSTTNRNFPGRMG
SEQ ID NO:40        ............................................................
SEQ ID NO:42        PVPGSGGKTCSQIFEEVGCDTPASPSCGACLGGPKDTYARMNEPKVCVSTTNRNFPGRMG
SEQ ID NO:44        PVPGSGGKTCSQIFEEAGCDTPASPNCGACLGGPRDTYARMNEPTVCVSTTNRNFPGRMG
                    361                                                      420

* * * ++++++ * +++ * +  +++
SEQ ID NO:45        SLEAEIYLASPITAAACAVKGELVDPRDL..
SEQ ID NO:36        HKEGQIYLASPYTAAASALTGYVTDPRDFLM
SEQ ID NO:38        HKEGQIYLASPYTAAASALTGYVTDPKDFLM
SEQ ID NO:40        ...............................
SEQ ID NO:42        HKEGQIYLASPYTAAASALTGYVTDPREFL.
SEQ ID NO:44        HKEGQIYLASPFTAAASALTGYVTDPRDFLS
                    421                         452
```

FIG. 6C

```
                        +       *       *       *        *        *       *
SEQ ID NO:54    MEKFTIYKGTSVP...........................................................
SEQ ID NO:47    M..AAALSGTAVS......TAALLAPIRAPTSAFIRRSQLTCHRL.......HSLKCRR
SEQ ID NO:49    M..AAAAAPALSLAE.AAPVTAVLAPCPTPSRTFRRRSWVAAICR......PALKCHH
SEQ ID NO:51    MRKXTEVREEALSIQQWPCTRFSSAATVLPRNLAFTKLSLSHSHTLLPRFLSFPTPKSSN
SEQ ID NO:53    ........ARAAVS......TAALLAPIRAPTSAFIRRSQLTCHRL......HSLKCRR
                1                                                         60

*       *       ++++++++++++++ *+++++++++*+*+++  +
SEQ ID NO:54    ..................................VMNDNIDTDQIIPKQFLKAIDKK..GFGK
SEQ ID NO:47    A...GSIVPAAAAAAAGSSSPPSSAVFHGECFVVGDNIDTDQIIPAEHLTLVPSKPDEYRK
SEQ ID NO:49    SRPLTAVVAAAAAAAGDSTSAGVFHGECFVVGDNIDTDQIIPAEHLTLVPSKPDEYRK
SEQ ID NO:51    PRNRVAVSLQTPRAQSAASASPSASPSSSPPSSAVFHGLCYVVGDNIDTDQIIPAEYLTLVPSKPDEYEK
SEQ ID NO:53    A...GSIVPAAAAAAAGSSSPPSSAVFHGECFVVGDNIDTDQIIPAEHLTLVPSKPDEYRK
                61                                                       120

*** *  *+*   *  *   +  * ***  ** ++++++++++++*++++* + *++*   *+ *+
SEQ ID NO:54    NLFYEWRYLKDYDENPDFILNAPKYKKASLLISGDNFGSGSSREHAAWALSDYGFRAIIA
SEQ ID NO:47    LGSFAFAGLPSAAYPTPFVAPGEESSRYAIIVGGANFGCGSSREHAPVALGAAGARAIVA
SEQ ID NO:49    LGSFAFVGLPTAAYPTPFVAPGEETTRYAVIIGGANFGCGSSREHAPVALGAAGARAVVA
SEQ ID NO:51    LGSYALIGLP.ATYATRFIEPGEIKTKYAIVIGGANFGCGSSREHAPVALGASGAAAVVA
SEQ ID NO:53    LGSFAFAGLPSAAYPTPFVAPGEESSRYAIIVGGANFGCGSSREHAPVALGAAGARAIVA
                121                                                      180
```

FIG. 7A

```
                *  +*+*+*++**+  *+*++*+                *******+      +*** ** * **
SEQ ID NO:54    GSYSDIFYNNALKNG..LLPIKQPREVLNQLTKLSSQEEITIDLPHQLIITSLGDEHFEID
SEQ ID NO:47    EGYARIFFRNSVATGEVYPLELTDVGAWKECK..TGDVVTVDLANSVFINHTSGKEYKLK
SEQ ID NO:49    EGYARIFFRNSVATGEVYPLELADTGAWKECK..TGDVVTVELDNCVMINHTSGKQYKLK
SEQ ID NO:51    ESYARIFFRNSVATGEVYPLE.SEGRLCEECT..TGDVVTIELGESRLINHTTGKEYRLK
SEQ ID NO:53    EGYARIFFRNSVGTGEVYPLELTDVGAWKECK..TGDVVTVDLANSVFINHTSGKEYKLK
                181                                                       240

+++*+*       ****+*+*+*+***+******  *
SEQ ID NO:54    PIWKDKLINGLDDIGITLQYEEAISAYEQKN..Q
SEQ ID NO:47    PIGDA...GPVIEAGGIFAYARKTGMIASKAAA.
SEQ ID NO:49    PIGDA...GPVIEAGGIFAYARKTGMIASKSA..
SEQ ID NO:51    PIGDA...GPVIEAGGIFAYARKTGMIPSR....
SEQ ID NO:53    PIGDA...GPVIEAGGIFAYARKTGMIASKAAA.
                241                              274
```

FIG. 7B

SEQUENCE LISTING

<160> NUMBER OF SEQ ID NOS: 54

<210> SEQ ID NO 1
<211> LENGTH: 2135
<212> TYPE: DNA
<213> ORGANISM: Zea mays

<400> SEQUENCE: 1

```
cacagctcca cttgtccctg tccatccatt catcattccc cgtcactcca ccaattcacc      60
acccaaaacc ctaaacccca ttccgtacct caacgccgcc gccgccgccg ccgccgctgc     120
gatgcagtcc atggcgctca cctccccctc actcccggag gtcggccccg tttccggccg     180
ccgtctccag cgcatccgtg ccaccgcggt atccgacgag ctcaagctga acaagtacag     240
cgcgcgcatc acggagccca agtcgcaggg cgcctcgcag gccgtgctct atggggtcgg     300
gctcactgac gctgacctcc gcaagccgca ggtcggcgtc tcgtcggtgt ggtacgaggg     360
gaacacctgc aacatgcacc tgctccgcct cgcggaggcc gtccgtgacg gcgtccgcga     420
ggccggcatg gtcggcttcc ggtttaacac cgtcggtgtc agcgacgcca tttccatggg     480 caccegggge atgtgctaca gcctccagtc ccgtgacctc atcgccgaca gcatcgagac     540
cgtcatggga gcgcagcact acgacgccaa catttccata cctgggtgcg acaagaacat     600
gccaggtaca ataatggcaa tgggacggct taatcgacct agcataatga tatatggtgg     660
aactattaag cctggtcact ttcagggcaa ttcctatgat atagtatctg ctttccagtg     720
ctatggagaa tatgttagtg gttcaatcac tgatgagcaa agaaagaacg tcctccgcaa     780
ttcatgtcca ggagcaggtg cctgtggtgg tatgtacaca gcaaacacta tggcatctgc     840
tatcgaaact ttgggcatga gtcttccata cagttcttcg acacctgctg aggacccact     900
aaaactagaa gagtgccgtc ttgctgggaa gtatctttta gagttgctaa agatggattt     960
gaagcctaag gacattatca ctgagaagtc attgcgaaat gcaatggtta ttgttatggc    1020
acttggtggt tcgactaatg ctgttctgca tttgattgcc attgctcggt ccgttggttt    1080
```

```
gcatttgact cttgatgatt tccagaaggt cagtgaccaa gttcctttcc ttgcagacct      1140
caagcccagt ggcaaatatg tcatggagga tctacataag attggtggga cacctgcagt      1200
cattcattac cttttggagc aaggtcttct tgatggtgat tgcatgactg ttactggtaa      1260
aactctagct gagaatgcta aaatcttccc tcctctgtct gagggcagc aaataattcg       1320 accacttgac aatcctatca aaccaactgg ccatattcaa atactttatg gaaatcttgc      1380
accggaaggt tctgtcgcaa aaataactgg caaagaggga ctgttcttct caggtcccgc      1440
attagttttt gagggtgaag aatccatgat cacagctatc tcagaaaacc cagcgaattt      1500
caagggaaag gtagtagtaa tccgaggaga aggaccaaaa ggagggccag ggatgcctga      1560
aatgttgact ccaacaagtg caataatggg tgctggtctc ggaaaggagt gcgccctgct      1620
gacagatggt agattttcag gaggctcaca tggatttgtt gtcggccaca tatgccctga      1680
agcacaggaa ggtggcccga ttggccttgt ccatagtggt gatgtaatca ccatcgatgt      1740
aagtaagagg gtaatcgacg ttgaccttac cgagcagcag ctcgaagaaa gacggaggaa      1800 atggaccccca ccgccataca agtccacctg tggagctctt tggaagtaca tcaagcttgt      1860
ggctccagcg tctagaggat gcgtcactga tgagtaggat gtgttacatt ctgttaggtt      1920
gtgcacatga tgtgtttgtc aatcaaaagc tgttgccagg aacaatttcc ctgttagagt      1980
gattcattgt agttcggttt tgcatgtggc aggtatgaca ataaattgcc ggtttctaag      2040
agcttagcaa tgctgcagaa actgctgaat aatcgagtgt aatcggggtc cgtgagcaat      2100
cacatctttg tcagtcaaaa aaaaaaaaaa aaaaa                                 2135

<210> SEQ ID NO 2
<211> LENGTH: 591
<212> TYPE: PRT
<213> ORGANISM: Zea mays

<400> SEQUENCE: 2

Met Gln Ser Met Ala Leu Thr Ser Pro Ser Leu Pro Glu Val Gly Pro
 1               5                  10                  15

Val Ser Gly Arg Arg Leu Gln Arg Ile Arg Ala Thr Ala Val Ser Asp
            20                  25                  30

Glu Leu Lys Leu Asn Lys Tyr Ser Ala Arg Ile Thr Glu Pro Lys Ser
        35                  40                  45

Gln Gly Ala Ser Gln Ala Val Leu Tyr Gly Val Gly Leu Thr Asp Ala
    50                  55                  60

Asp Leu Arg Lys Pro Gln Val Gly Val Ser Ser Val Trp Tyr Glu Gly
65                  70                  75                  80

Asn Thr Cys Asn Met His Leu Leu Arg Leu Ala Glu Ala Val Arg Asp
                85                  90                  95

Gly Val Arg Glu Ala Gly Met Val Gly Phe Arg Phe Asn Thr Val Gly
            100                 105                 110

Val Ser Asp Ala Ile Ser Met Gly Thr Arg Gly Met Cys Tyr Ser Leu
        115                 120                 125

Gln Ser Arg Asp Leu Ile Ala Asp Ser Ile Glu Thr Val Met Gly Ala
    130                 135                 140

Gln His Tyr Asp Ala Asn Ile Ser Ile Pro Gly Cys Asp Lys Asn Met
145                 150                 155                 160

Pro Gly Thr Ile Met Ala Met Gly Arg Leu Asn Arg Pro Ser Ile Met
                165                 170                 175

Ile Tyr Gly Gly Thr Ile Lys Pro Gly His Phe Gln Gly Asn Ser Tyr
```

```
            180             185             190
Asp Ile Val Ser Ala Phe Gln Cys Tyr Gly Glu Tyr Val Ser Gly Ser
            195             200             205

Ile Thr Asp Glu Gln Arg Lys Asn Val Leu Arg Asn Ser Cys Pro Gly
210             215             220

Ala Gly Ala Cys Gly Gly Met Tyr Thr Ala Asn Thr Met Ala Ser Ala
225             230             235             240

Ile Glu Thr Leu Gly Met Ser Leu Pro Tyr Ser Ser Thr Pro Ala
            245             250             255

Glu Asp Pro Leu Lys Leu Glu Cys Arg Leu Ala Gly Lys Tyr Leu
            260             265             270

Leu Glu Leu Leu Lys Met Asp Leu Lys Pro Lys Asp Ile Ile Thr Glu
            275             280             285

Lys Ser Leu Arg Asn Ala Met Val Ile Val Met Ala Leu Gly Gly Ser
290             295             300

Thr Asn Ala Val Leu His Leu Ile Ala Ile Ala Arg Ser Val Gly Leu
305             310             315             320

His Leu Thr Leu Asp Asp Phe Gln Lys Val Ser Asp Gln Val Pro Phe
            325             330             335

Leu Ala Asp Leu Lys Pro Ser Gly Lys Tyr Val Met Glu Asp Leu His
            340             345             350

Lys Ile Gly Gly Thr Pro Ala Val Ile His Tyr Leu Leu Glu Gln Gly
            355             360             365

Leu Leu Asp Gly Asp Cys Met Thr Val Thr Gly Lys Thr Leu Ala Glu
            370             375             380

Asn Ala Lys Ile Phe Pro Pro Leu Ser Glu Gly Gln Gln Ile Ile Arg
385             390             395             400

Pro Leu Asp Asn Pro Ile Lys Pro Thr Gly His Ile Gln Ile Leu Tyr
            405             410             415

Gly Asn Leu Ala Pro Glu Gly Ser Val Ala Lys Ile Thr Gly Lys Glu
            420             425             430

Gly Leu Phe Phe Ser Gly Pro Ala Leu Val Phe Glu Gly Glu Glu Ser
            435             440             445

Met Ile Thr Ala Ile Ser Glu Asn Pro Ala Asn Phe Lys Gly Lys Val
450             455             460

Val Val Ile Arg Gly Glu Gly Pro Lys Gly Gly Pro Gly Met Pro Glu
465             470             475             480

Met Leu Thr Pro Thr Ser Ala Ile Met Gly Ala Gly Leu Gly Lys Glu
            485             490             495

Cys Ala Leu Leu Thr Asp Gly Arg Phe Ser Gly Ser His Gly Phe
            500             505             510

Val Val Gly His Ile Cys Pro Glu Ala Gln Glu Gly Gly Pro Ile Gly
            515             520             525

Leu Val His Ser Gly Asp Val Ile Thr Ile Asp Val Ser Lys Arg Val
            530             535             540

Ile Asp Val Asp Leu Thr Glu Gln Gln Leu Glu Arg Arg Lys
545             550             555             560

Trp Thr Pro Pro Tyr Lys Ser Thr Cys Gly Ala Leu Trp Lys Tyr
            565             570             575

Ile Lys Leu Val Ala Pro Ala Ser Arg Gly Cys Val Thr Asp Glu
            580             585             590

<210> SEQ ID NO 3
```

<211> LENGTH: 2073
<212> TYPE: DNA
<213> ORGANISM: Glycine max

<400> SEQUENCE: 3

```
gtaaacccttt tttccatcta gagttgttgc ggctctcttc tctgcacact cagaatgcag      60
tccacactct tcaaccccac ccattccctt atccccactt caccacactc tatcagatcc     120
aattctggtc atgcttctct ctccgttcgc gcctccatcg ccgtggaaac ccccacggag     180
acggtgaagc tgaacaagta cagctcccgc atcaccgagc ccaaatcgca gggcgcctcc     240
caggccgtgc tctacggcgt cggtctctcc gaggacgaca tggccaagcc ccaggtcggc     300
gtctcctcgg tctggtacga gggcaacacc tgcaacatgc acctcctcca cctctccgag     360
gccgtgcgtg acggcgttgc tgctgctggc atggttccct tccgcttcaa caccgttggc     420
gtcagcgacg ccatctccat gggcacccgt ggcatgtgct acagcctcca gtccagggac     480
ctcattgccg acagcatcga gaccgtcatg gcagcgcagt ggtacgatgg caatatttcc     540
atccccggct gtgacaaaaa tatgccaggt actatcattg ccatggggag gctcaacaga     600
cctagcatta tggtttatgg cgggactata aaacctggtc attttgaggg taacacgttt     660
gacatagtgt ctgcctttca gtgctatgga gaatatgtga gtggatcaat taatgatgac     720
caaagacaaa atgttattcg caactcatgc cctggggctg gagcctgtgg tggaatgtat     780
acagccaata ccatggcttc tgcaatagaa gctatgggaa tgtctcttcc ctatagctca     840
tctacacctg ctgaggatcc actaaagttg gatgagtgtc gtttagctgg gaaatatctt     900
cttgagttac tgaaaatgga cttgaagccc cgagatatca tcactcgtaa atcactacgt     960
aatgcaatgg ttatagttat ggcacttggt ggatctacta atgctgtgtt acatttaatt    1020
gctattgcca gtctgttgg cattgatttg actcttgatg attttcagaa ggttagcgat    1080
gaggttcctt ttattgcaga tcttaagcct agtgggaaat atgtcatgga agatgttcac    1140
aagattggag ggactcctgc agttatccgc taccttcttg agcaaggctt tttagatggt    1200
gactgtatga ctgtcactgg aaaaacccta gctgaaaatg cagaacttgt ccctcctctg    1260
tccaacgggc aggaaataat aaggccagta gaaaatccca tcaagaagac ggctcacatt    1320
caaatattat atgaaaacct tgcaccacag ggttccgttg ctaaaattac tggaaaagaa    1380
gggctgtact tctctggtcc tgcacttgtc tttgaaggag aggaggcaat gattgctgcc    1440
atttcagagg atccttcgag ttttaagggg aaagtggttg taatcagggg agagggaccc    1500
aagggtggtc cgggaatgcc tgagatgtta acaccaacaa gtgcaataat gggtgcaggt    1560
cttgaaaagg aagttgcatt attgactgat ggaagatttt caggaggttc acatggattt    1620
gtggttggcc atatatgtcc tgaagcacag gaaggtggtc caattggctt gattcaaaat    1680
ggagacgtaa tcaatgttga catcaagaat aggagaattg atgttttggt atcagatgag    1740
gagatggaag cacgcaggaa aaagtggact gctcctccat acaaagctaa ccgaggagct    1800
ctgtacaagt atattaaaaa tgtgacacct gcttctagtg gatgcgtaac agacgagtag    1860
aaagacatac ctgcagagca aaagctgata gtatgccttg gtgaaatttt gtcttgtgtt    1920
tccagaacaa gttggtaaaa attcaaaaac aaacctcatt tcagagaatt taaacaatg    1980
gaattgaatt gctactattg attagtgact atttaatatt tatgattttc tagagctaaa    2040
aaaaaaaaaa aaaaaaaaa aaaaaaaaaa aaa                                   2073
```

<210> SEQ ID NO 4
<211> LENGTH: 601

```
<212> TYPE: PRT
<213> ORGANISM: Glycine max

<400> SEQUENCE: 4

Met Gln Ser Thr Leu Phe Asn Pro Thr His Ser Leu Ile Pro Thr Ser
 1               5                  10                  15

Pro His Ser Ile Arg Ser Asn Ser Gly His Ala Ser Leu Ser Val Arg
            20                  25                  30

Ala Ser Ile Ala Val Glu Thr Pro Thr Glu Thr Val Lys Leu Asn Lys
        35                  40                  45

Tyr Ser Ser Arg Ile Thr Glu Pro Lys Ser Gln Gly Ala Ser Gln Ala
    50                  55                  60

Val Leu Tyr Gly Val Gly Leu Ser Glu Asp Met Ala Lys Pro Gln
65                  70                  75                  80

Val Gly Val Ser Ser Val Trp Tyr Gly Asn Thr Cys Asn Met His
                85                  90                  95

Leu Leu His Leu Ser Glu Ala Val Arg Asp Gly Val Ala Ala Gly
            100                 105                 110

Met Val Pro Phe Arg Phe Asn Thr Val Gly Val Ser Asp Ala Ile Ser
        115                 120                 125

Met Gly Thr Arg Gly Met Cys Tyr Ser Leu Gln Ser Arg Asp Leu Ile
    130                 135                 140

Ala Asp Ser Ile Glu Thr Val Met Ala Ala Gln Trp Tyr Asp Gly Asn
145                 150                 155                 160

Ile Ser Ile Pro Gly Cys Asp Lys Asn Met Pro Gly Thr Ile Ile Ala
                165                 170                 175

Met Gly Arg Leu Asn Arg Pro Ser Ile Met Val Tyr Gly Gly Thr Ile
            180                 185                 190

Lys Pro Gly His Phe Glu Gly Asn Thr Phe Asp Ile Val Ser Ala Phe
        195                 200                 205

Gln Cys Tyr Gly Glu Tyr Val Ser Gly Ser Ile Asn Asp Asp Gln Arg
    210                 215                 220

Gln Asn Val Ile Arg Asn Ser Cys Pro Gly Ala Gly Ala Cys Gly Gly
225                 230                 235                 240

Met Tyr Thr Ala Asn Thr Met Ala Ser Ala Ile Glu Ala Met Gly Met
                245                 250                 255

Ser Leu Pro Tyr Ser Ser Thr Pro Ala Glu Asp Pro Leu Lys Leu
            260                 265                 270

Asp Glu Cys Arg Leu Ala Gly Lys Tyr Leu Leu Glu Leu Leu Lys Met
        275                 280                 285

Asp Leu Lys Pro Arg Asp Ile Ile Thr Arg Lys Ser Leu Arg Asn Ala
    290                 295                 300

Met Val Ile Val Met Ala Leu Gly Gly Ser Thr Asn Ala Val Leu His
305                 310                 315                 320

Leu Ile Ala Ile Ala Lys Ser Val Gly Ile Asp Leu Thr Leu Asp Asp
                325                 330                 335

Phe Gln Lys Val Ser Asp Glu Val Pro Phe Ile Ala Asp Leu Lys Pro
            340                 345                 350

Ser Gly Lys Tyr Val Met Glu Asp Val His Lys Ile Gly Gly Thr Pro
        355                 360                 365

Ala Val Ile Arg Tyr Leu Leu Glu Gln Gly Phe Leu Asp Gly Asp Cys
    370                 375                 380

Met Thr Val Thr Gly Lys Thr Leu Ala Glu Asn Ala Glu Leu Val Pro
385                 390                 395                 400
```

```
Pro Leu Ser Asn Gly Gln Glu Ile Ile Arg Pro Val Glu Asn Pro Ile
            405                 410                 415

Lys Lys Thr Ala His Ile Gln Ile Leu Tyr Gly Asn Leu Ala Pro Gln
        420                 425                 430

Gly Ser Val Ala Lys Ile Thr Gly Lys Glu Gly Leu Tyr Phe Ser Gly
        435                 440                 445

Pro Ala Leu Val Phe Glu Gly Glu Ala Met Ile Ala Ala Ile Ser
        450                 455                 460

Glu Asp Pro Ser Ser Phe Lys Gly Lys Val Val Ile Arg Gly Glu
465                 470                 475                 480

Gly Pro Lys Gly Gly Pro Gly Met Pro Glu Met Leu Thr Pro Thr Ser
                485                 490                 495

Ala Ile Met Gly Ala Gly Leu Gly Lys Glu Val Ala Leu Leu Thr Asp
            500                 505                 510

Gly Arg Phe Ser Gly Ser His Gly Phe Val Val Gly His Ile Cys
        515                 520                 525

Pro Glu Ala Gln Glu Gly Gly Pro Ile Gly Leu Ile Gln Asn Gly Asp
        530                 535                 540

Val Ile Asn Val Asp Ile Lys Asn Arg Arg Ile Asp Val Leu Val Ser
545                 550                 555                 560

Asp Glu Glu Met Glu Ala Arg Arg Lys Lys Trp Thr Ala Pro Pro Tyr
                565                 570                 575

Lys Ala Asn Arg Gly Ala Leu Tyr Lys Tyr Ile Lys Asn Val Thr Pro
            580                 585                 590

Ala Ser Ser Gly Cys Val Thr Asp Glu
        595                 600

<210> SEQ ID NO 5
<211> LENGTH: 517
<212> TYPE: DNA
<213> ORGANISM: Triticum aestivum
<220> FEATURE:
<221> NAME/KEY: unsure
<222> LOCATION: (447)

<400> SEQUENCE: 5
tgcaccagaa ggttcagtag caaaaataac cggcaaggag ggactgtttt tctcaggtcc      60
tgcactagtt tttgacggtg aagaatcaat gattacagct atatcagaaa acccagcaaa     120
tttcaaggga aggttgtag tgatccgagg agaaggacca aaaggaggtc ccgggatgcc      180
tgaaatgttg actccaacaa gtgcaataat ggggctggt cttgggaagg agtgtgccct      240
gctgacagat ggtagatttt ctgggggtc gcatggattt gttgtgggcc acgtatgtcc      300
tgaagcacag gaaggaggcc caattggtct tgttgagaat ggcgatacaa tcacgatcga     360
cgtcgggaag aaagtaattg atgttgattt gacggaagac cagcttgaac aaaggcgaag     420
gaaatggagc ccgcctccac acaaggntac taatgggagc actttggaag tacataaagc     480
tccgtgtcct tcagcctcaa agtggggtgc gtcaacc                              517

<210> SEQ ID NO 6
<211> LENGTH: 156
<212> TYPE: PRT
<213> ORGANISM: Triticum aestivum
<220> FEATURE:
<221> NAME/KEY: UNSURE
<222> LOCATION: (149)

<400> SEQUENCE: 6
```

```
Ala Pro Glu Gly Ser Val Ala Lys Ile Thr Gly Lys Glu Gly Leu Phe
 1               5                  10                  15

Phe Ser Gly Pro Ala Leu Val Phe Asp Gly Glu Glu Ser Met Ile Thr
             20                  25                  30

Ala Ile Ser Glu Asn Pro Ala Asn Phe Lys Gly Lys Val Val Val Ile
             35                  40                  45

Arg Gly Glu Gly Pro Lys Gly Gly Pro Gly Met Pro Glu Met Leu Thr
         50                  55                  60

Pro Thr Ser Ala Ile Met Gly Ala Gly Leu Gly Lys Glu Cys Ala Leu
 65                  70                  75                  80

Leu Thr Asp Gly Arg Phe Ser Gly Ser His Gly Phe Val Val Gly
                 85                  90                  95

His Val Cys Pro Glu Ala Gln Glu Gly Gly Pro Ile Gly Leu Val Glu
                100                 105                 110

Asn Gly Asp Thr Ile Thr Ile Asp Val Gly Lys Lys Val Ile Asp Val
                115                 120                 125

Asp Leu Thr Glu Asp Gln Leu Glu Gln Arg Arg Lys Trp Ser Pro
        130                 135                 140

Pro Pro His Lys Xaa Thr Asn Gly Ser Thr Leu Glu
145                 150                 155

<210> SEQ ID NO 7
<211> LENGTH: 585
<212> TYPE: PRT
<213> ORGANISM: Saccharomyces cerevisiae

<400> SEQUENCE: 7

Met Gly Leu Leu Thr Lys Val Ala Thr Ser Arg Gln Phe Ser Thr Thr
 1               5                  10                  15

Arg Cys Val Ala Lys Lys Leu Asn Lys Tyr Ser Tyr Ile Ile Thr Glu
             20                  25                  30

Pro Lys Gly Gln Gly Ala Ser Gln Ala Met Leu Tyr Ala Thr Gly Phe
         35                  40                  45

Lys Lys Glu Asp Phe Lys Lys Pro Gln Val Gly Val Gly Ser Cys Trp
     50                  55                  60

Trp Ser Gly Asn Pro Cys Asn Met His Leu Leu Asp Leu Asn Asn Arg
 65                  70                  75                  80

Cys Ser Gln Ser Ile Glu Lys Ala Gly Leu Lys Ala Met Gln Phe Asn
                 85                  90                  95

Thr Ile Gly Val Ser Asp Gly Ile Ser Met Gly Thr Lys Gly Met Arg
                100                 105                 110

Tyr Ser Leu Gln Ser Arg Glu Ile Ile Ala Asp Ser Phe Glu Thr Ile
                115                 120                 125

Met Met Ala Gln His Tyr Asp Ala Asn Ile Ala Ile Pro Ser Cys Asp
        130                 135                 140

Lys Asn Met Pro Gly Val Met Met Ala Met Gly Arg His Asn Arg Pro
145                 150                 155                 160

Ser Ile Met Val Tyr Gly Gly Thr Ile Leu Pro Gly His Pro Thr Cys
                165                 170                 175

Gly Ser Ser Lys Ile Ser Lys Asn Ile Asp Ile Val Ser Ala Phe Gln
                180                 185                 190

Ser Tyr Gly Glu Tyr Ile Ser Lys Gln Phe Thr Glu Glu Arg Glu
            195                 200                 205

Asp Val Val Glu His Ala Cys Pro Gly Pro Gly Ser Cys Gly Gly Met
```

```
            210                 215                 220
Tyr Thr Ala Asn Thr Met Ala Ser Ala Ala Glu Val Leu Gly Leu Thr
225                 230                 235                 240

Ile Pro Asn Ser Ser Ser Phe Pro Ala Val Ser Lys Glu Lys Leu Ala
                245                 250                 255

Glu Cys Asp Asn Ile Gly Glu Tyr Ile Lys Lys Thr Met Glu Leu Gly
                260                 265                 270

Ile Leu Pro Arg Asp Ile Leu Thr Lys Glu Ala Phe Glu Asn Ala Ile
                275                 280                 285

Thr Tyr Val Val Ala Thr Gly Ser Thr Asn Ala Val Leu His Leu
290                 295                 300

Val Ala Val Ala His Ser Ala Gly Val Lys Leu Ser Pro Asp Phe
305                 310                 315                 320

Gln Arg Ile Ser Asp Thr Thr Pro Leu Ile Gly Asp Phe Lys Pro Ser
                325                 330                 335

Gly Lys Tyr Val Met Ala Asp Leu Ile Asn Val Gly Gly Thr Gln Ser
                340                 345                 350

Val Ile Lys Tyr Leu Tyr Glu Asn Asn Met Leu His Gly Asn Thr Met
                355                 360                 365

Thr Val Thr Gly Asp Thr Leu Ala Glu Arg Ala Lys Lys Ala Pro Ser
370                 375                 380

Leu Pro Glu Gly Gln Glu Ile Ile Lys Pro Leu Ser His Pro Ile Lys
385                 390                 395                 400

Ala Asn Gly His Leu Gln Ile Leu Tyr Gly Ser Leu Ala Pro Gly Gly
                405                 410                 415

Ala Val Gly Lys Ile Thr Gly Lys Glu Gly Thr Tyr Phe Lys Gly Arg
                420                 425                 430

Ala Arg Val Phe Glu Glu Gly Ala Phe Ile Glu Ala Leu Glu Arg
                435                 440                 445

Gly Glu Ile Lys Lys Gly Glu Lys Thr Val Val Ile Arg Tyr Glu
450                 455                 460

Gly Pro Arg Gly Ala Pro Gly Met Pro Glu Met Leu Lys Pro Ser Ser
465                 470                 475                 480

Ala Leu Met Gly Tyr Gly Leu Gly Lys Asp Val Ala Leu Leu Thr Asp
                485                 490                 495

Gly Arg Phe Ser Gly Gly Ser His Gly Phe Leu Ile Gly His Ile Val
                500                 505                 510

Pro Glu Ala Ala Glu Gly Gly Pro Ile Gly Leu Val Arg Asp Gly Asp
                515                 520                 525

Glu Ile Ile Ile Asp Ala Asp Asn Asn Lys Ile Asp Leu Leu Val Ser
                530                 535                 540

Asp Lys Glu Met Ala Gln Arg Lys Gln Ser Trp Val Ala Pro Pro Pro
545                 550                 555                 560

Arg Tyr Thr Arg Gly Thr Leu Ser Lys Tyr Ala Lys Leu Val Ser Asn
                565                 570                 575

Ala Ser Asn Gly Cys Val Leu Asp Ala
                580                 585

<210> SEQ ID NO 8
<211> LENGTH: 502
<212> TYPE: DNA
<213> ORGANISM: Zea mays

<400> SEQUENCE: 8
```

```
cgctgagcaa ccccggcct acacggcgta gctttgcagg aaatggaata cggcgccgtc      60
ctcgccgccg cgccgctcgt cgcacggccg aactggctcc tcctctcgcc gccgccactg    120
gcgccgtcta ttcagattca gaatcgtctt tattcgatct cgtcattccc actaaaggct    180
ggacctgtaa gggcatgcag agctttagca agcaactaca cgcaaacatc tgaaacagtt    240
gatttggact gggagaacct gggttttggg attgtgcaaa ctgattatat gtatattgct    300
aagtgcggga cagacgggaa ttttctgag ggtgaaatgg tgccttttgg acctatagcg     360
ctgagtccat cttctggagt cctaaattat ggacagggat tgtttgaggg cctaaaggcg    420
tataagaaaa ctgatggatc catcctatta tttcgcccag aggaaaatgc tgagaggatg    480
cggacaggtg ctgagaggat gt                                             502
```

<210> SEQ ID NO 9
<211> LENGTH: 153
<212> TYPE: PRT
<213> ORGANISM: Zea mays

<400> SEQUENCE: 9

```
Met Glu Tyr Gly Ala Val Leu Ala Ala Ala Pro Leu Val Ala Arg Pro
  1               5                  10                  15
Asn Trp Leu Leu Leu Ser Pro Pro Leu Ala Pro Ser Ile Gln Ile
             20                  25                  30
Gln Asn Arg Leu Tyr Ser Ile Ser Ser Phe Pro Leu Lys Ala Gly Pro
         35                  40                  45
Val Arg Ala Cys Arg Ala Leu Ala Ser Asn Tyr Thr Gln Thr Ser Glu
     50                  55                  60
Thr Val Asp Leu Asp Trp Glu Asn Leu Gly Phe Gly Ile Val Gln Thr
 65                  70                  75                  80
Asp Tyr Met Tyr Ile Ala Lys Cys Gly Thr Asp Gly Asn Phe Ser Glu
                 85                  90                  95
Gly Glu Met Val Pro Phe Gly Pro Ile Ala Leu Ser Pro Ser Ser Gly
                100                 105                 110
Val Leu Asn Tyr Gly Gln Gly Leu Phe Glu Gly Leu Lys Ala Tyr Lys
            115                 120                 125
Lys Thr Asp Gly Ser Ile Leu Leu Phe Arg Pro Glu Glu Asn Ala Glu
        130                 135                 140
Arg Met Arg Thr Gly Ala Glu Arg Met
145                 150
```

<210> SEQ ID NO 10
<211> LENGTH: 794
<212> TYPE: DNA
<213> ORGANISM: Zea mays

<400> SEQUENCE: 10

```
tcgagttttt ttttttttt ttttgtatcc cctgttggga attatttcaa ggaaggttta     60
tctcctatta atttgatcgt tgaggataaa tttcaccgtg ccagccctgg tggaactgga    120
ggtgtgaaaa ccattggaaa ctatgcctcg gtactgaaag cacaaaagat tgcaaagggg    180
aaaggatatt ctgatgtcct ttatttggat gctgttcatg acaaatatct tgaagaagtc    240
tcttcctgca atattttgt tgtgaaagac aatgttattt ctacgcctgc cattaaagga    300
acaatacttc tggtataac gaggaaaagt atcattgaag ttgctcagag caaaggtttc    360
aaggttgagg agcgtctggt gtgtgtagat gagttgatta cgctgatga agttttctgc    420
acggggactg ctgttgtggt gtcacctgtg gggagtgtta catatatggg gaaaaggggtg    480
```

```
gaatatggca accaaggagt cggtgtcgtg tctcagcaac tatacaagtc acttacaagc    540
ctccagatgg gcaatgtgga ggactggatg ggttggacca tgcaacttaa tcagtagcgg    600
atcacagata ttgccttggc agatcccgga ttattacagc tactgggtgc gatagttttt    660
tttttggcag atccatcttg agcatatttg actgtaccgg tttcccttga gactaagacg    720
aaagtgatct tactgatctt ttgtttcaaa tctaaaacga taaataaaa tgtggtttgc     780 aaaaaaaaaa aaaa                                                       794
```

```
<210> SEQ ID NO 11
<211> LENGTH: 198
<212> TYPE: PRT
<213> ORGANISM: Zea mays

<400> SEQUENCE: 11
```

| | | | | | | | | | | | | | | |
|---|---|---|---|---|---|---|---|---|---|---|---|---|---|---|
| Ser | Ser | Phe | Phe | Phe | Phe | Phe | Phe | Val | Ser | Pro | Val | Gly | Asn | Tyr | Phe |
| 1 | | | | 5 | | | | | 10 | | | | | 15 | |

Lys Glu Gly Leu Ser Pro Ile Asn Leu Ile Val Glu Asp Lys Phe His
            20                  25                  30

Arg Ala Ser Pro Gly Gly Thr Gly Gly Val Lys Thr Ile Gly Asn Tyr
        35                  40                  45

Ala Ser Val Leu Lys Ala Gln Lys Ile Ala Lys Gly Lys Gly Tyr Ser
 50                  55                  60

Asp Val Leu Tyr Leu Asp Ala Val His Asp Lys Tyr Leu Glu Glu Val
65                  70                  75                  80

Ser Ser Cys Asn Ile Phe Val Val Lys Asp Asn Val Ile Ser Thr Pro
                85                  90                  95

Ala Ile Lys Gly Thr Ile Leu Pro Gly Ile Thr Arg Lys Ser Ile Ile
            100                 105                 110

Glu Val Ala Gln Ser Lys Gly Phe Lys Val Glu Glu Arg Leu Val Cys
        115                 120                 125

Val Asp Glu Leu Ile Asn Ala Asp Glu Val Phe Cys Thr Gly Thr Ala
130                 135                 140

Val Val Val Ser Pro Val Gly Ser Val Thr Tyr Met Gly Lys Arg Val
145                 150                 155                 160

Glu Tyr Gly Asn Gln Gly Val Gly Val Ser Gln Gln Leu Tyr Lys
                165                 170                 175

Ser Leu Thr Ser Leu Gln Met Gly Asn Val Glu Asp Trp Met Gly Trp
            180                 185                 190

Thr Met Gln Leu Asn Gln
        195

```
<210> SEQ ID NO 12
<211> LENGTH: 445
<212> TYPE: DNA
<213> ORGANISM: Zea mays
<220> FEATURE:
<221> NAME/KEY: unsure
<222> LOCATION: (252)
<220> FEATURE:
<221> NAME/KEY: unsure
<222> LOCATION: (311)
<220> FEATURE:
<221> NAME/KEY: unsure
<222> LOCATION: (336)
<220> FEATURE:
<221> NAME/KEY: unsure
<222> LOCATION: (356)
<220> FEATURE:
<221> NAME/KEY: unsure
```

```
<222> LOCATION: (361)
<220> FEATURE:
<221> NAME/KEY: unsure
<222> LOCATION: (369)
<220> FEATURE:
<221> NAME/KEY: unsure
<222> LOCATION: (384)
<220> FEATURE:
<221> NAME/KEY: unsure
<222> LOCATION: (393)
<220> FEATURE:
<221> NAME/KEY: unsure
<222> LOCATION: (418)
<220> FEATURE:
<221> NAME/KEY: unsure
<222> LOCATION: (431)
<220> FEATURE:
<221> NAME/KEY: unsure
<222> LOCATION: (437)

<400> SEQUENCE: 12
gtcgtcaagg gcggcgtggt cgccacgccg acacccggg gcaccatcct gccgggcatc      60
acgcgcaaga gcgtcatcga gctcgccagg gaccgcggat acaaggttga ggaacgcctg    120
gtttccatcg acgatctggt ggccgcagac gaggtgttct gcaccgggac cgcggtggtg    180
gttgctcccg tgtcgacagt cacgtaccag ggcgagaggt atgagttcag aacggggccg    240
gacacggtgt cncaggagct gtacacgacg ctgacatcca ttcagatggg catggccgcc    300
gaggacagca ngggatggac agtaccagta gagtanatta ataaggttgg ggaatncatc    360
nccacaacnt tgtttccaca tcantattgt canccggtaa aatgcatact cggttatnac    420
atatgtgtgt ngcacanttg aaaaa                                         445

<210> SEQ ID NO 13
<211> LENGTH: 115
<212> TYPE: PRT
<213> ORGANISM: Zea mays
<220> FEATURE:
<221> NAME/KEY: UNSURE
<222> LOCATION: (104)
<220> FEATURE:
<221> NAME/KEY: UNSURE
<222> LOCATION: (112)

<400> SEQUENCE: 13

Val Val Lys Gly Gly Val Val Ala Thr Pro Asp Thr Arg Gly Thr Ile
  1               5                  10                  15

Leu Pro Gly Ile Thr Arg Lys Ser Val Ile Glu Leu Ala Arg Asp Arg
             20                  25                  30

Gly Tyr Lys Val Glu Glu Arg Leu Val Ser Ile Asp Asp Leu Val Ala
         35                  40                  45

Ala Asp Glu Val Phe Cys Thr Gly Thr Ala Val Val Ala Pro Val
     50                  55                  60

Ser Thr Val Thr Tyr Gln Gly Glu Arg Tyr Glu Phe Arg Thr Gly Pro
 65                  70                  75                  80

Asp Thr Val Ser Gln Glu Leu Tyr Thr Thr Leu Thr Ser Ile Gln Met
                 85                  90                  95

Gly Met Ala Ala Glu Asp Ser Xaa Gly Trp Thr Val Pro Val Glu Xaa
            100                 105                 110

Ile Asn Lys
        115

<210> SEQ ID NO 14
<211> LENGTH: 1086
```

-continued

```
<212> TYPE: DNA
<213> ORGANISM: Oryza sativa

<400> SEQUENCE: 14
gcacgagggc atactcagcc gctacggcaa catcgagctc agcccctcct ccggcgtcat      60
caactacggc cagggctct  tcgagggtct gaaggcgtac agggcggcga accaacaggg    120
gtcgtacatg ctgttccggc cggaggagaa cgcgcggcgg atgcagcacg cgccgagcg     180
catgtgcatg ccgtcgccgt cggtggagca gttcgtccac gccgtcaagc agaccgtcct    240
cgccaaccgc cgctgggtgc caccgcaagg aaaggggcg  ctgtacatca ggccgctgct    300
catcgggagc ggaccgattc tcgggctggc tcccgccccg gagtacacgt tcctcatcta    360
cgccgcaccg gttggaacgt acttcaagga gggtctagcg ccgataaacc ttgtcgtaga    420
ggactcgata caccgggcca tgccgggcgg caccggtggg gtcaagacga tcaccaacta    480
cgcgccggtg ctcaaggcgc agatggacgc caagagcata gggttcactg acgtgctgta    540
cctcgacgcg gtgcacaaga cgtacctgga ggaggcctcc tcctgcaacc tcttcatcgt    600
caaggacggg gtcgtcgcca cgccggccac cgtgggaacc atcctgccgg gatcacgcg     660
caagagcgtc atcgagctcg ccagggaccg cggctatcag gttgaagaac ggctcgtctc    720
catcgacgat ctggtcggcg cagacgaggt gttctgcacc ggaacagcgg tggtcgttgc    780
cccagtatcg agtgttactt accatgggca aaggtacgag ttcaggactg acatgacac     840
gttatcgcag acactgcaca cgactctgac gtccatccag atgggcctgg ctgaggacaa    900
gaaaggatgg acagtggcaa tagattaagg atggattatg ggcaaaggga tcccgattat    960
tcctcatgtc atccaatgta gattattgtc gttttatata tcttcctgta gcgacagtga   1020
tcacagcgca agtggaattt ggacgaacag gaagcaaatg cagatcatct tactgcgtaa   1080
aaaaaa                                                               1086

<210> SEQ ID NO 15
<211> LENGTH: 307
<212> TYPE: PRT
<213> ORGANISM: Oryza sativa

<400> SEQUENCE: 15

Glu Gly Ile Leu Ser Arg Tyr Gly Asn Ile Glu Leu Ser Pro Ser Ser
  1               5                  10                  15

Gly Val Ile Asn Tyr Gly Gln Gly Leu Phe Glu Gly Leu Lys Ala Tyr
             20                  25                  30

Arg Ala Ala Asn Gln Gln Gly Ser Tyr Met Leu Phe Arg Pro Glu Glu
         35                  40                  45

Asn Ala Arg Arg Met Gln His Gly Ala Glu Arg Met Cys Met Pro Ser
     50                  55                  60

Pro Ser Val Glu Gln Phe Val His Ala Val Lys Gln Thr Val Leu Ala
 65                  70                  75                  80

Asn Arg Arg Trp Val Pro Pro Gln Gly Lys Gly Ala Leu Tyr Ile Arg
                 85                  90                  95

Pro Leu Leu Ile Gly Ser Gly Pro Ile Leu Gly Leu Ala Pro Ala Pro
            100                 105                 110

Glu Tyr Thr Phe Leu Ile Tyr Ala Ala Pro Val Gly Thr Tyr Phe Lys
        115                 120                 125

Glu Gly Leu Ala Pro Ile Asn Leu Val Val Glu Asp Ser Ile His Arg
    130                 135                 140

Ala Met Pro Gly Gly Thr Gly Gly Val Lys Thr Ile Thr Asn Tyr Ala
```

| | | | | | | | | | | | | | |
|---|---|---|---|---|---|---|---|---|---|---|---|---|---|
| | | | 145 | | | | 150 | | | | 155 | | 160 |
| Pro | Val | Leu | Lys | Ala | Gln | Met | Asp | Ala | Lys | Ser | Ile | Gly | Phe | Thr | Asp |
| | | | | 165 | | | | 170 | | | | 175 | |
| Val | Leu | Tyr | Leu | Asp | Ala | Val | His | Lys | Thr | Tyr | Leu | Glu | Glu | Ala | Ser |
| | | | 180 | | | | | 185 | | | | 190 | |
| Ser | Cys | Asn | Leu | Phe | Ile | Val | Lys | Asp | Gly | Val | Ala | Thr | Pro | Ala |
| | | 195 | | | | 200 | | | | 205 | | |
| Thr | Val | Gly | Thr | Ile | Leu | Pro | Gly | Ile | Thr | Arg | Lys | Ser | Val | Ile | Glu |
| | 210 | | | | 215 | | | | 220 | | |
| Leu | Ala | Arg | Asp | Arg | Gly | Tyr | Gln | Val | Glu | Glu | Arg | Leu | Val | Ser | Ile |
| 225 | | | | 230 | | | | 235 | | | | 240 |
| Asp | Asp | Leu | Val | Gly | Ala | Asp | Glu | Val | Phe | Cys | Thr | Gly | Thr | Ala | Val |
| | | | 245 | | | | 250 | | | | 255 |
| Val | Val | Ala | Pro | Val | Ser | Ser | Val | Thr | Tyr | His | Gly | Gln | Arg | Tyr | Glu |
| | | 260 | | | | 265 | | | | 270 | |
| Phe | Arg | Thr | Gly | His | Asp | Thr | Leu | Ser | Gln | Thr | Leu | His | Thr | Thr | Leu |
| | | 275 | | | | 280 | | | | 285 | |
| Thr | Ser | Ile | Gln | Met | Gly | Leu | Ala | Glu | Asp | Lys | Lys | Gly | Trp | Thr | Val |
| | 290 | | | | 295 | | | | 300 | | |
| Ala | Ile | Asp |
| 305 |

<210> SEQ ID NO 16
<211> LENGTH: 965
<212> TYPE: DNA
<213> ORGANISM: Glycine max

<400> SEQUENCE: 16

```
catccttgtt tgtccatgct cccgagttgt gaatatcagg gactgcctca gctcctccat      60
tgactttcct tggagttgta agcccagctt agaagaggct acgctgatgt ccatttctca     120
aagtttaatt tcaactccca atatcacaag tttatataga tatatgcttt tttgaaagag     180
gctcgtgccg aattcggcac gaggaaaatg gagagcattc gactaattta cccgatctgc     240
ccctctagac attcttcctt tcttctctct catcaatctc ccttcctatg cgaaccttct     300
ctctctctca agcttcgaaa gcagtttcct ctcacttcgc agaatgttct ggaagccgcc     360
tctcctctca ggccttccgc cactctgtct tctgatccct acagtgagac gattgaatta     420
gctgatatag aatgggacaa ccttgggttt gggcttcaac ccactgatta tatgtatatc     480
atgaaatgca cacgaggtgg aaccttttcc aaaggtgaat tgcagcgttt tgggaacatc     540
gagttgaacc cctccgctgg agttttaaac tatggccagg gattatttga gggtttgaaa     600
gcataccgca acaagatgg gagtatactc ctcttccgtc cggaagaaaa tggtttgcgg     660
atgcagatag gtgcggagcg gatgtgcatg ccatcaccta ctatggagca gtttgtggaa     720
gctgtgaagg atactgtttt agctaacaaa cgttgggttc cccctgcagg taaggttcc      780
ttgtatatta gacctttgtt aatgggaagt ggacctgtac ttggtgttgc acctgcacca     840
gagtacacat ttctaatata tgtttcacct gttgggaact acttcaagga aggtttggcc     900
ccaatcaatt tgattgtaga aaatgaattc catcgtgcaa ctcctggtgg cactggagct     960
cgtgc                                                                 965
```

<210> SEQ ID NO 17
<211> LENGTH: 252
<212> TYPE: PRT
<213> ORGANISM: Glycine max

<400> SEQUENCE: 17

```
Met Glu Ser Ile Arg Leu Ile Tyr Pro Ile Cys Pro Ser Arg His Ser
  1               5                  10                  15
Ser Phe Leu Leu Ser His Gln Ser Pro Phe Leu Cys Glu Pro Ser Leu
             20                  25                  30
Ser Leu Lys Leu Arg Lys Gln Phe Pro Leu Thr Ser Gln Asn Val Leu
         35                  40                  45
Glu Ala Ala Ser Pro Leu Arg Pro Ser Ala Thr Leu Ser Ser Asp Pro
     50                  55                  60
Tyr Ser Glu Thr Ile Glu Leu Ala Asp Ile Glu Trp Asp Asn Leu Gly
 65                  70                  75                  80
Phe Gly Leu Gln Pro Thr Asp Tyr Met Tyr Ile Met Lys Cys Thr Arg
                 85                  90                  95
Gly Gly Thr Phe Ser Lys Gly Glu Leu Gln Arg Phe Gly Asn Ile Glu
            100                 105                 110
Leu Asn Pro Ser Ala Gly Val Leu Asn Tyr Gly Gln Gly Leu Phe Glu
        115                 120                 125
Gly Leu Lys Ala Tyr Arg Lys Gln Asp Gly Ser Ile Leu Leu Phe Arg
    130                 135                 140
Pro Glu Glu Asn Gly Leu Arg Met Gln Ile Gly Ala Glu Arg Met Cys
145                 150                 155                 160
Met Pro Ser Pro Thr Met Glu Gln Phe Val Glu Ala Val Lys Asp Thr
                165                 170                 175
Val Leu Ala Asn Lys Arg Trp Val Pro Pro Ala Gly Lys Gly Ser Leu
            180                 185                 190
Tyr Ile Arg Pro Leu Leu Met Gly Ser Gly Pro Val Leu Gly Val Ala
        195                 200                 205
Pro Ala Pro Glu Tyr Thr Phe Leu Ile Tyr Val Ser Pro Val Gly Asn
    210                 215                 220
Tyr Phe Lys Glu Gly Leu Ala Pro Ile Asn Leu Ile Val Glu Asn Glu
225                 230                 235                 240
Phe His Arg Ala Thr Pro Gly Gly Thr Gly Ala Arg
                245                 250
```

<210> SEQ ID NO 18
<211> LENGTH: 1501
<212> TYPE: DNA
<213> ORGANISM: Triticum aestivum

<400> SEQUENCE: 18

```
gcacgagccg cgcggcacgt cggtctcccc cagccccagg ccgcatccgg gcctaccctc    60
gcaacccatt cagaagcgat tgtccggcag cgccgtctcc gtctccaggc gaggcactgc   120
ggcaaggagc agcccgtgtt ccgccctgat gacggcatca taacacag gaactccgga    180
cctagtcgac ttcgactggg agactcttgg atttcaactg gtcccgacgg actttatgta   240
tataatgaaa tgttcgtcag atgggtgtt caccaagggt gaattggttc catatgggcc    300
aatcgagctg aaccctgctg ctgcagtttt aaattatggc cagggattgc tcgaaggtct   360
tagagcacac agaaaggagg atggttcagt agttgttttt cgccccaagg aaaacgcgtt   420
gcggatgagg ataggtgcag atcggctatg catgcctgca ccaagcgttg agcagttcct   480
atcagctgtc aagcacacta tattggcaaa caagcgttgg taccccca ctggcaaagg    540
ttctttatat atcaggccgc tgctgattgg aagtggagct atgctaggtg tagcacctgc   600
```

-continued

```
cccggagtat acatttgttg tgtatgtttg cccagttggt cactatttca aggatggcct      660
gtcaccaatt agcttattga ctgaggaaga atatcaccgc gctgcacctg gtggaactgg      720
tgatattaag acaattggaa attatgcttc ggttgttagt gctcagagaa gagccaagga      780
gaaaggtcat tctgatgttc tttacttgga tcccgtgcat aagaagtttg tggaggaagt      840
ttcttcctgt aatatattga tggtgaagga taatgttatt tctactccac tattaacggg      900
aacaattctt cctggaatca aagaagaag tataattgaa attgcccaaa atcttggaat       960
ccaggtcgaa gagcgcctta ttgcgataga tgagttgctt gacgctgatg aagtcttctg     1020
tacagggact gccgttgtac tatcacccgt tggttccatt gtgtaccacg aagaagagt      1080
ggagtatggg ggcgggaagg tcggagcggt gtcccagcaa ctgtattcgg cacttacagc    1140
tatccagaaa ggccttgtgg aggacagtat gggatggagt gtgcagttga attagcagct    1200
tcatcatctg gacggtctct acgagcctcc tcggcaagaa aacaatgcaa atcacttga    1260
ccctctgtca ggaaattttg cagaatgtag aatagcataa tttccctgtg aagatagcaa    1320
gaggtacaca cacaacatag catcaagctg gatcagaaag attaataata atgattaaat    1380
agctgttgtt tcttctcatt ctgtttccca agaggactga atgcgctttg agtgtgaata    1440
actccataac atacttgcaa ttgcaaacca tgagacataa ataattggtg caaaaaaaa    1500
a                                                                    1501
```

<210> SEQ ID NO 19
<211> LENGTH: 348
<212> TYPE: PRT
<213> ORGANISM: Triticum aestivum

<400> SEQUENCE: 19

```
Met Thr Ala Ser Tyr Asn Thr Gly Thr Pro Asp Leu Val Asp Phe Asp
  1               5                  10                  15

Trp Glu Thr Leu Gly Phe Gln Leu Val Pro Thr Asp Phe Met Tyr Ile
                 20                  25                  30

Met Lys Cys Ser Ser Asp Gly Val Phe Thr Lys Gly Glu Leu Val Pro
             35                  40                  45

Tyr Gly Pro Ile Glu Leu Asn Pro Ala Ala Ala Val Leu Asn Tyr Gly
         50                  55                  60

Gln Gly Leu Leu Glu Gly Leu Arg Ala His Arg Lys Glu Asp Gly Ser
 65                  70                  75                  80

Val Val Val Phe Arg Pro Lys Glu Asn Ala Leu Arg Met Arg Ile Gly
                 85                  90                  95

Ala Asp Arg Leu Cys Met Pro Ala Pro Ser Val Glu Gln Phe Leu Ser
            100                 105                 110

Ala Val Lys His Thr Ile Leu Ala Asn Lys Arg Trp Val Pro Pro Thr
        115                 120                 125

Gly Lys Gly Ser Leu Tyr Ile Arg Pro Leu Leu Ile Gly Ser Gly Ala
    130                 135                 140

Met Leu Gly Val Ala Pro Ala Pro Glu Tyr Thr Phe Val Val Tyr Val
145                 150                 155                 160

Cys Pro Val Gly His Tyr Phe Lys Asp Gly Leu Ser Pro Ile Ser Leu
                165                 170                 175

Leu Thr Glu Glu Glu Tyr His Arg Ala Ala Pro Gly Gly Thr Gly Asp
            180                 185                 190

Ile Lys Thr Ile Gly Asn Tyr Ala Ser Val Val Ser Ala Gln Arg Arg
        195                 200                 205
```

```
Ala Lys Glu Lys Gly His Ser Asp Val Leu Tyr Leu Asp Pro Val His
    210                 215                 220

Lys Lys Phe Val Glu Val Ser Ser Cys Asn Ile Leu Met Val Lys
225                 230                 235                 240

Asp Asn Val Ile Ser Thr Pro Leu Leu Thr Gly Thr Ile Leu Pro Gly
                245                 250                 255

Ile Thr Arg Arg Ser Ile Ile Glu Ile Ala Gln Asn Leu Gly Ile Gln
            260                 265                 270

Val Glu Glu Arg Leu Ile Ala Ile Asp Glu Leu Leu Asp Ala Asp Glu
        275                 280                 285

Val Phe Cys Thr Gly Thr Ala Val Val Leu Ser Pro Val Gly Ser Ile
    290                 295                 300

Val Tyr His Gly Arg Arg Val Glu Tyr Gly Gly Lys Val Gly Ala
305                 310                 315                 320

Val Ser Gln Gln Leu Tyr Ser Ala Leu Thr Ala Ile Gln Lys Gly Leu
                325                 330                 335

Val Glu Asp Ser Met Gly Trp Ser Val Gln Leu Asn
            340                 345
```

<210> SEQ ID NO 20
<211> LENGTH: 363
<212> TYPE: PRT
<213> ORGANISM: Bacillus subtilis

<400> SEQUENCE: 20

```
Met Thr Lys Gln Thr Ile Arg Val Glu Leu Thr Ser Thr Lys Lys Pro
1               5                   10                  15

Lys Pro Asp Pro Asn Gln Leu Ser Phe Gly Arg Val Phe Thr Asp His
                20                  25                  30

Met Phe Val Met Asp Tyr Ala Ala Asp Lys Gly Trp Tyr Asp Pro Arg
            35                  40                  45

Ile Ile Pro Tyr Gln Pro Leu Ser Met Asp Pro Thr Ala Met Val Tyr
        50                  55                  60

His Tyr Gly Gln Thr Val Phe Glu Gly Leu Lys Ala Tyr Val Ser Glu
65                  70                  75                  80

Asp Asp His Val Leu Leu Phe Arg Pro Glu Lys Asn Met Glu Arg Leu
                85                  90                  95

Asn Gln Ser Asn Asp Arg Leu Cys Ile Pro Gln Ile Asp Glu Glu Gln
            100                 105                 110

Val Leu Glu Gly Leu Lys Gln Leu Val Ala Ile Asp Lys Asp Trp Ile
        115                 120                 125

Pro Asn Ala Glu Gly Thr Ser Leu Tyr Ile Arg Pro Phe Ile Ile Ala
    130                 135                 140

Thr Glu Pro Phe Leu Gly Val Ala Ala Ser His Thr Tyr Lys Leu Leu
145                 150                 155                 160

Ile Ile Leu Ser Pro Val Gly Ser Tyr Lys Glu Gly Ile Lys Pro
                165                 170                 175

Val Lys Ile Ala Val Glu Ser Glu Phe Val Arg Ala Val Lys Gly Gly
            180                 185                 190

Thr Gly Asn Ala Lys Thr Ala Gly Asn Tyr Ala Ser Ser Leu Lys Ala
        195                 200                 205

Gln Gln Val Ala Glu Glu Lys Gly Phe Ser Gln Val Leu Trp Leu Asp
    210                 215                 220

Gly Ile Glu Lys Lys Tyr Ile Glu Glu Val Gly Ser Met Asn Ile Phe
225                 230                 235                 240
```

```
Phe Lys Ile Asn Gly Glu Ile Val Thr Pro Met Leu Asn Gly Ser Ile
                245                 250                 255

Leu Glu Gly Ile Thr Arg Asn Ser Val Ile Ala Leu Leu Lys His Trp
            260                 265                 270

Gly Leu Gln Val Ser Glu Arg Lys Ile Ala Ile Asp Glu Val Ile Gln
        275                 280                 285

Ala His Lys Asp Gly Ile Leu Glu Glu Ala Phe Gly Thr Gly Thr Ala
    290                 295                 300

Ala Val Ile Ser Pro Val Gly Glu Leu Ile Trp Gln Asp Glu Thr Leu
305                 310                 315                 320

Ser Ile Asn Asn Gly Glu Thr Gly Glu Ile Ala Lys Lys Leu Tyr Asp
                325                 330                 335

Thr Ile Thr Gly Ile Gln Lys Gly Ala Val Ala Asp Glu Phe Gly Trp
            340                 345                 350

Thr Thr Glu Val Ala Ala Leu Thr Glu Ser Lys
        355                 360

<210> SEQ ID NO 21
<211> LENGTH: 1162
<212> TYPE: DNA
<213> ORGANISM: Glycine max

<400> SEQUENCE: 21
gcacgagtac agcccaaggc ccgcatcggc accccgttcc cgcgcgacac gctccgcagc      60
atcctcgtcc agatgacggc ggcgtccaac tgccggaggg ggtccatccg ctactggctc     120
agcgccggcg gcggcgactt cctcctgtcc tccgccggct cgccgggcc ggcgttctac      180
gccgtcgtca tcccgaccga ctactcccag tgccgccacg gcgtgcgcgc ggtgaccacg     240
tcggtgccca tgaagccgcc gctgttcgcc accatgaaga acgtcaacta cctcccccaac    300
gtgctgtcca tcatggacgc cgaggaccgc ggcgcgttcg cgtcggtgtg ggtggacggc     360
gagggcaacg tcgccgaggg gcccatggta aacgtggcgt tcgtcacggc cgccggcgag    420
ctggtgctcc cggcgttcga caagatcctc gccggggtgca ccgccaagcg gctgctcgcg   480
ctggcgccga ggctggtgga gtccggcctc ctcaaggccg tcaccacccg ccacatcgcc    540
gccgacgagg ccaagcgctg ctccgccgag atggcgttcg tcggcagcgg cctccccgtc    600
ctgcccatcg tcgagtggga cgaccagctc atcggcgacg ggaaggtggg gaagacgatg    660
atggcgctgt cggatctgct ctgggaggac atgaaatcgg ggccggacag gatcgcagtc   720
ccgtacaagt gatggattat tggagttggg tgaggctcct cgggcgtacg tcagaaagag    780
gtgtgctacc gacgtgtgga ttcatgacgg taagcttcac ctgttaggga ttcacgtctc    840
ttcgacttta tatgagagga gctacgtcca tcggagatag gaggagaagg caacgtgcc     900
gagtatatat gtgtagtgta cgtacgcgtg agcgagctga gatggatatg atgcagtatc   960
gtgtcgtttc gtttcgtttc tccttgtgtt catgtgtggc ttgtatggtt ttttatctgt   1020
acgtgtcgtc aacgtaatcc ttgtattttg cggtgtatca gtactgtatg agtgtatgtg   1080
tttatcgatt gatcattaag tgaatgaata atggattctc tcgatttcaa atgtaaaaaa   1140
aaaaaaaaa aaaaaaaaaa aa                                             1162

<210> SEQ ID NO 22
<211> LENGTH: 243
<212> TYPE: PRT
<213> ORGANISM: Glycine max
```

<400> SEQUENCE: 22

| Ala | Arg | Val | Gln | Pro | Lys | Ala | Arg | Ile | Gly | Thr | Phe | Pro | Arg | Asp |
|-----|-----|-----|-----|-----|-----|-----|-----|-----|-----|-----|-----|-----|-----|-----|
| 1   |     |     |     | 5   |     |     |     |     | 10  |     |     |     |     | 15  |

| Thr | Leu | Arg | Ser | Ile | Leu | Val | Gln | Met | Thr | Ala | Ala | Ser | Asn | Cys | Arg |
|-----|-----|-----|-----|-----|-----|-----|-----|-----|-----|-----|-----|-----|-----|-----|-----|
|     |     |     | 20  |     |     |     |     | 25  |     |     |     |     | 30  |     |     |

| Arg | Gly | Ser | Ile | Arg | Tyr | Trp | Leu | Ser | Ala | Gly | Gly | Asp | Phe | Leu |
|-----|-----|-----|-----|-----|-----|-----|-----|-----|-----|-----|-----|-----|-----|-----|
|     |     | 35  |     |     |     |     | 40  |     |     |     |     | 45  |     |     |

| Leu | Ser | Ser | Ala | Gly | Cys | Ala | Gly | Pro | Ala | Phe | Tyr | Ala | Val | Val | Ile |
|-----|-----|-----|-----|-----|-----|-----|-----|-----|-----|-----|-----|-----|-----|-----|-----|
|     | 50  |     |     |     |     | 55  |     |     |     |     | 60  |     |     |     |     |

| Pro | Thr | Asp | Tyr | Ser | Gln | Cys | Arg | His | Gly | Val | Arg | Ala | Val | Thr | Thr |
|-----|-----|-----|-----|-----|-----|-----|-----|-----|-----|-----|-----|-----|-----|-----|-----|
| 65  |     |     |     |     | 70  |     |     |     |     | 75  |     |     |     |     | 80  |

| Ser | Val | Pro | Met | Lys | Pro | Pro | Leu | Phe | Ala | Thr | Met | Lys | Asn | Val | Asn |
|-----|-----|-----|-----|-----|-----|-----|-----|-----|-----|-----|-----|-----|-----|-----|-----|
|     |     |     |     | 85  |     |     |     |     | 90  |     |     |     |     | 95  |     |

| Tyr | Leu | Pro | Asn | Val | Leu | Ser | Ile | Met | Asp | Ala | Glu | Asp | Arg | Gly | Ala |
|-----|-----|-----|-----|-----|-----|-----|-----|-----|-----|-----|-----|-----|-----|-----|-----|
|     |     |     |     | 100 |     |     |     |     | 105 |     |     |     | 110 |     |     |

| Phe | Ala | Ser | Val | Trp | Val | Asp | Gly | Glu | Gly | Asn | Val | Ala | Glu | Gly | Pro |
|-----|-----|-----|-----|-----|-----|-----|-----|-----|-----|-----|-----|-----|-----|-----|-----|
|     |     | 115 |     |     |     |     | 120 |     |     |     |     | 125 |     |     |     |

| Met | Val | Asn | Val | Ala | Phe | Val | Thr | Ala | Ala | Gly | Glu | Leu | Val | Leu | Pro |
|-----|-----|-----|-----|-----|-----|-----|-----|-----|-----|-----|-----|-----|-----|-----|-----|
|     | 130 |     |     |     |     | 135 |     |     |     |     | 140 |     |     |     |     |

| Ala | Phe | Asp | Lys | Ile | Leu | Ala | Gly | Cys | Thr | Ala | Lys | Arg | Leu | Leu | Ala |
|-----|-----|-----|-----|-----|-----|-----|-----|-----|-----|-----|-----|-----|-----|-----|-----|
| 145 |     |     |     |     | 150 |     |     |     |     | 155 |     |     |     |     | 160 |

| Leu | Ala | Pro | Arg | Leu | Val | Glu | Ser | Gly | Leu | Leu | Lys | Ala | Val | Thr | Thr |
|-----|-----|-----|-----|-----|-----|-----|-----|-----|-----|-----|-----|-----|-----|-----|-----|
|     |     |     |     | 165 |     |     |     |     | 170 |     |     |     |     | 175 |     |

| Arg | His | Ile | Ala | Ala | Asp | Glu | Ala | Lys | Arg | Cys | Ser | Ala | Glu | Met | Ala |
|-----|-----|-----|-----|-----|-----|-----|-----|-----|-----|-----|-----|-----|-----|-----|-----|
|     |     |     |     | 180 |     |     |     |     | 185 |     |     |     | 190 |     |     |

| Phe | Val | Gly | Ser | Gly | Leu | Pro | Val | Leu | Pro | Ile | Val | Glu | Trp | Asp | Asp |
|-----|-----|-----|-----|-----|-----|-----|-----|-----|-----|-----|-----|-----|-----|-----|-----|
|     |     | 195 |     |     |     |     | 200 |     |     |     |     | 205 |     |     |     |

| Gln | Leu | Ile | Gly | Asp | Gly | Lys | Val | Gly | Lys | Thr | Met | Met | Ala | Leu | Ser |
|-----|-----|-----|-----|-----|-----|-----|-----|-----|-----|-----|-----|-----|-----|-----|-----|
|     | 210 |     |     |     |     | 215 |     |     |     |     | 220 |     |     |     |     |

| Asp | Leu | Leu | Trp | Glu | Asp | Met | Lys | Ser | Gly | Pro | Asp | Arg | Ile | Ala | Val |
|-----|-----|-----|-----|-----|-----|-----|-----|-----|-----|-----|-----|-----|-----|-----|-----|
| 225 |     |     |     |     | 230 |     |     |     |     | 235 |     |     |     |     | 240 |

Pro Tyr Lys

<210> SEQ ID NO 23
<211> LENGTH: 1045
<212> TYPE: DNA
<213> ORGANISM: Glycine max

<400> SEQUENCE: 23

```
gcacgaggct atggttattc ctatggatga ccacatggtc cacagaggcc acggtgtctt    60
tgatactgca gcaataatgg atggatacct atatgagcta gatcaacacc ttgatcgctt   120
tttaaggtca gcatccatgt ctaaaataga tcccccattt gatcgaggaa gcataagaag   180
aatactcata caaactgtaa gtgcttccaa gtgtagaaaa ggatcactaa gatattggct   240
ctcggcagga cctggcgact ttcagttatc tccctcttgt tgccaccgat caagtctgta   300
tgcgatagta atacaggatc tgtcaccatc ctcacctaat ttcaggggcg ttaaagttgt   360
cacttcatct attcccatta aacaccccaa gtttgctatc actaagagtg tgaactatct   420
tccaaatgtg ctctcaaagg tggaagctga agaagctggt gcttttgtag catttggct   480
tgatggtgaa ggttttgttg ctgaagggcc taatatgaat gtggcctttg tcactaaaga   540
taaggaactt ataatgccac actttgacaa aattctaagt ggctgcacag ctaagagagt   600
tttaacccct gctgagagct tgttaaggga gggtaagctt aaagggataa gggtgaaaac   660
```

-continued

```
tgtgactgtc gaggaaggta agcaagcaga tgaaatgatg cttcttggca gcggagttct    720
tgtttgccct gtagtgcaat gggatgagca ggttattggt gatggcaaag aaggccctat    780
aacgcaggct ctcttaaatc taattgttga ggacatgaaa tcaggtccct ccactgttcg    840
tatacctgtt ccttattgac acaactttat ttccttctct tcattttgta atgaagatta    900
atcagtagtt gtgatgcccc tacttctaca gggaggaatg actattaata acttcattgt    960
ctaatggttt ttagagcttg tagtgttata agaaactcta ttccatggag cttagttttc   1020
aaatgttttt gtggtctaaa aaaaa                                          1045
```

<210> SEQ ID NO 24
<211> LENGTH: 285
<212> TYPE: PRT
<213> ORGANISM: Glycine max

<400> SEQUENCE: 24

```
His Glu Ala Met Val Ile Pro Met Asp Asp His Met Val His Arg Gly
  1               5                  10                  15

His Gly Val Phe Asp Thr Ala Ala Ile Met Asp Gly Tyr Leu Tyr Glu
             20                  25                  30

Leu Asp Gln His Leu Asp Arg Phe Leu Arg Ser Ala Ser Met Ser Lys
         35                  40                  45

Ile Asp Pro Pro Phe Asp Arg Gly Ser Ile Arg Ile Leu Ile Gln
     50                  55                  60

Thr Val Ser Ala Ser Lys Cys Arg Lys Gly Ser Leu Arg Tyr Trp Leu
 65                  70                  75                  80

Ser Ala Gly Pro Gly Asp Phe Gln Leu Ser Pro Ser Cys Cys His Arg
                 85                  90                  95

Ser Ser Leu Tyr Ala Ile Val Ile Gln Asp Leu Ser Pro Ser Ser Pro
            100                 105                 110

Asn Phe Arg Gly Val Lys Val Thr Ser Ser Ile Pro Ile Lys His
        115                 120                 125

Pro Lys Phe Ala Ile Thr Lys Ser Val Asn Tyr Leu Pro Asn Val Leu
    130                 135                 140

Ser Lys Val Glu Ala Glu Ala Gly Ala Phe Val Gly Ile Trp Leu
145                 150                 155                 160

Asp Gly Glu Gly Phe Val Ala Glu Gly Pro Asn Met Asn Val Ala Phe
                165                 170                 175

Val Thr Lys Asp Lys Glu Leu Ile Met Pro His Phe Asp Lys Ile Leu
            180                 185                 190

Ser Gly Cys Thr Ala Lys Arg Val Leu Thr Leu Ala Glu Ser Leu Leu
        195                 200                 205

Arg Glu Gly Lys Leu Lys Gly Ile Arg Val Lys Thr Val Thr Val Glu
    210                 215                 220

Glu Gly Lys Gln Ala Asp Glu Met Met Leu Leu Gly Ser Gly Val Leu
225                 230                 235                 240

Val Cys Pro Val Val Gln Trp Asp Glu Gln Val Ile Gly Asp Gly Lys
                245                 250                 255

Glu Gly Pro Ile Thr Gln Ala Leu Leu Asn Leu Ile Val Glu Asp Met
            260                 265                 270

Lys Ser Gly Pro Ser Thr Val Arg Ile Pro Val Pro Tyr
        275                 280                 285
```

<210> SEQ ID NO 25
<211> LENGTH: 1323

<212> TYPE: DNA
<213> ORGANISM: Oryza sativa

<400> SEQUENCE: 25

```
gcacgagagg aaccccactc acaagtcccc tgaggttgaa atgatggtg atttttaaagt    60
tcatctgttc tcttcatcat ccgagttgct tgaaaagctt catgaaaaat ggagttcagt   120
ggagaaacca ccatacccag ctatgtattc tagtatttat ggaggtatca tacttgatcc   180
agcaatgatg gtaatcccca ttgatgatca catggttcac agagggcatg gtgtgtttga   240
tacagctatt gttctagatg gatacctcta tgagttggat gttcaccttg acagattcct   300
aagttcagcc tccaaagcaa agatatcctc tcccttttct cgatcagtgc ttcacagcat   360
tctaatacaa ctaactgcag catcaaaatg caagaaggga actctaagat actggctcag   420
tgcaggtcct ggagatttct tgctatcatc agcaggatgt ccaacatctg cattctatgc   480
agtagtcatt gaccaagatg tttcccaatg caagagggga gttaaagtga ttacttccaa   540
cataccaatg aagccttctc tatttgccac agccaaaaat gtgaactatc ttccaaatgt   600
cctttcagta atggaagctg aagagaaagg agcatcttct tctatatggg ttgatgagga   660
aggttatatt gctgaaggtc caaatgtgaa tgttgctttc ataactcaag acaaggaact   720
tgtcatgcct ccttttgata acatcttaca tggttgcact gcaaaaaggc tccttgaact   780
ggcacccaag ttggttgatc aagggcttct gaaaggtgta gcaactaaaa aactaactgt   840
ggaggaagct aaagctgctg ctgaaatgat gtatgtagga agcacgcttc ctctgttgcc   900
tatcatcgtc tgggatgatc aacccattgg caacggaagg gtgggagaat taacaatgtt   960
actttcggat atgctttggg atgatatggt agctggccct ggcacacaga ggataccgtgt  1020
tccttatgtt gagtaaacct acaaagtcat caaattacag gctgggaaca actttcttac  1080
ttttctatgt catgttccta ggagttctcc ttgcaaagat ttatcaagag gtttctcttt  1140
gtatttgctt tttgtatttc aagtgtgaac actgaacaag tcctaaagtg aagcaccagg  1200
tgtttcctgc aacgcaaaat ttacgtagca gataaatagt ccttgaactg tttcacgttg  1260
ttgtattgat ataataataa taatgaagac ccttcatgct gctttgtgcc tgaaaaaaaa  1320
aaa                                                                1323
```

<210> SEQ ID NO 26
<211> LENGTH: 297
<212> TYPE: PRT
<213> ORGANISM: Oryza sativa

<400> SEQUENCE: 26

```
Met Tyr Ser Ser Ile Tyr Gly Gly Ile Ile Leu Asp Pro Ala Met Met
  1               5                  10                  15

Val Ile Pro Ile Asp Asp His Met Val His Arg Gly His Gly Val Phe
                 20                  25                  30

Asp Thr Ala Ile Val Leu Asp Gly Tyr Leu Tyr Glu Leu Asp Val His
             35                  40                  45

Leu Asp Arg Phe Leu Ser Ser Ala Ser Lys Ala Lys Ile Ser Ser Pro
         50                  55                  60

Phe Ser Arg Ser Val Leu His Ser Ile Leu Ile Gln Leu Thr Ala Ala
 65                  70                  75                  80

Ser Lys Cys Lys Lys Gly Thr Leu Arg Tyr Trp Leu Ser Ala Gly Pro
                 85                  90                  95

Gly Asp Phe Leu Leu Ser Ser Ala Gly Cys Pro Thr Ser Ala Phe Tyr
                100                 105                 110
```

```
Ala Val Val Ile Asp Gln Asp Val Ser Gln Cys Lys Glu Gly Val Lys
            115                 120                 125
Val Ile Thr Ser Asn Ile Pro Met Lys Pro Ser Leu Phe Ala Thr Ala
        130                 135                 140
Lys Asn Val Asn Tyr Leu Pro Asn Val Leu Ser Val Met Glu Ala Glu
145                 150                 155                 160
Glu Lys Gly Ala Ser Ser Ile Trp Val Asp Glu Gly Tyr Ile
                165                 170                 175
Ala Glu Gly Pro Asn Val Asn Val Ala Phe Ile Thr Gln Asp Lys Glu
            180                 185                 190
Leu Val Met Pro Pro Phe Asp Asn Ile Leu His Gly Cys Thr Ala Lys
        195                 200                 205
Arg Leu Leu Glu Leu Ala Pro Lys Leu Val Asp Gln Gly Leu Leu Lys
        210                 215                 220
Gly Val Ala Thr Lys Lys Leu Thr Val Glu Glu Ala Lys Ala Ala Ala
225                 230                 235                 240
Glu Met Met Tyr Val Gly Ser Thr Leu Pro Leu Leu Pro Ile Ile Val
                245                 250                 255
Trp Asp Asp Gln Pro Ile Gly Asn Gly Arg Val Gly Glu Leu Thr Met
            260                 265                 270
Leu Leu Ser Asp Met Leu Trp Asp Asp Met Val Ala Gly Pro Gly Thr
        275                 280                 285
Gln Arg Ile Pro Val Pro Tyr Val Glu
        290                 295

<210> SEQ ID NO 27
<211> LENGTH: 542
<212> TYPE: DNA
<213> ORGANISM: Triticum aestivum

<400> SEQUENCE: 27
gcacgaggtt atcttcatct ggctgtacaa acccagccct ctatgctgtt gttattgaaa     60
gcccatcctt acaagtaccg tcctgctgca gagtggtcac atcatctata ccgataaagt    120
ctcctcaatt tgcagtcatg aaaagcgtga attacttgcc caatgcactc accaaggtgg    180
aaggagaaga gaatggtgca tttactggca tttggctaga cgatgagggc ttcgttgcag    240
agggttcgaa catgaatgtt ggcttcgtga caaagaacaa ggagcttctc atgcctcgtt    300
ttgacaagat cctgagtggg tgcacagcaa gacgggttct gaccctcgct gagcatctag    360
tagctcatgg aaagctcagc aggtaatat caaggaatgt gagtgttgag gaagggaaga    420
tggccgatga gatgatgctc atcggtagtg gcattcttgt caaacctgtt gttcagtggg    480
atgataagat aattggttct ggacaagaag gcccgatagc tcaagcgtag tatgacataa    540
tt                                                                   542

<210> SEQ ID NO 28
<211> LENGTH: 180
<212> TYPE: PRT
<213> ORGANISM: Triticum aestivum

<400> SEQUENCE: 28

Thr Arg Leu Ser Ser Ser Gly Cys Thr Asn Pro Ala Leu Tyr Ala Val
  1               5                  10                  15
Val Ile Glu Ser Pro Ser Leu Gln Val Pro Ser Cys Cys Arg Val Val
                 20                  25                  30
```

```
Thr Ser Ser Ile Pro Ile Lys Ser Pro Gln Phe Ala Val Met Lys Ser
        35                  40                  45

Val Asn Tyr Leu Pro Asn Ala Leu Thr Lys Val Glu Gly Glu Glu Asn
 50                  55                  60

Gly Ala Phe Thr Gly Ile Trp Leu Asp Asp Glu Gly Phe Val Ala Glu
 65                  70                  75                  80

Gly Ser Asn Met Asn Val Gly Phe Val Thr Lys Asn Lys Glu Leu Leu
                 85                  90                  95

Met Pro Arg Phe Asp Lys Ile Leu Ser Gly Cys Thr Ala Arg Arg Val
            100                 105                 110

Leu Thr Leu Ala Glu His Leu Val Ala His Gly Lys Leu Ser Arg Val
        115                 120                 125

Ile Ser Arg Asn Val Ser Val Glu Glu Gly Lys Met Ala Asp Glu Met
    130                 135                 140

Met Leu Ile Gly Ser Gly Ile Leu Val Lys Pro Val Val Gln Trp Asp
145                 150                 155                 160

Asp Lys Ile Ile Gly Ser Gly Gln Glu Gly Pro Ile Ala Gln Ala Leu
                165                 170                 175

Tyr Asp Leu Ile
            180
```

<210> SEQ ID NO 29
<211> LENGTH: 288
<212> TYPE: PRT
<213> ORGANISM: Methanococcus jannaschii

<400> SEQUENCE: 29

```
Met Lys Ile Tyr Leu Asn Gly Lys Phe Val Asp Glu Lys Asp Ala Lys
 1               5                  10                  15

Val Ser Val Phe Asp His Gly Leu Leu Tyr Gly Asp Gly Val Phe Glu
                 20                  25                  30

Gly Ile Arg Ala Tyr Asp Gly Val Val Phe Met Leu Lys Glu His Ile
            35                  40                  45

Asp Arg Leu Tyr Asp Ser Ala Lys Ser Leu Cys Ile Asp Ile Pro Leu
     50                  55                  60

Thr Lys Glu Glu Met Ile Asp Val Val Leu Glu Thr Leu Arg Val Asn
 65                  70                  75                  80

Asn Leu Arg Asp Ala Tyr Ile Arg Leu Val Val Thr Arg Gly Val Gly
                 85                  90                  95

Asp Leu Gly Leu Asp Pro Arg Lys Cys Gly Lys Pro Thr Ile Phe Cys
            100                 105                 110

Ile Ala Ile Pro Met Pro Pro Leu Leu Gly Glu Asp Gly Ile Arg Ala
        115                 120                 125

Ile Thr Val Ser Val Arg Arg Leu Pro Val Asp Val Leu Asn Pro Ala
    130                 135                 140

Val Lys Ser Leu Asn Tyr Leu Asn Ser Val Leu Ala Lys Ile Gln Ala
145                 150                 155                 160

Asn Tyr Ala Gly Val Asp Glu Ala Phe Leu Leu Asp Asp Lys Gly Phe
                165                 170                 175

Val Val Glu Gly Thr Gly Asp Asn Ile Phe Ile Val Lys Asn Gly Val
            180                 185                 190

Leu Lys Thr Pro Pro Val Tyr Gln Ser Ile Leu Lys Gly Ile Thr Arg
        195                 200                 205

Asp Val Val Ile Lys Leu Ala Lys Glu Glu Gly Ile Glu Val Val Glu
    210                 215                 220
```

Glu Pro Leu Thr Leu His Asp Leu Tyr Thr Ala Asp Glu Leu Phe Ile
225                 230                 235                 240

Thr Gly Thr Ala Ala Glu Ile Val Pro Val Phe Glu Ile Asp Gly Arg
            245                 250                 255

Val Ile Asn Asn Lys Gln Val Gly Glu Ile Thr Lys Lys Leu Lys Glu
        260                 265                 270

Lys Phe Lys Asp Ile Arg Thr Lys Trp Gly Ile Lys Val Tyr Asp Glu
    275                 280                 285

<210> SEQ ID NO 30
<211> LENGTH: 1062
<212> TYPE: DNA
<213> ORGANISM: Zea mays

<400> SEQUENCE: 30

| | | |
|---|---|---|
| gcaaccacca ttatcggacc ctcctctgcc tgtccctgca aataaaaaca ttcttgtttg | 60 |
| ggttggagat gaacttttgc cccgtaacag tgcaaaggtt tcagtgtttg attcagttgt | 120 |
| acaaggagga gatgctgttt gggaaggttt acgtatatat gatggaaaag tattcaaatt | 180 |
| agatgaacat ttggacagat tgtttgattc tgcaaaagct atggccttca gcaatgtgcc | 240 |
| tactcgtgat tggattaagg atgccatctt taagactctg attgcaaatg gaatgttcaa | 300 |
| caatgctcat ataaggctca cgctcacccg tgggaaaaag gtgacatctg aatgagtcc | 360 |
| agctttcaat ctttatgggt gtgccttgat tgtgcttgca gagtgaaaac accagttta | 420 |
| tgataactct catgggataa aattggttac tgccaccaca cgtcgaaatt ctccaaatag | 480 |
| tatagatccc aagattcatc acaacaatct tatcaacaat attctggcaa agatagaagg | 540 |
| taatcttgcc caggctgagg atgccattat gctagataag gatggctttg tatcagaaac | 600 |
| aaacgcaaca aatatttta tggtcaaaaa gggaattgta ttgacacctc atgctgacta | 660 |
| ttgccttcca ggcattacgc gagcaactgt catggatctt gtggtgaaag aaaactttgt | 720 |
| gttacatgaa cgacgcatta gtctgtcaga attccatgct gcagatgagg tatggacaac | 780 |
| cggaacaatg ggtgaaatca caccggttgt aatgattgat ggacgtgaaa tcggcgacgg | 840 |
| gaaaattggt ccagtcacta gacaaatcca gaaggcatac aagatcctga cagcagggca | 900 |
| aggagtaccg ataccggggg ttgctgaggt gtaattgtct aagatgcatc cctttatcta | 960 |
| gttaggatca gtcccccaag aagctcaatg atatcaggct agcgcaacaa taaattaata | 1020 |
| atctgcattg atcactgatg ttcaaaaaaa aaaaaaaaa aa | 1062 |

<210> SEQ ID NO 31
<211> LENGTH: 310
<212> TYPE: PRT
<213> ORGANISM: Zea mays

<400> SEQUENCE: 31

Gln Pro Pro Leu Ser Asp Pro Pro Leu Pro Val Pro Ala Asn Lys Asn
1               5                   10                  15

Ile Leu Val Trp Val Gly Asp Glu Leu Leu Pro Arg Asn Ser Ala Lys
            20                  25                  30

Val Ser Val Phe Asp Ser Val Val Gln Gly Gly Asp Ala Val Trp Glu
        35                  40                  45

Gly Leu Arg Ile Tyr Asp Gly Lys Val Phe Lys Leu Asp Glu His Leu
    50                  55                  60

Asp Arg Leu Phe Asp Ser Ala Lys Ala Met Ala Phe Ser Asn Val Pro
65                  70                  75                  80

```
Thr Arg Asp Trp Ile Lys Asp Ala Ile Phe Lys Thr Leu Ile Ala Asn
            85                  90                  95
Gly Met Phe Asn Asn Ala His Ile Arg Leu Thr Leu Thr Arg Gly Lys
            100                 105                 110
Lys Val Thr Ser Gly Met Ser Pro Ala Phe Asn Leu Tyr Gly Cys Ala
            115                 120                 125
Leu Ile Val Leu Ala Glu Trp Lys Pro Pro Val Tyr Asp Asn Ser His
            130                 135                 140
Gly Ile Lys Leu Val Thr Ala Thr Thr Arg Arg Asn Ser Pro Asn Ser
145                 150                 155                 160
Ile Asp Pro Lys Ile His His Asn Asn Leu Ile Asn Asn Ile Leu Ala
            165                 170                 175
Lys Ile Glu Gly Asn Leu Ala Gln Ala Glu Asp Ala Ile Met Leu Asp
            180                 185                 190
Lys Asp Gly Phe Val Ser Glu Thr Asn Ala Thr Asn Ile Phe Met Val
            195                 200                 205
Lys Lys Gly Ile Val Leu Thr Pro His Ala Asp Tyr Cys Leu Pro Gly
            210                 215                 220
Ile Thr Arg Ala Thr Val Met Asp Leu Val Val Lys Glu Asn Phe Val
225                 230                 235                 240
Leu His Glu Arg Arg Ile Ser Leu Ser Glu Phe His Ala Ala Asp Glu
            245                 250                 255
Val Trp Thr Thr Gly Thr Met Gly Glu Ile Thr Pro Val Val Met Ile
            260                 265                 270
Asp Gly Arg Glu Ile Gly Asp Gly Lys Ile Gly Pro Val Thr Arg Gln
            275                 280                 285
Ile Gln Lys Ala Tyr Lys Ile Leu Thr Ala Gly Gln Gly Val Pro Ile
            290                 295                 300
Pro Gly Val Ala Glu Val
305                 310
```

<210> SEQ ID NO 32
<211> LENGTH: 1186
<212> TYPE: DNA
<213> ORGANISM: Triticum aestivum

<400> SEQUENCE: 32

| | | | | | |
|---|---|---|---|---|---|
| gcacgagtca | aacttgaaga | acacttggat | agattgtttg | attctacaaa | agctatggcc | 60 |
| ttcagcaatg | tgcccagtcg | tgattggatt | aaggatgcaa | tatttaagac | tcttaacgca | 120 |
| aatgggatgt | tcaataatgc | acatataagg | ctcactctca | cccgtgggaa | gaaggtgaca | 180 |
| tctggaatga | gtccaacttt | caatctatat | gggtgtgtct | tgattgtact | tgcagagtgg | 240 |
| aaaccaccag | tttatgataa | ctcacatggg | ataaagttgg | taactgccgc | cacacgtcgt | 300 |
| aattctccaa | atagcgtaga | ttcgaagata | catcacaaca | atcttattaa | caacattctg | 360 |
| gcaaagatag | aaggtaatct | tgcacaggct | gaggatgcta | tcatgctaga | tcaagatggt | 420 |
| tttgtatcag | aaacaaatgc | aacaaacata | tttatggtta | agaagggcat | tgtattgaca | 480 |
| cctcatgcgg | actactgcct | tccaggaatt | acccgtgcaa | ctgtcaagga | tcttgttgtg | 540 |
| aaagaaaacc | tggtattaca | tgaacggcga | attagtctat | ctgaatttca | tgctgcagat | 600 |
| gaggtgtgga | caaccggaac | aatgggtgaa | attacaccgg | ttgtgatgat | tgacgggcgt | 660 |
| gaaattggtg | atgggaaaat | cggtctggtc | acaagacaaa | tccagagcgc | atacaaagtc | 720 |
| ctgacagcag | ggttgggagt | aacaattccc | aggaatgcgg | aggcataatc | atttgcgcag | 780 |

-continued

```
acattcttct tgtcctttg aaaaggagaa ggcacctatt atctatggac aaactttcag    840
ggttcagttt cgagtaatga taataaatac ccctccatcc ggaattactt gtcgtagaaa    900
tgggtaaaaa tgaatgtatc tagaactaaa aatacgttta gatacatcta tttctccgac    960
aggtatttcc ggatggaggg agtagtagct agcgttcaaa gaagcaccca gtgaaagtgg   1020
cacaccggac agaaaactga gtattcgaaa atactggct gggtctgtga attcatgatt   1080
tactgtgtgc ctgtgtgcgc cgaacctgtg gctgatcctg gacacagaac agaaaataga   1140
atattatatg cggttttatt ttctgctaaa aaaaaaaaa aaaaaa                  1186
```

<210> SEQ ID NO 33
<211> LENGTH: 255
<212> TYPE: PRT
<213> ORGANISM: Triticum aestivum

<400> SEQUENCE: 33

```
Ala Arg Val Lys Leu Glu Glu His Leu Asp Arg Leu Phe Asp Ser Thr
  1               5                  10                  15

Lys Ala Met Ala Phe Ser Asn Val Pro Ser Arg Asp Trp Ile Lys Asp
             20                  25                  30

Ala Ile Phe Lys Thr Leu Asn Ala Asn Gly Met Phe Asn Asn Ala His
         35                  40                  45

Ile Arg Leu Thr Leu Thr Arg Gly Lys Lys Val Thr Ser Gly Met Ser
     50                  55                  60

Pro Thr Phe Asn Leu Tyr Gly Cys Val Leu Ile Val Leu Ala Glu Trp
 65                  70                  75                  80

Lys Pro Pro Val Tyr Asp Asn Ser His Gly Ile Lys Leu Val Thr Ala
                 85                  90                  95

Ala Thr Arg Arg Asn Ser Pro Asn Ser Val Asp Ser Lys Ile His His
            100                 105                 110

Asn Asn Leu Ile Asn Asn Ile Leu Ala Lys Ile Glu Gly Asn Leu Ala
        115                 120                 125

Gln Ala Glu Asp Ala Ile Met Leu Asp Gln Asp Gly Phe Val Ser Glu
    130                 135                 140

Thr Asn Ala Thr Asn Ile Phe Met Val Lys Lys Gly Ile Val Leu Thr
145                 150                 155                 160

Pro His Ala Asp Tyr Cys Leu Pro Gly Ile Thr Arg Ala Thr Val Lys
                165                 170                 175

Asp Leu Val Val Lys Glu Asn Leu Val Leu His Glu Arg Arg Ile Ser
            180                 185                 190

Leu Ser Glu Phe His Ala Ala Asp Glu Val Trp Thr Thr Gly Thr Met
        195                 200                 205

Gly Glu Ile Thr Pro Val Val Met Ile Asp Gly Arg Glu Ile Gly Asp
    210                 215                 220

Gly Lys Ile Gly Leu Val Thr Arg Gln Ile Gln Ser Ala Tyr Lys Val
225                 230                 235                 240

Leu Thr Ala Gly Leu Gly Val Thr Ile Pro Arg Asn Ala Glu Ala
                245                 250                 255
```

<210> SEQ ID NO 34
<211> LENGTH: 210
<212> TYPE: PRT
<213> ORGANISM: Escherichia coli

<400> SEQUENCE: 34

```
Met Thr Thr Lys Lys Ala Asp Tyr Trp Asn Gly Met Val Arg Trp Asp
 1               5                  10                  15

Ala Lys Val His Val Met Ser His Ala His Tyr Gly Thr Ser Val Gly
            20                  25                  30

Arg Cys Tyr Asp Ser His Lys Gly Val Val Arg His His Met Arg
        35                  40                  45

His Asp Ser Ala Lys Tyr Arg Val Ser Ser Asp Met Ala Cys Arg Asp
    50                  55                  60

Val Arg Lys Asn Asn Thr Ser Ala Tyr Arg Val Gly Asp Val Gly Met
65                  70                  75                  80

Gly Val Asn Ala Gly Tyr Ser Thr Asp Val Ala Ala Trp Gly Ala Tyr
                85                  90                  95

Gly Ala Ala Gly Asp Ala Met Val Ser Ser Trp Asn Arg Ala Ala Asn
                100                 105                 110

Thr Thr Ala Ala Lys Ala Gly Gly Asn Tyr Ser Ser Val Gly Ser Ala
            115                 120                 125

Arg Arg His Gly Tyr Gly Ala Asp Val Asn Gly Tyr Ser Gly Ala Gly
        130                 135                 140

Asn Val Lys Asp Gly Val Thr Thr Ser Ser Ala Gly Thr Arg Asp Ala
145                 150                 155                 160

Lys Ala Lys Gly Val Arg Val Ser Arg Ser Tyr Ala Asp Val Met Ser
                165                 170                 175

Gly Thr Ala Ala Thr Val Arg Ser Val Asp Gly Val Gly Gly Arg Cys
            180                 185                 190

Gly Val Thr Lys Arg Ala Gly Thr Gly Thr Asp Lys Trp Gly Trp Asp
        195                 200                 205

Val Asn
    210

<210> SEQ ID NO 35
<211> LENGTH: 1626
<212> TYPE: DNA
<213> ORGANISM: Zea mays

<400> SEQUENCE: 35
gcacgagagc ccggggagaa cgtgtgggtg gacatcgacg tgctcatgac gcacgacgtc      60
tgcgggcccg gcaccatcgg catcttcaag aaggagttcg gggaggatgc caaggtctgg    120
gaccgcgaga aggtcgtcat catccccgac cactacatct tcaccagcga cgagcgcgcc    180
aaccgcaacg tcgatatcct cagggacttc tgtctggagc agaacatcaa gtacttctat    240
gatatcaagg acctcagcga tttcagggct aatccagact acaagggtgt ctgccacatt    300
gcacttgctc aggaaggcca ctgccgacca ggcgaggttc tcctgggtac tgattctcat    360
acgtgcaatg ctggagcctt tggtcaattt gcaaccggaa ttggaaacac tgatgcaggt    420
tttgtgatgg gcactggaaa ggctcttctc aaggtgccac ctactatcag gtttgtatta    480
gatggagaaa tgccgcctta tttacttgcg aaggatctga ttttgcaaat tattggtgag    540
atttcagtat ctggtgcaac ctacaaatcg atggagtttg ttggatcaac tgtagaaagt    600
ctaaccatgg aagaacgtat gacactatgc aacatggttg ttgaagctgg tgaaagaac    660 ggtgtcgtgc ctgctgatga aactacattt aaataccttg agggtaggac atcagttgat    720
tatcaacctg tctacagtga tgctgaggcc agatttttta gtgactaccg gtttgatgta    780
tcgaaactgg agccagtagt tgccaagcca cattcgcctg acaaccgtgc cctagcaaga    840
gaatgcaaag atgtcaagat cgaccgagtc tatattggtt cctgcactgg tggcaagact    900
```

-continued

```
gaggacttcc ttgctgccgc aaaggtgttc ttagcctcgg gaaagaaggt taaagttccc     960
acattccttg tccctgccac acaaaaggtg tggatggacg tatatagcct tcctgtacca    1020
ggatctggcg gcaaaacttg cgcccagata ttcgaggagg ctggttgtga tacaccagca    1080
agtcctaatt gcggcgcttg tctgggtggc cctcgcgata cgtatgcacg gatgaatgaa    1140
cctacggtct gcgtgtccac cacgaacagg aacttcccgg gcaggatggg gcacaaggaa    1200
gggcagatct acctggcgtc ccctacacc gctgcagcct cggccctgac ggggtacgtc    1260
acggacccca gggacttcct catgtgaacg atcttgaaac agccacagag tgcctgcacc    1320
gctgtttttt gtgttgaacc ttagtttagg cgtgtgccct tcgttgagaa ataaactccc    1380
atgtcgggag gctgccattg ccatttatgt tttttgcgtt atatttatta cagtgactgc    1440
cgataacgta gttgagcgtt acaagggaaa tacattcatt ctttccagta tcgatggcag    1500
tcactagact ccgttcttac aaaaaaaagg catgtcgaga gatcttgtag ttcatacact    1560
tgttaaaaca cttttttgta caatgtatgg gaaagaagct cagtcgaaaa aaaaaaaaaa    1620
aaaaaa                                                              1626
```

<210> SEQ ID NO 36
<211> LENGTH: 428
<212> TYPE: PRT
<213> ORGANISM: Zea mays

<400> SEQUENCE: 36

```
Ala Arg Glu Pro Gly Glu Asn Val Trp Val Asp Ile Asp Val Leu Met
  1               5                  10                  15

Thr His Asp Val Cys Gly Pro Thr Ile Gly Ile Phe Lys Lys Glu
                 20                  25                  30

Phe Gly Glu Asp Ala Lys Val Trp Asp Arg Glu Lys Val Val Ile Ile
         35                  40                  45

Pro Asp His Tyr Ile Phe Thr Ser Asp Glu Arg Ala Asn Arg Asn Val
     50                  55                  60

Asp Ile Leu Arg Asp Phe Cys Leu Glu Gln Asn Ile Lys Tyr Phe Tyr
 65                  70                  75                  80

Asp Ile Lys Asp Leu Ser Asp Phe Arg Ala Asn Pro Asp Tyr Lys Gly
                 85                  90                  95

Val Cys His Ile Ala Leu Ala Gln Glu Gly His Cys Arg Pro Gly Glu
            100                 105                 110

Val Leu Leu Gly Thr Asp Ser His Thr Cys Asn Ala Gly Ala Phe Gly
        115                 120                 125

Gln Phe Ala Thr Gly Ile Gly Asn Thr Asp Ala Gly Phe Val Met Gly
    130                 135                 140

Thr Gly Lys Ala Leu Leu Lys Val Pro Pro Thr Ile Arg Phe Val Leu
145                 150                 155                 160

Asp Gly Glu Met Pro Pro Tyr Leu Leu Ala Lys Asp Leu Ile Leu Gln
                165                 170                 175

Ile Ile Gly Glu Ile Ser Val Ser Gly Ala Thr Tyr Lys Ser Met Glu
            180                 185                 190

Phe Val Gly Ser Thr Val Glu Ser Leu Thr Met Glu Glu Arg Met Thr
        195                 200                 205

Leu Cys Asn Met Val Val Glu Ala Gly Gly Lys Asn Gly Val Val Pro
    210                 215                 220

Ala Asp Glu Thr Thr Phe Lys Tyr Leu Glu Gly Arg Thr Ser Val Asp
225                 230                 235                 240
```

-continued

```
Tyr Gln Pro Val Tyr Ser Asp Ala Glu Ala Arg Phe Phe Ser Asp Tyr
            245                 250                 255

Arg Phe Asp Val Ser Lys Leu Glu Pro Val Val Ala Lys Pro His Ser
            260                 265                 270

Pro Asp Asn Arg Ala Leu Ala Arg Glu Cys Lys Asp Val Lys Ile Asp
            275                 280                 285

Arg Val Tyr Ile Gly Ser Cys Thr Gly Gly Lys Thr Glu Asp Phe Leu
            290                 295                 300

Ala Ala Ala Lys Val Phe Leu Ala Ser Gly Lys Lys Val Lys Val Pro
305                 310                 315                 320

Thr Phe Leu Val Pro Ala Thr Gln Lys Val Trp Met Asp Val Tyr Ser
            325                 330                 335

Leu Pro Val Pro Gly Ser Gly Gly Lys Thr Cys Ala Gln Ile Phe Glu
            340                 345                 350

Glu Ala Gly Cys Asp Thr Pro Ala Ser Pro Asn Cys Gly Ala Cys Leu
            355                 360                 365

Gly Gly Pro Arg Asp Thr Tyr Ala Arg Met Asn Glu Pro Thr Val Cys
370                 375                 380

Val Ser Thr Thr Asn Arg Asn Phe Pro Gly Arg Met Gly His Lys Glu
385                 390                 395                 400

Gly Gln Ile Tyr Leu Ala Ser Pro Tyr Thr Ala Ala Ser Ala Leu
            405                 410                 415

Thr Gly Tyr Val Thr Asp Pro Arg Asp Phe Leu Met
            420                 425
```

<210> SEQ ID NO 37
<211> LENGTH: 1688
<212> TYPE: DNA
<213> ORGANISM: Zea mays
<220> FEATURE:
<221> NAME/KEY: unsure
<222> LOCATION: (1673)

<400> SEQUENCE: 37

```
gcacgagctg acgcaccacc ccgaagccct cccgccgcgc tcgcagggtg ttcgacccgtt      60
cgcccgcgcg ccctcacgac atggcctcct ccgtctccgc cgccgccaag gccgccgcgg     120
cgttcgcgca caaggtccag aaggagctgg ccgcgccggc gcagcgccgc gcgggcttga     180
cccgccggac caagccgtgc agcgtgcgcg ccgtcgcttc gcccgcgcgc gccctgtcgt     240
ccaccggctc ggtgaagagc gcgatgacga tgacggagaa gatactggcg cgggcgtcgg     300
agcgcgcggc gctggagccc ggggagaacg tgtgggtcga cgtcgacgtg ctcatgacgc     360
acgacgtctg cgggcccggc gccttcgaca tcttcaagaa ggagttcggg gaggacgcca     420
gggtctggga ccgcgagaag ctcgtcgtca tcccggacca ctacatcttc accagcgacg     480
gccgtgccaa acgcaacgtc gacatcctca gggacttctg tgcggagcag aacatcaagt     540
acttctatga catcaaggac ctcagcgatt tcagggctaa tccggactac aaaggcgtct     600
gccacatcgc acttgctcag gaagcccact gccgaccagg cgaggttctc ttgggcactg     660
attctcatac atgcaatgct ggagcttttg gtcagttgc aactggaatc ggaaacactg      720
atgcaggttt tgtgttgggc actggaaagg ctcttctcaa ggtgccacct actatcaggt     780
ttatattaga tggagagatg ccgccttatt tacttgcgaa ggatctgatt ttgcaaatta     840
ttggagagat tcagtatct ggtgcgacct acaaatcaat ggagtttgtt ggatcaactg      900
tagaaagtct aaccatggaa gagcgtatga cactatgcaa catggttatt gaagctggtg     960
```

-continued

```
gaaagaacgg tgttgtgcct gctgatgaaa ctacatttaa ataccttgag ggtaagacat    1020
cagtcgatta tgaacctgtc tacagtgatg ctcaagccag attttttagc gactaccggt    1080
ttgatgtatc aaaactggag ccagtagttg ccaagccaca ttcgcctgac aaccgtgctc    1140
cagcacgaga atgcaaagat gtgaagatcg accgagtcta tattggttct tgcactggtg    1200
gtaagaccga ggatttcctt gctgctgcaa aggtgttctt agcctcggga agaaggtta     1260 aagttcccac atttcttgtc cctgccacac aaaaggtgtg gttggacata tatagcctcc    1320
ctgtaccagg atctggtggc aaaacttgct cccagatatt tgaggaggct ggttgtgaca    1380
caccagcaag tcctaattgt ggtgcttgtt tgggtggccc tcgtgataca tatgcacgga    1440
tgaatgaacc tactgtctgc gtgtccacca cgaacaggaa ctttccgggc aggatgggcc    1500
acaaggaagg gcaaatctac ctggcgtctc cctacactgc ggctgcctca gccctgacgg    1560
ggtatgttac ggaccccaag gacttcctca tgtaaccgtc ttgaaacaac aacagatttc    1620
atgatgtaac agagtggttg tactgctgtt tttcgtgctg aacttttgtc cangcatgtc    1680
cttcgttg                                                             1688
```

<210> SEQ ID NO 38
<211> LENGTH: 443
<212> TYPE: PRT
<213> ORGANISM: Zea mays

<400> SEQUENCE: 38

```
Met Thr Met Thr Glu Lys Ile Leu Ala Arg Ala Ser Glu Arg Ala Ala
 1               5                  10                  15

Leu Glu Pro Gly Glu Asn Val Trp Val Asp Val Asp Val Leu Met Thr
                20                  25                  30

His Asp Val Cys Gly Pro Gly Ala Phe Asp Ile Phe Lys Lys Glu Phe
            35                  40                  45

Gly Glu Asp Ala Arg Val Trp Asp Arg Glu Lys Leu Val Val Ile Pro
        50                  55                  60

Asp His Tyr Ile Phe Thr Ser Asp Gly Arg Ala Lys Arg Asn Val Asp
    65                  70                  75                  80

Ile Leu Arg Asp Phe Cys Ala Glu Gln Asn Ile Lys Tyr Phe Tyr Asp
                85                  90                  95

Ile Lys Asp Leu Ser Asp Phe Arg Ala Asn Pro Asp Tyr Lys Gly Val
               100                 105                 110

Cys His Ile Ala Leu Ala Gln Glu Ala His Cys Arg Pro Gly Glu Val
           115                 120                 125

Leu Leu Gly Thr Asp Ser His Thr Cys Asn Ala Gly Ala Phe Gly Gln
       130                 135                 140

Phe Ala Thr Gly Ile Gly Asn Thr Asp Ala Gly Phe Val Leu Gly Thr
145                 150                 155                 160

Gly Lys Ala Leu Leu Lys Val Pro Pro Thr Ile Arg Phe Ile Leu Asp
               165                 170                 175

Gly Glu Met Pro Pro Tyr Leu Leu Ala Lys Asp Leu Ile Leu Gln Ile
           180                 185                 190

Ile Gly Glu Ile Ser Val Ser Gly Ala Thr Tyr Lys Ser Met Glu Phe
       195                 200                 205

Val Gly Ser Thr Val Glu Ser Leu Thr Met Glu Glu Arg Met Thr Leu
   210                 215                 220

Cys Asn Met Val Ile Glu Ala Gly Gly Lys Asn Gly Val Val Pro Ala
225                 230                 235                 240
```

```
Asp Glu Thr Thr Phe Lys Tyr Leu Glu Gly Lys Thr Ser Val Asp Tyr
            245                 250                 255
Glu Pro Val Tyr Ser Asp Ala Gln Ala Arg Phe Phe Ser Asp Tyr Arg
        260                 265                 270
Phe Asp Val Ser Lys Leu Glu Pro Val Val Ala Lys Pro His Ser Pro
        275                 280                 285
Asp Asn Arg Ala Pro Ala Arg Glu Cys Lys Asp Val Lys Ile Asp Arg
        290                 295                 300
Val Tyr Ile Gly Ser Cys Thr Gly Lys Thr Glu Asp Phe Leu Ala
305                 310                 315                 320
Ala Ala Lys Val Phe Leu Ala Ser Gly Lys Lys Val Lys Val Pro Thr
            325                 330                 335
Phe Leu Val Pro Ala Thr Gln Lys Val Trp Leu Asp Ile Tyr Ser Leu
            340                 345                 350
Pro Val Pro Gly Ser Gly Lys Thr Cys Ser Gln Ile Phe Glu Glu
            355                 360                 365
Ala Gly Cys Asp Thr Pro Ala Ser Pro Asn Cys Gly Ala Cys Leu Gly
        370                 375                 380
Gly Pro Arg Asp Thr Tyr Ala Arg Met Asn Glu Pro Thr Val Cys Val
385                 390                 395                 400
Ser Thr Thr Asn Arg Asn Phe Pro Gly Arg Met Gly His Lys Glu Gly
                405                 410                 415
Gln Ile Tyr Leu Ala Ser Pro Tyr Thr Ala Ala Ala Ser Ala Leu Thr
            420                 425                 430
Gly Tyr Val Thr Asp Pro Lys Asp Phe Leu Met
            435                 440

<210> SEQ ID NO 39
<211> LENGTH: 512
<212> TYPE: DNA
<213> ORGANISM: Oryza sativa
<220> FEATURE:
<221> NAME/KEY: unsure
<222> LOCATION: (303)..(303)
<220> FEATURE:
<221> NAME/KEY: unsure
<222> LOCATION: (331)
<220> FEATURE:
<221> NAME/KEY: unsure
<222> LOCATION: (400)
<220> FEATURE:
<221> NAME/KEY: unsure
<222> LOCATION: (467)
<220> FEATURE:
<221> NAME/KEY: unsure
<222> LOCATION: (486)
<220> FEATURE:
<221> NAME/KEY: unsure
<222> LOCATION: (495)
<220> FEATURE:
<221> NAME/KEY: unsure
<222> LOCATION: (509)

<400> SEQUENCE: 39
cttacagttt gccacgttgc tcttgctcaa gagggtcatt gcagaccagg cgaggttctc      60
cttggtactg attctcatac atgcaatgct ggagcctttg ccaatttgc aactggaatt     120 ggaaacactg atgctggttt tgtgatgggc actgggaagg ctcttcttaa ggtgcctcca     180
actatcaggt ttgtattaga tggagaaatg ccaccttatt tacttgcaaa ggatctgatt     240
ttacaaatta ttggtgagat ttctgtatct ggcgcaacat acaaatccat ggagtttgtt     300
```

-continued

```
ggntcaactg tggaaagtct aaatatggaa nagcgaatga cactgtgcaa catggttatt      360
gaagctggtg gcaagaatgg tgttgtgcct gcccgatcan actacattta actatcttga      420
gggcaagaca tcagttgaat acgagccgt catagtgatg ctcaagncaa atttgttagt       480
gactancggt ttgangtatc caaattgggng ca                                   512
```

<210> SEQ ID NO 40
<211> LENGTH: 127
<212> TYPE: PRT
<213> ORGANISM: Oryza sativa
<220> FEATURE:
<221> NAME/KEY: UNSURE
<222> LOCATION: (109)

<400> SEQUENCE: 40

```
Val Cys His Val Ala Leu Ala Gln Glu Gly His Cys Arg Pro Gly Glu
  1               5                  10                  15

Val Leu Leu Gly Thr Asp Ser His Thr Cys Asn Ala Gly Ala Phe Gly
                 20                  25                  30

Gln Phe Ala Thr Gly Ile Gly Asn Thr Asp Ala Gly Phe Val Met Gly
             35                  40                  45

Thr Gly Lys Ala Leu Leu Lys Val Pro Pro Thr Ile Arg Phe Val Leu
         50                  55                  60

Asp Gly Glu Met Pro Pro Tyr Leu Leu Ala Lys Asp Leu Ile Leu Gln
 65                  70                  75                  80

Ile Ile Gly Glu Ile Ser Val Ser Gly Ala Thr Tyr Lys Ser Met Glu
                 85                  90                  95

Phe Val Gly Ser Thr Val Glu Ser Leu Asn Met Glu Xaa Arg Met Thr
                100                 105                 110

Leu Cys Asn Met Val Ile Glu Ala Gly Gly Lys Asn Gly Val Val
            115                 120                 125
```

<210> SEQ ID NO 41
<211> LENGTH: 823
<212> TYPE: DNA
<213> ORGANISM: Glycine max

<400> SEQUENCE: 41

```
cttgagggca agacatctct gccatatgaa cctgtttata gtgacgatca agcaagattt      60
ctcgcagagt atagatttga tgtctcaaaa ttggagccag tggtggccaa gcctcattct     120
ccggataatc gtgctttggc aagagagtgc aaggatgtga aaattgacag agtatacata     180
ggatcttgta caggtggcaa aacagaggat tcatggctg cagcaaaagt ttttctggca      240
tcaggtaaac aggtcaaagt tcctacattt cttgtgcytg caacacaaaa ggtttggatg     300
gacttgtact ccctcccctgt ccctggatct ggtggtaaga catgctcaca gatatttgaa    360
gaagttgggt gtgacacacc agctagtcct agttgtggtg cttgtttggg tgcccaaaa     420 gatacttacg cacgcatgaa tgaacctaag gtttgtgttt caactacgaa caggaacttc    480
ccgggccgaa tggacacaa ggaagtcaa atctatttgg cttcccctta tacagctgct      540
gcatctgcat tgaccggtta tgttactgat cctagagagt tcttgtagta aatgttgtt     600 acaatcatct cattgtgttg tactcgttgt tggttatttg tgtattctct actctctact    660
agtcataagt taaaactgac aactatttaa gcttaaccaa tctttagta tttctaagtt     720 gatctttaga atcattcata tatgtgggtt aggtcaattc agatcaacat gaagttcaat    780
ttcaaattta gtagtgtttg gtcttttaaa aaaaaaaaaa aaa                       823
```

<210> SEQ ID NO 42
<211> LENGTH: 195
<212> TYPE: PRT
<213> ORGANISM: Glycine max
<220> FEATURE:
<221> NAME/KEY: UNSURE
<222> LOCATION: (93)

<400> SEQUENCE: 42

```
Leu Glu Gly Lys Thr Ser Leu Pro Tyr Glu Pro Val Tyr Ser Asp Asp
  1               5                  10                  15

Gln Ala Arg Phe Leu Ala Glu Tyr Arg Phe Asp Val Ser Lys Leu Glu
             20                  25                  30

Pro Val Val Ala Lys Pro His Ser Pro Asp Asn Arg Ala Leu Ala Arg
         35                  40                  45

Glu Cys Lys Asp Val Lys Ile Asp Arg Val Tyr Ile Gly Ser Cys Thr
     50                  55                  60

Gly Gly Lys Thr Glu Asp Phe Met Ala Ala Lys Val Phe Leu Ala
 65                  70                  75                  80

Ser Gly Lys Gln Val Lys Val Pro Thr Phe Leu Val Xaa Ala Thr Gln
             85                  90                  95

Lys Val Trp Met Asp Leu Tyr Ser Leu Pro Val Pro Gly Ser Gly Gly
            100                 105                 110

Lys Thr Cys Ser Gln Ile Phe Glu Glu Val Gly Cys Asp Thr Pro Ala
        115                 120                 125

Ser Pro Ser Cys Gly Ala Cys Leu Gly Gly Pro Lys Asp Thr Tyr Ala
    130                 135                 140

Arg Met Asn Glu Pro Lys Val Cys Val Ser Thr Thr Asn Arg Asn Phe
145                 150                 155                 160

Pro Gly Arg Met Gly His Lys Glu Gly Gln Ile Tyr Leu Ala Ser Pro
                165                 170                 175

Tyr Thr Ala Ala Ala Ser Ala Leu Thr Gly Tyr Val Thr Asp Pro Arg
            180                 185                 190

Glu Phe Leu
        195
```

<210> SEQ ID NO 43
<211> LENGTH: 530
<212> TYPE: DNA
<213> ORGANISM: Triticum aestivum

<400> SEQUENCE: 43

```
gcacgagctt tattgctgct gcaaaggtgt tcttagcttc gggcaagaag gttaaggttc      60
ccactttct cgttcctgcg actcaaaagg tgtggatgga cgtgtatagt ctccccgtac     120
caggatctgg tggcaaaaca tgctcccaga tatttgaaga ggctggttgt gatacaccag    180
ctagtcctaa ttgtggtgct tgtttgggtg gtcctcgtga tacatatgca cggatgaatg    240
aacctacggt ctgtgtatca acgacgaaca ggaacttccc gggcaggatg gccacaagg     300
aagggcagat ctacctggct ctctccttca ccgcggcggc ctcagctttg acgggatatg    360
tcacggaccc caggggcttc ctgtcgtaga gatcttgaaa acaatgaatt tgtgttgcgg    420
accgtcctgt actggtactt tttgttcgtg ttcgaaactg tagtttagat gcgtcatgtg    480
tgtgtcgtgc tgagaaataa gctactcaac gagtagcagt gtaactgtt                530
```

<210> SEQ ID NO 44
<211> LENGTH: 126

```
<212> TYPE: PRT
<213> ORGANISM: Triticum aestivum

<400> SEQUENCE: 44

Phe Ile Ala Ala Ala Lys Val Phe Leu Ala Ser Gly Lys Lys Val Lys
  1               5                  10                  15

Val Pro Thr Phe Leu Val Pro Ala Thr Gln Lys Val Trp Met Asp Val
             20                  25                  30

Tyr Ser Leu Pro Val Pro Gly Ser Gly Lys Thr Cys Ser Gln Ile
         35                  40                  45

Phe Glu Glu Ala Gly Cys Asp Thr Pro Ala Ser Pro Asn Cys Gly Ala
     50                  55                  60

Cys Leu Gly Gly Pro Arg Asp Thr Tyr Ala Arg Met Asn Glu Pro Thr
 65                  70                  75                  80

Val Cys Val Ser Thr Thr Asn Arg Asn Phe Pro Gly Arg Met Gly His
                 85                  90                  95

Lys Glu Gly Gln Ile Tyr Leu Ala Ser Pro Phe Thr Ala Ala Ala Ser
            100                 105                 110

Ala Leu Thr Gly Tyr Val Thr Asp Pro Arg Asp Phe Leu Ser
        115                 120                 125

<210> SEQ ID NO 45
<211> LENGTH: 424
<212> TYPE: PRT
<213> ORGANISM: Methanococcus jannaschii

<400> SEQUENCE: 45

Met Gly Met Thr Ile Val Glu Lys Ile Leu Ala Lys Ala Ser Gly Lys
  1               5                  10                  15

Lys Glu Val Ser Pro Gly Asp Ile Val Met Ala Asn Ile Asp Val Ala
             20                  25                  30

Met Val His Asp Ile Thr Gly Pro Leu Thr Val Asn Thr Leu Lys Glu
         35                  40                  45

Tyr Gly Ile Glu Lys Val Trp Asn Pro Glu Lys Ile Val Ile Leu Phe
     50                  55                  60

Asp His Gln Val Pro Ala Asp Ser Ile Lys Ala Ala Glu Asn His Ile
 65                  70                  75                  80

Leu Met Arg Lys Phe Val Lys Glu Gln Gly Ile Lys Tyr Phe Tyr Asp
                 85                  90                  95

Ile Arg Glu Gly Val Cys His Gln Val Leu Pro Glu Lys Gly His Val
            100                 105                 110

Ala Pro Gly Glu Val Val Gly Ala Asp Ser His Thr Cys Thr His
        115                 120                 125

Gly Ala Phe Gly Ala Phe Ala Thr Gly Ile Gly Ser Thr Asp Met Ala
130                 135                 140

His Val Phe Ala Thr Gly Lys Leu Trp Phe Lys Val Pro Glu Thr Ile
145                 150                 155                 160

Tyr Phe Asn Ile Thr Gly Asp Leu Gln Pro Tyr Val Thr Ser Lys Asp
                165                 170                 175

Val Ile Leu Ser Ile Ile Gly Glu Val Gly Val Asp Gly Ala Thr Tyr
            180                 185                 190

Lys Ala Cys Gln Phe Gly Gly Glu Thr Val Lys Lys Met Ser Ile Ala
        195                 200                 205

Ser Arg Met Thr Met Thr Asn Met Ala Ile Glu Met Gly Gly Lys Thr
    210                 215                 220
```

Gly Ile Ile Glu Pro Asp Glu Lys Thr Ile Gln Tyr Val Lys Glu Ala
225                 230                 235                 240

Met Lys Lys His Gly Thr Glu Arg Pro Phe Glu Val Ile Lys Gly Asp
                245                 250                 255

Glu Asp Ala Glu Phe Ala Glu Val Tyr Glu Ile Glu Ala Asp Lys Ile
            260                 265                 270

Glu Pro Val Phe Ala Cys Pro His Asn Val Asp Asn Val Lys Gln Ala
        275                 280                 285

Arg Glu Val Ala Gly Lys Pro Ile Asp Gln Val Phe Ile Gly Ser Cys
290                 295                 300

Thr Asn Gly Arg Leu Glu Asp Leu Arg Met Ala Ile Lys Ile Ile Glu
305                 310                 315                 320

Lys His Gly Gly Ile Ala Asp Asp Val Arg Val Val Thr Pro Ala
                325                 330                 335

Ser Arg Glu Glu Tyr Leu Lys Ala Leu Lys Glu Gly Ile Ile Glu Lys
            340                 345                 350

Phe Leu Lys Tyr Gly Cys Val Val Thr Asn Pro Ser Cys Ser Ala Cys
            355                 360                 365

Met Gly Ser Leu Tyr Gly Val Leu Gly Pro Gly Glu Val Cys Val Ser
        370                 375                 380

Thr Ser Asn Arg Asn Phe Arg Gly Arg Gln Gly Ser Leu Glu Ala Glu
385                 390                 395                 400

Ile Tyr Leu Ala Ser Pro Ile Thr Ala Ala Cys Ala Val Lys Gly
                405                 410                 415

Glu Leu Val Asp Pro Arg Asp Leu
            420

<210> SEQ ID NO 46
<211> LENGTH: 1033
<212> TYPE: DNA
<213> ORGANISM: Zea mays

<400> SEQUENCE: 46
atcatggcgg cggctctgtc ggggacggcg gtgtccacgg cagcgcttct agccccaatc      60
cgagctccaa ccagcgcgtt tatccggcgc tcccagctca cctgtcatcg cctccactca     120
ctaaaatgcc gccgcgctgg gtccatcgtc cccgcggccg ctgctgccgc ggcgggcagc     180
agctcgccgt cgtcagccgt tttccacggc gagtgcttcg tggtgggcga caatatcgac     240
accgaccaga tcatccccgc cgagcacctc actctggtgc cctccaagcc ggacgagtac     300
cgcaagctcg gttccttcgc cttcgcgggg ctcccatccg cggcctaccc gacgccgttc     360
gtcgctccgg gtgaggagtc ctcccgctac gccatcattg tcgcggagc caacttcggg     420 tgcggttcct ctcgcgagca cgcgcccgtc gcgcttgggg ccgctggcgc acgcgccatt     480
gttgcsgagg gctacgcgcg catcttttt cgcaactccg tggccactgg agaggtgtac     540
cctctggagc tcacggacgt tggggcctgg aaggagtgca agacagggga tgtggtcacc     600
gtggaccttg ctaactccgt ttttattaac cacacctctg gcaaggagta caagctgaaa     660
ccaattggtg atgctggccc tgtaattgag gcgggaggga tctttgccta cgcccggaag     720
acaggaatga ttgcgtcgaa agctgctgca tgagggaaag cttatgcagc cgagcctctg     780
cggagatgaa gaagtaagct ggagttagga ctaagagtta ctgcacctac ttgatgtcga     840
cggtgtctca aaataagttg cggcctaccg aaattatgat gaatcaatca atttggtctt     900
tgtcacagat cgttttttt tgttactagt acttgtacaa ttgtactcct gcctgctact     960

```
gttcttatct gtttgaataa ctgctctgtt gccaaaaaaa aaaaaaaaaa aaaaaaaaaa    1020
aaaaaaaaaa aaa                                                       1033
```

<210> SEQ ID NO 47
<211> LENGTH: 249
<212> TYPE: PRT
<213> ORGANISM: Zea mays

<400> SEQUENCE: 47

```
Met Ala Ala Ala Leu Ser Gly Thr Ala Val Ser Thr Ala Ala Leu Leu
 1               5                  10                  15

Ala Pro Ile Arg Ala Pro Thr Ser Ala Phe Ile Arg Arg Ser Gln Leu
            20                  25                  30

Thr Cys His Arg Leu His Ser Leu Lys Cys Arg Arg Ala Gly Ser Ile
        35                  40                  45

Val Pro Ala Ala Ala Ala Ala Ala Gly Ser Ser Ser Pro Ser Ser
    50                  55                  60

Ala Val Phe His Gly Glu Cys Phe Val Val Gly Asp Asn Ile Asp Thr
 65                  70                  75                  80

Asp Gln Ile Ile Pro Ala Glu His Leu Thr Leu Val Pro Ser Lys Pro
                85                  90                  95

Asp Glu Tyr Arg Lys Leu Gly Ser Phe Ala Phe Ala Gly Leu Pro Ser
            100                 105                 110

Ala Ala Tyr Pro Thr Pro Phe Val Ala Pro Gly Glu Glu Ser Ser Arg
        115                 120                 125

Tyr Ala Ile Ile Val Gly Gly Ala Asn Phe Gly Cys Gly Ser Ser Arg
    130                 135                 140

Glu His Ala Pro Val Ala Leu Gly Ala Ala Gly Ala Arg Ala Ile Val
145                 150                 155                 160

Ala Glu Gly Tyr Ala Arg Ile Phe Phe Arg Asn Ser Val Ala Thr Gly
                165                 170                 175

Glu Val Tyr Pro Leu Glu Leu Thr Asp Val Gly Ala Trp Lys Glu Cys
            180                 185                 190

Lys Thr Gly Asp Val Val Thr Val Asp Leu Ala Asn Ser Val Phe Ile
        195                 200                 205

Asn His Thr Ser Gly Lys Glu Tyr Lys Leu Lys Pro Ile Gly Asp Ala
    210                 215                 220

Gly Pro Val Ile Glu Ala Gly Gly Ile Phe Ala Tyr Ala Arg Lys Thr
225                 230                 235                 240

Gly Met Ile Ala Ser Lys Ala Ala Ala
                245
```

<210> SEQ ID NO 48
<211> LENGTH: 1112
<212> TYPE: DNA
<213> ORGANISM: Oryza sativa

<400> SEQUENCE: 48

```
gaagtggttc tccctcacac actgaacacc atggcggcgg cggcggcggc tccggctcta     60
tccttggccg aggcggcgcc ggtgacagca gttctggcac cgtgtcccac gccctcgagg    120
acgttccgcc gccgcagctg gtcgcggct atctgccggc cgccctgaa atgccaccac    180 agtcgtcccc tgaccgccgt ggtcgccgcg gctgcggctg ccgctgcggc ggggactcg    240 acgtcggccg gcgtattcca cggcgagtgc ttcgtcgtgg gggataacat cgacaccgac    300
cagatcatcc cggccgagca cctgacccttg gtcccgtcca agcccgacga gtaccgcaag    360
```

```
ctcggctcgt tcgccttcgt cggcctcccc accgcggcct acccgacgcc gttcgtcgcc    420
cccggcgagg agaccacccg ctacgccgtc atcatcggcg cgccaacttc cggctgcggc    480
tcctcccgcg agcacgcgcc cgtcgccctg ggcgccgccg cgcccgcgc cgtcgtggcc    540 gagggctacg cgcgcatctt cttccgcaac tccgtggcca ccggtgaggt ctacccgttg    600
gagctagcgg acactggagc ctggaaggag tgcaagaccg gggatgtggt cacggtggaa    660
cttgataatt gcgtcatgat caaccacaca tccggcaagc agtacaagct gaagcctatc    720
ggcgatgccg gccggttat tgaggcaggc gggatctttg cctatgcccg gaagaccgga    780
atgatcgcat ccaagtctgc gtgagggaaa ggcgagtttg gtctgctgtc aagatagtcg    840
aggcctctgc agatagcaag taagactggg ttgtggattt gaacctattg cacctctatg    900
cgattgtcca tcagttgtac tgctgttttt acctaggttg tgtgtcatca gtggtgtttt    960
tggaataagt taaagttac agagtactga actatgatgt attagtccat gtgatcttat   1020
gtaacacctt atgtaataca ctcgtttata cctgccgatt tgcctatctc gtttcgataa   1080
aaaaaaaaaa aaaaaaaaaa aaaaaaaaaa aa                                 1112
```

<210> SEQ ID NO 49
<211> LENGTH: 257
<212> TYPE: PRT
<213> ORGANISM: Oryza sativa

<400> SEQUENCE: 49

```
Met Ala Ala Ala Ala Ala Pro Ala Leu Ser Leu Ala Glu Ala Ala
1               5                   10                  15

Pro Val Thr Ala Val Leu Ala Pro Cys Pro Thr Pro Ser Arg Thr Phe
            20                  25                  30

Arg Arg Arg Ser Trp Val Ala Ile Cys Arg Pro Ala Leu Lys Cys
        35                  40                  45

His His Ser Arg Pro Leu Thr Ala Val Val Ala Ala Ala Ala
    50                  55                  60

Ala Ala Ala Gly Asp Ser Thr Ser Ala Gly Val Phe His Gly Glu Cys
65                  70                  75                  80

Phe Val Val Gly Asp Asn Ile Asp Thr Asp Gln Ile Ile Pro Ala Glu
                85                  90                  95

His Leu Thr Leu Val Pro Ser Lys Pro Asp Glu Tyr Arg Lys Leu Gly
            100                 105                 110

Ser Phe Ala Phe Val Gly Leu Pro Thr Ala Ala Tyr Pro Thr Pro Phe
        115                 120                 125

Val Ala Pro Gly Glu Glu Thr Thr Arg Tyr Ala Val Ile Ile Gly Gly
    130                 135                 140

Ala Asn Phe Gly Cys Gly Ser Ser Arg Glu His Ala Pro Val Ala Leu
145                 150                 155                 160

Gly Ala Ala Gly Ala Arg Ala Val Val Ala Glu Gly Tyr Ala Arg Ile
                165                 170                 175

Phe Phe Arg Asn Ser Val Ala Thr Gly Glu Val Tyr Pro Leu Glu Leu
            180                 185                 190

Ala Asp Thr Gly Ala Trp Lys Glu Cys Lys Thr Gly Asp Val Val Thr
        195                 200                 205

Val Glu Leu Asp Asn Cys Val Met Ile Asn His Thr Ser Gly Lys Gln
    210                 215                 220

Tyr Lys Leu Lys Pro Ile Gly Asp Ala Gly Pro Val Ile Glu Ala Gly
225                 230                 235                 240
```

Gly Ile Phe Ala Tyr Ala Arg Lys Thr Gly Met Ile Ala Ser Lys Ser
                245                 250                 255

Ala

<210> SEQ ID NO 50
<211> LENGTH: 1107
<212> TYPE: DNA
<213> ORGANISM: Glycine max

<400> SEQUENCE: 50

```
tggaaatgag aaaatagacg gaagtgagag aggaggcact gagcatccaa caatggcctt      60
gcacgaggtt ctcttctgcc gcaaccgttc ttcctcggaa cctggcattc accaaactct     120
ccctctctca ctctcacact cttctaccgc gcttcctttc tttcccaact cccaagtcat     180
caaaccctcg caaccgcgtc gcagtctctc tccaaacccc acgcgctcaa tccgccgcgt     240
ccgcttctcc ctccgcctcc ttccacggcc tctgctacgt cgtcggcgac aatatcgaca     300
ccgaccagat cattcccgcc gagtacctca ccctcgtccc ttccaagccc gacgagtacg     360
agaagctcgg ctcctacgcc ctcatcggcc tccccgccac ctacgccacg cgtttcatcg     420
aacccggcga gatcaaaacc aagtacgcca tcgtcatcgg cggtgccaac ttcggttgcg     480
gctcctcccg cgagcacgcc cccgtcgcgc tgggcgcctc cggcgccgcc gcagtggtcg     540
cggagtcgta cgctaggatc ttctttcgga actccgtggc caccggcgag gtgtatccgc     600
tagagtcgga gggacgcctc tgcgaggagt gcaccaccgg cgatgtggtg acgattgagc     660
tcggagagag ccgcttgatc aatcacacca ccggaaagga gtatcgcttg aaaccgatcg     720
gcgacgcggg tccagtgatc gaggccggtg gcatctttgc ctatgccagg aaaaccggca     780
tgattccctc tcgttgagtt cttcaggtga gggcagtgaa ctctgctatc cttgcttcag     840
atgacatgct tctcaagaaa tgtattgacc caatggatgc cttagcttgg tccattatca     900
aataggctag aacttgcaga gatataatac atggcaatag aaagtgtgtt ttaatggttc     960
ttgcatcagc agcttctttt ataatctcat tgatatgggg tatctcatta atgcaaactt    1020
ttgtattcac gaaatgggac caattttgcc ccatttatca atcagaatgg tacttatttt    1080
tcctcgggca aaaaaaaaa aaaaaag                                         1107
```

<210> SEQ ID NO 51
<211> LENGTH: 263
<212> TYPE: PRT
<213> ORGANISM: Glycine max
<220> FEATURE:
<221> NAME/KEY: UNSURE
<222> LOCATION: (4)

<400> SEQUENCE: 51

Met Arg Lys Xaa Thr Glu Val Arg Glu Glu Ala Leu Ser Ile Gln Gln
  1               5                  10                  15

Trp Pro Cys Thr Arg Phe Ser Ser Ala Ala Thr Val Leu Pro Arg Asn
             20                  25                  30

Leu Ala Phe Thr Lys Leu Ser Leu Ser His Ser His Thr Leu Leu Pro
         35                  40                  45

Arg Phe Leu Ser Phe Pro Thr Pro Lys Ser Ser Asn Pro Arg Asn Arg
     50                  55                  60

Val Ala Val Ser Leu Gln Thr Pro Arg Ala Gln Ser Ala Ala Ser Ala
 65                  70                  75                  80

Ser Pro Ser Ala Ser Phe His Gly Leu Cys Tyr Val Val Gly Asp Asn

```
              85                  90                  95
Ile Asp Thr Asp Gln Ile Ile Pro Ala Glu Tyr Leu Thr Leu Val Pro
            100                 105                 110
Ser Lys Pro Asp Glu Tyr Glu Lys Leu Gly Ser Tyr Ala Leu Ile Gly
            115                 120                 125
Leu Pro Ala Thr Tyr Ala Thr Arg Phe Ile Glu Pro Gly Glu Ile Lys
            130                 135                 140
Thr Lys Tyr Ala Ile Val Ile Gly Gly Ala Asn Phe Gly Cys Gly Ser
145                 150                 155                 160
Ser Arg Glu His Ala Pro Val Ala Leu Gly Ala Ser Gly Ala Ala Ala
                165                 170                 175
Val Val Ala Glu Ser Tyr Ala Arg Ile Phe Phe Arg Asn Ser Val Ala
            180                 185                 190
Thr Gly Glu Val Tyr Pro Leu Glu Ser Glu Gly Arg Leu Cys Glu Glu
            195                 200                 205
Cys Thr Thr Gly Asp Val Val Thr Ile Glu Leu Gly Glu Ser Arg Leu
210                 215                 220
Ile Asn His Thr Thr Gly Lys Glu Tyr Arg Leu Lys Pro Ile Gly Asp
225                 230                 235                 240
Ala Gly Pro Val Ile Glu Ala Gly Gly Ile Phe Ala Tyr Ala Arg Lys
            245                 250                 255
Thr Gly Met Ile Pro Ser Arg
            260

<210> SEQ ID NO 52
<211> LENGTH: 995
<212> TYPE: DNA
<213> ORGANISM: Triticum aestivum

<400> SEQUENCE: 52
gcacgagcgg cggtgtccac ggcagcgctt ctagccccaa tccgagctcc aaccagcgcg      60
tttatccggc gctcccagct cacctgtcat cgcctccact cactaaaatg ccgccgcgct     120
gggtccatcg tccccgcggc cgctgctgcc gcggcgggca gcagctcgcc gtcgtcagcc     180
gttttccacg gcgagtgctt cgtggtgggc gacaatatcg acaccgacca gatcatcccc     240
gccgagcacc tcactctggt gccctccaag ccggacgagt accgcaagct cggttccttc     300
gccttcgcgg ggctcccatc gcggcctac ccgacgccgt tcgtcgctcc gggtgaggag      360
tcctcccgct acgccatcat tgtcggcgga gccaacttcg ggtgcggttc ctctcgcgag     420
cacgcgcccg tcgcgcttgg ggccgctggc gcacgcgcca ttgttgcgga gggctacgcg     480
cgcatctttt ttcgcaactc cgtgggcact ggagaggtgt accctctgga gctcacggac     540
gttgggcct ggaaggagtg caagacaggg gatgtggtca ccgtggacct tgctaactcc      600
gtttttatta accacacctc tggcaaggag tacaagctga aaccaattgg tgatgctggc     660
cctgtaattg aggcgggagg gatctttgcc tacgcccgga agacaggaat gattgcgtcg     720
aaagctgctg catgagggaa agatcagctt atgcagccga gcctctgcgg agatgaagaa     780
gtaagctgga gttaggacta agagttactg cacctacttg atgtcgacgg tgtctcaaaa     840
taagttgcgg cctaccgaaa ttatgatgaa tcaatcaatt tggtctttgt cacagatcgt     900
ttttttttgt tactagtact tgtacaattg tactcctgcc tgctactgtt cttatctgtt     960
tgaataactg ctctgttgcc atctaaaaaa aaaaa                               995

<210> SEQ ID NO 53
```

```
<211> LENGTH: 244
<212> TYPE: PRT
<213> ORGANISM: Triticum aestivum

<400> SEQUENCE: 53

Ala Arg Ala Ala Val Ser Thr Ala Ala Leu Leu Ala Pro Ile Arg Ala
 1               5                  10                  15

Pro Thr Ser Ala Phe Ile Arg Arg Ser Gln Leu Thr Cys His Arg Leu
             20                  25                  30

His Ser Leu Lys Cys Arg Arg Ala Gly Ser Ile Val Pro Ala Ala Ala
         35                  40                  45

Ala Ala Ala Ala Gly Ser Ser Ser Pro Ser Ser Ala Val Phe His Gly
     50                  55                  60

Glu Cys Phe Val Val Gly Asp Asn Ile Asp Thr Asp Gln Ile Ile Pro
65                  70                  75                  80

Ala Glu His Leu Thr Leu Val Pro Ser Lys Pro Asp Glu Tyr Arg Lys
                85                  90                  95

Leu Gly Ser Phe Ala Phe Ala Gly Leu Pro Ser Ala Ala Tyr Pro Thr
            100                 105                 110

Pro Phe Val Ala Pro Gly Glu Glu Ser Ser Arg Tyr Ala Ile Ile Val
            115                 120                 125

Gly Gly Ala Asn Phe Gly Cys Gly Ser Ser Arg Glu His Ala Pro Val
        130                 135                 140

Ala Leu Gly Ala Ala Gly Ala Arg Ala Ile Val Ala Glu Gly Tyr Ala
145                 150                 155                 160

Arg Ile Phe Phe Arg Asn Ser Val Gly Thr Gly Glu Val Tyr Pro Leu
                165                 170                 175

Glu Leu Thr Asp Val Gly Ala Trp Lys Glu Cys Lys Thr Gly Asp Val
            180                 185                 190

Val Thr Val Asp Leu Ala Asn Ser Val Phe Ile Asn His Thr Ser Gly
        195                 200                 205

Lys Glu Tyr Lys Leu Lys Pro Ile Gly Asp Ala Gly Pro Val Ile Glu
    210                 215                 220

Ala Gly Gly Ile Phe Ala Tyr Ala Arg Lys Thr Gly Met Ile Ala Ser
225                 230                 235                 240

Lys Ala Ala Ala

<210> SEQ ID NO 54
<211> LENGTH: 113
<212> TYPE: PRT
<213> ORGANISM: Lactococcus lactis

<400> SEQUENCE: 54

Met Lys Thr Tyr Lys Gly Thr Ser Val Val Met Asn Asp Asn Asp Thr
 1               5                  10                  15

Asp Lys Lys Ala Asp Lys Lys Gly Gly Lys Asn Tyr Trp Arg Tyr Lys
             20                  25                  30

Asp Tyr Asp Asn Asp Asn Ala Lys Tyr Lys Ala Ser Ser Gly Asp
         35                  40                  45

Asn Gly Ser Gly Ser Ser Arg His Ala Ala Trp Ala Ser Asp Tyr Gly
     50                  55                  60

Arg Ala Ala Gly Ser Tyr Ser Asp Tyr Asn Asn Ala Lys Asn Gly Lys
65                  70                  75                  80

Arg Val Asn Thr Lys Ser Ser Thr Asp His Thr Ser Gly Asp His Asp
                85                  90                  95
```

-continued

```
Trp Lys Asp Lys Asn Gly Asp Asp Gly Thr Tyr Ala Ser Ala Tyr Lys
            100                 105                 110
Asn
```

PLANT BRANCHED-CHAIN AMINO ACID BIOSYNTHETIC ENZYMES

This application claims the benefit of U.S. Provisional Application No. 60/063,423, filed Oct. 28, 1997.

FIELD OF THE INVENTION

This invention is in the field of plant molecular biology. More specifically, this invention pertains to nucleic acid fragments encoding enzymes involved in biosynthesis and utilization of branched chain amino acids in plants and seeds.

BACKGROUND OF THE INVENTION

Many vertebrates, including man, lack the ability to manufacture a number of amino acids and therefore require these amino acids preformed in their diet. These are called essential amino acids. Plants are able to synthesize all twenty amino acids and serve as the ultimate source of the essential amino acids for humans and animals. Thus, the ability to manipulate the production and accumulation of the essential amino acids in plants would be of considerable importance and value. Furthermore, the inability of animals to synthesize these amino acids provides a useful distinction between animal and plant cellular metabolism. This can be exploited for the discovery of herbicidal chemical compounds that target enzymes in the plant biosynthetic pathways of the essential amino acids and thus have low toxicity to animals.

The branched-chain amino acids leucine, isoleucine and valine are three of the essential amino acids. Biosynthesis of these amino acids proceeds, in part, via the common enzymes acetolactate synthase, acetohydroxyacid reductoisomerase, dihydroxyacid dehydratase and branched chain amino acid aminotransferase, and in part via enzymes specific for one of the amino acids, threonine dehydratase (isoleucine), and α-isopropylmalate synthase, 3-isopropylmalate dehydratase and β-isopropylmalate dehydrogenase (leucine). Regulation of the biosynthesis of each member of this family in plants is interconnected (see FIG. 1), but understanding of the control is poor.

Few of the genes encoding enzymes that regulate this pathway in plants, especially corn, soybeans, rice and wheat, have been isolated and sequenced. For example, no plant genes have yet been reported for dihydroxyacid dehydratase, branched chain amino acid aminotransferase or 3-isopropylmalate dehydratase. Accordingly, the availability of nucleic acid sequences encoding all or a portion of these enzymes would facilitate studies to better understand the cellular control of the pathway, provide genetic tools for the manipulation of the pathway and provide a means to evaluate chemical compounds for their ability to inhibit the activity of these plant enzymes.

SUMMARY OF THE INVENTION

The instant invention relates to isolated nucleic acid fragments encoding plant enzymes involved in biosynthesis and utilization of branched-chain amino acids. Specifically, this invention concerns an isolated nucleic acid fragment encoding a dihydroxyacid dehydratase, a branched chain amino acid aminotransferase, a leuC subunit of 3-isopropylmalate dehydratase, or a leuD subunit of 3-isopropylmalate dehydratase. In addition, this invention relates to a nucleic acid fragment that is complementary to the nucleic acid fragment encoding dihydroxyacid dehydratase, branched chain amino acid aminotransferase, leuC subunit of 3-isopropylmalate dehydratase, or leuD subunit of 3-isopropylmalate dehydratase.

An additional embodiment of the instant invention pertains to a polypeptide encoding all or a substantial portion of a plant branched-chain amino acid biosynthetic enzyme selected from the group consisting of dihydroxyacid dehydratase, branched chain amino acid aminotransferase, leuC subunit of 3-isopropylmalate dehydratase, and leuD subunit of 3-isopropylmalate dehydratase.

In another embodiment, the instant invention relates to a chimeric gene encoding a dihydroxyacid dehydratase, a branched chain amino acid aminotransferase, a leuC subunit of 3-isopropylmalate dehydratase, or a leuD subunit of 3-isopropylmalate dehydratase, or to a chimeric gene that comprises a nucleic acid fragment that is complementary to a nucleic acid fragment encoding a dihydroxyacid dehydratase, a branched chain amino acid aminotransferase, a leuC subunit of 3-isopropylmalate dehydratase, or a leuD subunit of 3-isopropylmalate dehydratase, operably linked to suitable regulatory sequences, wherein expression of the chimeric gene results in production of levels of the encoded protein in a transformed host cell that is altered (i.e., increased or decreased) from the level produced in an untransformed host cell.

In a further embodiment, the instant invention concerns a transformed host cell comprising in its genome a chimeric gene encoding a dihydroxyacid dehydratase, a branched chain amino acid aminotransferase, a leuC subunit of 3-isopropylmalate dehydratase, or a leuD subunit of 3-isopropylmalate dehydratase, operably linked to suitable regulatory sequences. Expression of the chimeric gene results in production of altered levels of the encoded protein in the transformed host cell. The transformed host cell can be of eukaryotic or prokaryotic origin, and include cells derived from higher plants and microorganisms. The invention also includes transformed plants that arise from transformed host cells of higher plants, and seeds derived from such transformed plants.

An additional embodiment of the instant invention concerns a method of altering the level of expression of a dihydroxyacid dehydratase, a branched chain amino acid aminotransferase, a leuC subunit of 3-isopropylmalate dehydratase, or a leuD subunit of 3-isopropylmalate dehydratase in a transformed host cell comprising: a) transforming a host cell with a chimeric gene comprising a nucleic acid fragment encoding a dihydroxyacid dehydratase, a branched chain amino acid aminotransferase, a leuC subunit of 3-isopropylmalate dehydratase, or a leuD subunit of 3-isopropylmalate dehydratase; and b) growing the transformed host cell under conditions that are suitable for expression of the chimeric gene wherein expression of the chimeric gene results in production of altered levels of dihydroxyacid dehydratase, branched chain amino acid aminotransferase, leuC subunit of 3-isopropylmalate dehydratase, or leuD subunit of 3-isopropylmalate dehydratase in the transformed host cell.

An addition embodiment of the instant invention concerns a method for obtaining a nucleic acid fragment encoding all or a substantial portion of an amino acid sequence encoding a dihydroxyacid dehydratase, a branched chain amino acid aminotransferase, a leuC subunit of 3-isopropylmalate dehydratase, or a leuD subunit of 3-isopropylmalate dehydratase.

A further embodiment of the instant invention is a method for evaluating at least one compound for its ability to inhibit the activity of a dihydroxyacid dehydratase, a branched chain amino acid aminotransferase, a leuC subunit of 3-isopropylmalate dehydratase, or a leuD subunit of 3-isopropylmalate dehydratase, the method comprising the steps of: (a) transforming a host cell with a chimeric gene comprising a nucleic acid fragment encoding a dihydroxyacid dehydratase, a branched chain amino acid aminotransferase, a leuC subunit of 3-isopropylmalate dehydratase, or a leuD subunit of 3-isopropylmalate dehydratase, operably linked to suitable regulatory sequences; (b) growing the transformed host cell under conditions that are suitable for expression of the chimeric gene wherein expression of the chimeric gene results in production of dihydroxyacid dehydratase, a branched chain amino acid aminotransferase, a leuC subunit of 3-isopropylmalate dehydratase, or a leuD subunit of 3-isopropylmalate dehydratase in the transformed host cell; (c) optionally purifying the dihydroxyacid dehydratase, the branched chain amino acid aminotransferase, the leuC subunit of 3-isopropylmalate dehydratase, or the leuD subunit of 3-isopropylmalate dehydratase expressed by the transformed host cell; (d) treating the dihydroxyacid dehydratase, the branched chain amino acid aminotransferase, the leuC subunit of 3-isopropylmalate dehydratase, or the leuD subunit of 3-isopropylmalate dehydratase with a compound to be tested; and (e) comparing the activity of the dihydroxyacid dehydratase, the branched chain amino acid aminotransferase, the leuC subunit of 3-isopropylmalate dehydratase, or the leuD subunit of 3-isopropylmalate dehydratase that has been treated with a test compound to the activity of an untreated dihydroxyacid dehydratase, the branched chain amino acid aminotransferase, the leuC subunit of 3-isopropylmalate dehydratase, or the leuD subunit of 3-isopropylmalate dehydratase, thereby selecting compounds with potential for inhibitory activity.

BRIEF DESCRIPTION OF THE DRAWINGS AND SEQUENCE DESCRIPTIONS

The invention can be more fully understood from the following detailed description and the accompanying drawings and Sequence Listing which form a part of this application.

FIG. 1 depicts the metabolic pathway leading to biosynthesis and utilization of the branched chain amino acids isoleucine, valine and leucine. The following abbreviations are used: ALS=acetolactate synthase; AHRI= acetohydroxyacid reductoisomerase; DHAD=dihydroxyacid dehydratase; BCAT=branched chain amino acid aminotransferase; IPMS=isporpoylmalate synthase; IPMD=3-isopropylmalate dehydratase; and IPMDH=isopropylmalate deyhdrogenase.

FIG. 2 depicts the amino acid sequence alignments between the dihydroxyacid dehydratase from corn clone cr1.pk0032.c4 (SEQ ID NO:2), soybean contig assembled from clones se3.pk0006.g4, and ses9c.pk001.o8 (SEQ ID NO:4), wheat clone wkm2c.pk005.c12 (SEQ ID NO:6), and Saccharomyces cerevisiae (NCBI gi Accession No. 1170543, SEQ ID NO:7). Amino acids which are conserved among all sequences are indicated with a plus sign (+) while those conserved only within the plant sequences are indicated by an asterisk (*).

FIG. 3 depicts the amino acid sequence alignments between the branched chain amino acid transaminase from corn clone cc71se-b.pk0008.b5 (SEQ ID NO:9), corn clone cen6.pk0003.b5 (SEQ ID NO:11), corn clone cta1n.pk0070.e7 (SEQ ID NO:13), rice clone rls24.pk0025.f6 (SEQ ID NO:15), soybean clone ses8w.pk0032.e9 (SEQ ID NO:17), wheat clone wlm96.pk027.n2 (SEQ ID NO:19), and Bacillus subtilis (NCBI gi Accession No. 1706292, SEQ ID NO:20). Amino acids which are conserved among all sequences are indicated with a plus sign (+) while those conserved only within the plant sequences are indicated by an asterisk (*).

FIG. 4 depicts the amino acid sequence alignments between the branched chain amino acid transaminase from rice clone rls72.pk0014.a3 (SEQ ID NO:22), soybean clone sre.pk0001.d1 (SEQ ID NO:24), soybean clone srr2c.pk003.d20 (SEQ ID NO:26), wheat clone wl1n.pk0123.c11 (SEQ ID NO:28), and Methanococcus jannaschii (NCBI gi Accession No. 1243 80, SEQ ID NO:29). Amino acids which are conserved among all sequences are indicated with a plus sign (+) while those conserved only within the plant sequences are indicated by an asterisk (*).

FIG. 5 depicts the amino acid sequence alignments between the branched chain amino acid transaminase from corn clone cco1.pk0030.d2 (SEQ ID NO:31), wheat clone wkm1c.pk0004.c7 (SEQ ID NO:33), and Escherichia coli (NCBI gi Accession No. 1705437, SEQ ID NO:34). Amino acids which are conserved among all sequences are indicated with a plus sign (+) while those conserved only within the plant sequences are indicated by an asterisk (*).

FIG. 6 depicts the amino acid sequence alignments between the leuC subunit of 3-isopropylmalate dehydratase from the corn contig assembled from clones cen1.pk0032.b1, cta1n.pk0077.c7, cen3n.pk0015.g3, cen3n.pk0060.h4, and cen3n.pk0121.h11 (SEQ ID NO:36), corn clone cr1n.pk0153.e9 (SEQ ID NO:38), rice clone r10n.pk087.k16 (SEQ ID NO:40), soybean contig assembled from clones sdp3c.pk008.k13, and srm.pk0006.h5 (SEQ ID NO:42), wheat clone wre1n.pk0045.b10 (SEQ ID NO:44), and Rhizomucor pusillus (NCBI gi Accession No. 1708799, SEQ ID NO:45). Amino acids which are conserved among all sequences are indicated with a plus sign (+) while those conserved only within the plant sequences are indicated by an asterisk (*).

FIG. 7 depicts the amino acid sequence alignments between the leuD subunit of 3-isopropylmalate dehydratase from corn clone cr1n.pk0123.b7 (SEQ ID NO:47), rice clone rls12.pk0001.c2 (SEQ ID NO:49), soybean clone srr1c.pk003.c2 (SEQ ID NO:51), wheat clone wl1n.pk0048.a6 (SEQ ID NO:53), and Lactococcus lactis (NCBI gi Accession No. 400187, SEQ ID NO:54). Amino acids which are conserved among all sequences are indicated with a plus sign (+) while those conserved only within the plant sequences are indicated by an asterisk (*).

The following sequence descriptions and the Sequence Listing attached hereto comply with the rules governing nucleotide and/or amino acid sequence disclosures in patent applications as set forth in 37 C.F.R. §1.821–1.825.

SEQ ID NO:1 is the nucleotide sequence comprising the entire cDNA insert in clone cr1.pk0032.c4 encoding a full-length corn dihydroxyacid dehydratase.

SEQ ID NO:2 is the deduced amino acid sequence of a corn dihydroxyacid dehydratase derived from the nucleotide sequence of SEQ ID NO:1.

SEQ ID NO:3 is the nucleotide sequence comprising the contig formed from a portion of the cDNA insert in clone ses9c.pk001.o8 and the entire cDNA insert in clone se3.pk0006.g4 encoding a full-length soybean dihydroxyacid dehydratase.

SEQ ID NO:4 is the deduced amino acid sequence of a soybean dihydroxyacid dehydratase derived from the nucleotide sequence of SEQ ID NO:3.

SEQ ID NO:5 is the nucleotide sequence comprising a portion of the cDNA insert in clone wkm2c.pk005.c12 encoding the C-terminal 156 amino acid from a wheat dihydroxyacid dehydratase.

SEQ ID NO:6 is the deduced amino acid sequence of a fragment from a wheat dihydroxyacid dehydratase derived from the nucleotide sequence of SEQ ID NO:5.

SEQ ID NO:7 is the amino acid sequence of a *Saccharomyces cerevisiae* dihydroxyacid dehydratase (NCBI gi Accession No. 1170543).

SEQ ID NO:8 is the nucleotide sequence comprising a portion of the cDNA insert in clone cc71se-b.pk0008.b5 encoding a fragment of a corn branched chain amino acid transaminase.

SEQ ID NO:9 is the deduced amino acid sequence of a fragment of a corn branched chain amino acid transaminase derived from the nucleotide sequence of SEQ ID NO:8.

SEQ ID NO:10 is the nucleotide sequence comprising the entire cDNA insert in clone cen6.pk0003.b5 encoding the C-terminal half of a corn branched chain amino acid transaminase.

SEQ ID NO:11 is the deduced amino acid sequence of the C-terminal half of a corn branched chain amino acid transaminase derived from the nucleotide sequence of SEQ ID NO:10.

SEQ ID NO:12 is the nucleotide sequence comprising a portion of the cDNA insert in clone cta1n.pk0070.e7 encoding the C-terminal 110 amino acids from a corn branched chain amino acid transaminase.

SEQ ID NO:13 is the deduced amino acid sequence of the C-terminal 110 amino acids from a corn branched chain amino acid transaminase derived from the nucleotide sequence of SEQ ID NO:12.

SEQ ID NO:14 is the nucleotide sequence comprising the entire cDNA insert in clone rls24.pk0025.f6 encoding the C-terminal 75% of a rice branched chain amino acid transaminase.

SEQ ID NO:15 is the deduced amino acid sequence of the C-terminal 75% of a rice branched chain amino acid transaminase derived from the nucleotide sequence of SEQ ID NO:16.

SEQ ID NO:16 is the nucleotide sequence comprising the entire cDNA insert in clone ses8w.pk0032.e9 encoding the N-terminal 60% of a soybean branched chain amino acid transaminase.

SEQ ID NO:17 is the deduced amino acid sequence of the N-terminal 60% of a soybean branched chain amino acid transaminase derived from the nucleotide sequence of SEQID NO:16.

SEQ ID NO:18 is the nucleotide sequence comprising the entire cDNA insert in clone wlm96.pk027.n2 encoding the C-terminal 93% of a wheat branched chain amino acid transaminase.

SEQ ID NO:19 is the deduced amino acid sequence of the C-terminal 93% of a wheat branched chain amino acid transaminase derived from the nucleotide sequence of SEQ ID NO:18.

SEQ ID NO:20 is the amino acid sequence of a *Bacillus subtilis* branched chain amino acid transaminase (NCBI gi Accession No. 1176947).

SEQ ID NO:21 is the nucleotide sequence comprising the entire cDNA insert in clone rls72.pk0014.a3 encoding the C-terminal 82% of a rice branched chain amino acid transaminase.

SEQ ID NO:22 is the deduced amino acid sequence of the C-terminal 82% of a rice branched chain amino acid transaminase derived from the nucleotide sequence of SEQ ID NO:21.

SEQ ID NO:23 is the nucleotide sequence comprising the entire cDNA insert in clone sre.pk0001.d1 encoding a full-length soybean branched chain amino acid transaminase.

SEQ ID NO:24 is the deduced amino acid sequence of a full-length soybean branched chain amino acid transaminase derived from the nucleotide sequence of SEQ ID NO:23.

SEQ ID NO:25 is the nucleotide sequence comprising the entire cDNA insert in clone srr2c.pk003.d20 encoding a full length soybean branched chain amino acid transaminase.

SEQ ID NO:26 is the deduced amino acid sequence of a full length soybean branched chain amino acid transaminase derived from the nucleotide sequence of. SEQ ID NO:25.

SEQ ID NO:27 is the nucleotide sequence comprising the entire cDNA insert in clone wl1n.pk0123.c11 encoding approximately the C-terminal 80% of a wheat branched-chain amino acid transaminase.

SEQ ID NO:28 is the deduced amino acid sequence of approximately the C-terminal 80% of a wheat branched-chain amino acid transaminase derived from the nucleotide sequence of SEQ ID NO:27.

SEQ ID NO:29 is the amino acid sequence of a *Methanococcus jannischii* branched chain amino acid transaminase (NCBI gi Accession No. 3122287).

SEQ ID NO:30 is the nucleotide sequence comprising the entire cDNA insert in clone cco1.pk0030.d2 encoding a full-length corn branched chain amino acid transaminase.

SEQ ID NO:31 is the deduced amino acid sequence of a full-length corn branched chain amino acid transaminase derived from the nucleotide sequence of SEQ ID NO:30.

SEQ ID NO:32 is the nucleotide sequence comprising the entire cDNA insert in clone wkm1c.pk0004.c7 encoding the C-terminal 80% of a wheat branched chain amino acid transaminase.

SEQ ID NO:33 is the deduced amino acid sequence of the C-terminal 80% of a wheat branched chain amino acid transaminase derived from the nucleotide sequence of SEQ ID NO:32.

SEQ ID NO:34 is the amino acid sequence of a *Escherichia coli* branched chain amino acid transaminase (NCBI gi Accession No. 124380).

SEQ ID NO:35 is the nucleotide sequence comprising the contig assembled from the cDNA insert in clones cen1.pk0032.b1, cta1n.pk0077.c7, cen3n.pk0015.g3, cen3n.pk0060.h4, and cen3n.pk0121.h11 encoding a nearly full-length corn leuC subunit of 3-isopropylmalate dehydratase.

SEQ ID NO:36 is the deduced amino acid sequence of a nearly full-length corn leuC subunit of 3-isopropylmalate dehydratase derived from the nucleotide sequence of SEQ ID NO:35.

SEQ ID NO:37 is the nucleotide sequence comprising the entire cDNA insert in clone cr1n.pk0153.e9 encoding a full-length corn leuC subunit of 3-isopropylmalate dehydratase.

SEQ ID NO:38 is the deduced amino acid sequence of a full-length corn leuC subunit of 3-isopropylmalate dehydratase derived from the nucleotide sequence of SEQ ID NO:37.

SEQ ID NO:39 is the nucleotide sequence comprising a portion of the cDNA insert in clone r10n.pk087.k16 encoding a fragment of a rice leuC subunit of 3-isopropylmalate dehydratase.

SEQ ID NO:40 is the deduced amino acid sequence of a fragment of a rice leuC subunit of 3-isopropylmalate dehydratase derived from the nucleotide sequence of SEQ ID NO:39.

SEQ ID NO:41 is the nucleotide sequence comprising a contig assembled from the cDNA insert in clones sdp3c.pk008.k13, and srm.pk0006.h5 encoding the C-terminal half of a soybean leuC subunit of 3-isopropylmalate dehydratase.

SEQ ID NO:42 is the deduced amino acid sequence of the C-terminal half of a soybean leuC subunit of 3-isopropylmalate dehydratase derived from the nucleotide sequence of SEQ ID NO:41.

SEQ ID NO:43 is the nucleotide sequence comprising a portion of the cDNA insert in clone wre1n.pk0045.b10 encoding a portion of a wheat leuC subunit of 3-isopropylmalate dehydratase.

SEQ ID NO:44 is the deduced amino acid sequence of a portion of a wheat leuC subunit of 3-isopropylmalate dehydratase derived from the nucleotide sequence of SEQ ID NO:43.

SEQ ID NO:45 is the amino acid sequence of a *Rhizomucor pusillus* leuC subunit of 3-isopropylmalate dehydratase (NCBI gi Accession No. 1708799).

SEQ ID NO:46 is the nucleotide sequence comprising the entire cDNA insert in clone cr1n.pk0123.b7 encoding a full-length corn leuD subunit of 3-isopropylmalate dehydratase.

SEQ ID NO:47 is the deduced amino acid sequence of a full-length corn leuD subunit of 3-isopropylmalate dehydratase derived from the nucleotide sequence of SEQ ID NO:46.

SEQ ID NO:48 is the nucleotide sequence comprising the entire cDNA insert in clone rls12.pk0001.c2 encoding a full-length rice leuD subunit of 3-isopropylmalate dehydratase.

SEQ ID NO:49 is the deduced amino acid sequence of a full-length rice leuD subunit of 3-isopropylmalate dehydratase derived from the nucleotide sequence of SEQ ID NO:48.

SEQ ID NO:50 is the nucleotide sequence comprising the entire cDNA insert in clone srr1c.pk003.c2 encoding a full-length soybean leuD subunit of 3-isopropylmalate dehydratase.

SEQ ID NO:51 is the deduced amino acid sequence of a full-length soybean leuD subunit of 3-isopropylmalate dehydratase derived from the nucleotide sequence of SEQ ID NO:50.

SEQ ID NO:52 is the nucleotide sequence comprising the entire cDNA insert in clone wl1n.pk0048.a6 encoding a full-length wheat leuD subunit of 3-isopropylmalate dehydratase.

SEQ ID NO:53 is the deduced amino acid sequence of a full-length wheat leuD subunit of 3-isopropylmalate dehydratase derived from the nucleotide sequence of SEQ ID NO:52.

SEQ ID NO:54 is the amino acid sequence of a *Lactococcus lactis* leuD subunit of 3-isopropylmalate dehydratase located in NCBI gi Accession No. 400187.

The Sequence Listing contains the one letter code for nucleotide sequence characters and the three letter codes for amino acids as defined in conformity with the IUPAC-IUBMB standards described in *Nucleic Acids Research* 13:3021–3030 (1985) and in the *Biochemical Journal* 219 (No. 2):345–373 (1984) which are herein incorporated by reference. The symbols and format used for nucleotide and amino acid sequence data comply with the rules set forth in 37 C.F.R. §1.822.

DETAILED DESCRIPTION OF THE INVENTION

In the context of this disclosure, a number of terms shall be utilized. As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA. As used herein, "contig" refers to an assemblage of overlapping nucleic acid sequences to form one contiguous nucleotide sequence. For example, several DNA sequences can be compared and aligned to identify common or overlapping regions. The individual sequences can then be assembled into a single contiguous nucleotide sequence.

As used herein, "substantially similar" refers to nucleic acid fragments wherein changes in one or more nucleotide bases results in substitution of one or more amino acids, but do not affect the functional properties of the protein encoded by the DNA sequence. "Substantially similar" also refers to nucleic acid fragments wherein changes in one or more nucleotide bases does not affect the ability of the nucleic acid fragment to mediate alteration of gene expression by antisense or co-suppression technology. "Substantially similar" also refers to modifications of the nucleic acid fragments of the instant invention such as deletion or insertion of one or more nucleotides that do not substantially affect the functional properties of the resulting transcript vis-à-vis the ability to mediate alteration of gene expression by antisense or co-suppression technology or alteration of the functional properties of the resulting protein molecule. It is therefore understood that the invention encompasses more than the specific exemplary sequences.

For example, it is well known in the art that antisense suppression and co-suppression of gene expression may be accomplished using nucleic acid fragments representing less than the entire coding region of a gene, and by nucleic acid fragments that do not share 100% sequence identity with the gene to be suppressed. Moreover, alterations in a gene which result in the production of a chemically equivalent amino acid at a given site, but do not affect the functional properties of the encoded protein, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the protein molecule would also not be expected to alter the activity of the protein. Each of the proposed modifications is well within the routine skill in the art, as is determination of retention of biological activity of the encoded products. Moreover, the skilled artisan recognizes that substantially similar nucleic acid sequences encompassed by this invention are also defined by their ability to hybridize, under stringent conditions (0.1×SSC, 0.1% SDS, 65° C.), with the sequences exemplified herein. Preferred substantially similar nucleic acid fragments of the instant invention are those nucleic acid fragments whose DNA sequences are 80% identical to the coding sequence of the nucleic acid fragments reported herein. More preferred nucleic acid fragments are 90% identical to the coding sequence of the nucleic acid fragments reported herein. Most preferred are nucleic acid fragments that are 95% identical to the coding sequence of the nucleic acid fragments reported herein.

A "substantial portion" of an amino acid or nucleotide sequence comprises an effective length of the amino acid sequence of a polypeptide or the nucleotide sequence of a gene to conduct correlation assessment and putative identification of that polypeptide or gene, either by manual evaluation of the sequence by one skilled in the art, or by computer-automated sequence comparison and identification using algorithms such as BLAST (Basic Local Alignment Search Tool; Altschul, S. F., et al., (1993) *J. Mol. Biol.* 215:403–410; see also www.ncbi.nlm.nih.gov/BLAST/). In general, a sequence of ten or more contiguous amino acids or thirty or more nucleotides is necessary in order to putatively identify a polypeptide or nucleic acid sequence as homologous to a known protein or gene. Moreover, with respect to nucleotide sequences, gene specific oligonucleotide probes comprising 20–30 contiguous nucleotides may be used in sequence-dependent methods of gene identification (e.g., Southern hybridization) and isolation (e.g., in situ hybridization of bacterial colonies or bacteriophage plaques). In addition, short oligonucleotides of 12–15 bases may be used as amplification primers in PCR in order to obtain a particular nucleic acid fragment comprising the primers. Accordingly, a "substantial portion" of a nucleotide sequence comprises enough of the sequence to afford specific identification and/or isolation of a nucleic acid fragment comprising the sequence. The instant specification teaches partial or complete amino acid and nucleotide sequences encoding one or more particular plant proteins. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions of those sequences as defined above.

"Codon degeneracy" refers to divergence in the genetic code permitting variation of the nucleotide sequence without affecting the amino acid sequence of an encoded polypeptide. Accordingly, the instant invention relates to any nucleic acid fragment that encodes all or a substantial portion of the amino acid sequence encoding the dihydroxyacid dehydratase, the branched chain amino acid aminotransferase, the leuC subunit of 3-isopropylmalate dehydratase, or the leuD subunit of 3-isopropylmalate dehydratase proteins as set forth in SEQ ID NOs:2, 4, 6, 9, 11, 13, 15, 17, 19, 22, 24, 26, 28, 31, 33, 36, 38, 40, 42, 44, 47, 49, 51, and 53. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments which are then enzymatically assembled to construct the entire gene. "Chemically synthesized", as related to a sequence of DNA, means that the component nucleotides were assembled in vitro. Manual chemical synthesis of DNA may be accomplished using well established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure.

"Coding sequence" refers to a DNA sequence that codes for a specific amino acid sequence. "Regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, and polyadenylation recognition sequences.

"Promoter" refers to a DNA sequence capable of controlling the expression of a coding sequence or functional RNA. In general, a coding sequence is located 3' to a promoter sequence. The promoter sequence consists of proximal and more distal upstream elements, the latter elements often referred to as enhancers. Accordingly, an "enhancer" is a DNA sequence which can stimulate promoter activity and may be an innate element of the promoter or a heterologous element inserted to enhance the level or tissue-specificity of a promoter. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental conditions. Promoters which cause a gene to be expressed in most cell types at most times are commonly referred to as "constitutive promoters". New promoters of various types useful in plant cells are constantly being discovered; numerous examples may be found in the compilation by Okamuro and Goldberg, (1989) *Biochemistry of Plants* 15:1–82. It is further recognized that since in most cases the exact boundaries of regulatory sequences have not been completely defined, DNA fragments of different lengths may have identical promoter activity.

The "translation leader sequence" refers to a DNA sequence located between the promoter sequence of a gene and the coding sequence. The translation leader sequence is present in the fully processed mRNA upstream of the translation start sequence. The translation leader sequence may affect processing of the primary transcript to mRNA, mRNA stability or translation efficiency. Examples of translation leader sequences have been described (Turner, R. and Foster, G. D. (1995) *Molecular Biotechnology* 3:225).

The "3' non-coding sequences" refer to DNA sequences located downstream of a coding sequence and include polyadenylation recognition sequences and other sequences encoding regulatory signals capable of affecting mRNA processing or gene expression. The polyadenylation signal is usually characterized by affecting the addition of polyadenylic acid tracts to the 3' end of the mRNA precursor. The use of different 3' non-coding sequences is exemplified by Ingelbrecht et al., (1989) *Plant Cell* 1:671–680.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from posttranscriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065, incorporated herein by reference). The complementarity of an antisense RNA may be with any part of the specific gene transcript, i.e., at the 5' non-coding sequence, 3' non-coding sequence, introns, or the coding sequence. "Functional RNA" refers to antisense RNA, ribozyme RNA, or other RNA that may not be translated but yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide. "Antisense inhibition" refers to the production of antisense RNA transcripts capable of suppressing the expression of the target protein. "Overexpression" refers to the production of a gene product in transgenic organisms that exceeds levels of production in normal or non-transformed organisms. "Co-suppression" refers to the production of sense RNA transcripts capable of suppressing the expression of identical or substantially similar foreign or endogenous genes (U.S. Pat. No. 5,231,020, incorporated herein by reference).

"Altered levels" refers to the production of gene product(s) in transgenic organisms in amounts or proportions that differ from that of normal or non-transformed organisms.

"Mature" protein refers to a post-translationally processed polypeptide; i.e., one from which any pre- or propeptides present in the primary translation product have been removed. "Precursor" protein refers to the primary product of translation of mRNA; i.e., with pre- and propeptides still present. Pre- and propeptides may be but are not limited to intracellular localization signals.

A "chloroplast transit peptide" is an amino acid sequence which is translated in conjunction with a protein and directs the protein to the chloroplast or other plastid types present in the cell in which the protein is made. "Chloroplast transit sequence" refers to a nucleotide sequence that encodes a chloroplast transit peptide. A "signal peptide" is an amino acid sequence which is translated in conjunction with a protein and directs the protein to the secretory system (Chrispeels, J. J., (1991) *Ann. Rev. Plant Phys. Plant Mol. Biol.* 42:21–53). If the protein is to be directed to a vacuole, a vacuolar targeting signal (supra) can further be added, or if to the endoplasmic reticulum, an endoplasmic reticulum retention signal (supra) may be added. If the protein is to be directed to the nucleus, any signal peptide present should be removed and instead a nuclear localization signal included (Raikhel (1992) *Plant Phys.* 100:1627–1632).

"Transformation" refers to the transfer of a nucleic acid fragment into the genome of a host organism, resulting in genetically stable inheritance. Host organisms containing the transformed nucleic acid fragments are referred to as "transgenic" organisms. Examples of methods of plant transformation include Agrobacterium-mediated transformation (De Blaere et al. (1987) *Meth. Enzymol.* 143:277) and particle-accelerated or "gene gun" transformation technology (Klein et al. (1987) *Nature* (London) 327:70–73; U.S. Pat. No. 4,945,050, incorporated herein by reference).

Standard recombinant DNA and molecular cloning techniques used herein are well known in the art and are described more fully in Sambrook, J., Fritsch, E. F. and Maniatis, T. *Molecular Cloning: A Laboratory Manual;* Cold Spring Harbor Laboratory Press: Cold Spring Harbor, 1989 (hereinafter "Maniatis").

Nucleic acid fragments encoding at least a portion of several plant branched chain amino acid biosynthetic enzymes have been isolated and identified by comparison of random plant cDNA sequences to public databases containing nucleotide and protein sequences using the BLAST algorithms well known to those skilled in the art. Table 1 lists the proteins that are described herein, and the designation of the cDNA clones that comprise the nucleic acid fragments encoding these proteins.

TABLE 1

Branched Chain Amino Acid Biosynthetic Enzymes

| Enzyme | Clone | Plant |
| --- | --- | --- |
| Dihydroxyacid dehydratase | cr1.pk0032.c4 | corn |
|  | Contig of: | soybean |
|  | se3.pk0006.g4 |  |
|  | ses9c.pk001.o8 |  |
|  | wkm2c.pk005.c12 | wheat |
| Branched chain amino acid transferase | cc71se-b.pk0008.b5 | corn |
|  | cco1.pk0030.d2 | corn |
|  | cen6.pk0003.b5 | corn |
|  | cta1n.pk0070.e7 | corn |
|  | rls24.pk0025.f6 | rice |
|  | rls72.pk0014.a3 | rice |
|  | ses8w.pk0032.e9 | soybean |
|  | sre.pk0001.d1 | soybean |
|  | srr2c.pk003.d20 | soybean |

TABLE 1-continued

Branched Chain Amino Acid Biosynthetic Enzymes

| Enzyme | Clone | Plant |
|---|---|---|
| | wkm1c.pk0004.c7 | wheat |
| | wl1n.pk0123.c11 | wheat |
| | wlm96.pk027.n2 | wheat |
| leuC subunit of 3-isopropylmalate dehydratase (large subunit) | Contig of: cen1.pk0032.b1 cta1n.pk0077.c7 cen3n.pk0015.g3 cen3n.pk0060.h4 cen3n.pk0121.h11 | corn |
| | cr1n.pk0153.e9 | corn |
| | rl0n.pk087.k16 | rice |
| | Contig of: sdp3c.pk008.k13 srm.pk0006.h5 | soybean |
| | wre1n.pk0045.b10 | wheat |
| leuD subunit of 3-isopropylmalate dehydratase (small subunit) | cr1n.pk0123.b7 | corn |
| | rls12.pk0001.c2 | rice |
| | srr1c.pk003.c2 | soybean |
| | wl1n.pk0048.a6 | wheat |

The nucleic acid fragments of the instant invention may be used to isolate cDNAs and genes encoding homologous proteins from the same or other plant species. Isolation of homologous genes using sequence-dependent protocols is well known in the art. Examples of sequence-dependent protocols include, but are not limited to, methods of nucleic acid hybridization, and methods of DNA and RNA amplification as exemplified by various uses of nucleic acid amplification technologies (e.g., polymerase chain reaction, ligase chain reaction).

For example, genes encoding other dihydroxyacid dehydratase, branched chain amino acid aminotransferase, leuC subunit of 3-isopropylmalate dehydratase, or leuD subunit of 3-isopropylmalate dehydratase, either as cDNAs or genomic DNAs, could be isolated directly by using all or a portion of the instant nucleic acid fragments as DNA hybridization probes to screen libraries from any desired plant employing methodology well known to those skilled in the art. Specific oligonucleotide probes based upon the instant nucleic acid sequences can be designed and synthesized by methods known in the art (Maniatis). Moreover, the entire sequences can be used directly to synthesize DNA probes by methods known to the skilled artisan such as random primer DNA labeling, nick translation, or end-labeling techniques, or RNA probes using available in vitro transcription systems. In addition, specific primers can be designed and used to amplify a part or all of the instant sequences. The resulting amplification products can be labeled directly during amplification reactions or labeled after amplification reactions, and used as probes to isolate full length cDNA or genomic fragments under conditions of appropriate stringency.

In addition, two short segments of the instant nucleic acid fragments may be used in polymerase chain reaction protocols to amplify longer nucleic acid fragments encoding homologous genes from DNA or RNA. The polymerase chain reaction may also be performed on a library of cloned nucleic acid fragments wherein the sequence of one primer is derived from the instant nucleic acid fragments, and the sequence of the other primer takes advantage of the presence of the polyadenylic acid tracts to the 3' end of the mRNA precursor encoding plant genes. Alternatively, the second primer sequence may be based upon sequences derived from the cloning vector. For example, the skilled artisan can follow the RACE protocol (Frohman et al., (1988) *PNAS USA* 85:8998) to generate cDNAs by using PCR to amplify copies of the region between a single point in the transcript and the 3' or 5' end. Primers oriented in the 3' and 5' directions can be designed from the instant sequences. Using commercially available 3' RACE or 5' RACE systems (BRL), specific 3' or 5' cDNA fragments can be isolated (Ohara et al., (1989) *PNAS USA* 86:5673; Loh et al., (1989) *Science* 243:217). Products generated by the 3' and 5' RACE procedures can be combined to generate full-length cDNAs (Frohman, M. A. and Martin, G. R., (1989) *Techniques* 1:165).

Availability of the instant nucleotide and deduced amino acid sequences facilitates immunological screening of cDNA expression libraries. Synthetic peptides representing portions of the instant amino acid sequences may be synthesized. These peptides can be used to immunize animals to produce polyclonal or monoclonal antibodies with specificity for peptides or proteins comprising the amino acid sequences. These antibodies can be then be used to screen cDNA expression libraries to isolate full-length cDNA clones of interest (Lerner, R. A. (1984) *Adv. Immunol.* 36:1; Maniatis).

The nucleic acid fragments of the instant invention may be used to create transgenic plants in which the disclosed dihydroxyacid dehydratase, branched chain amino acid aminotransferase, leuC subunit of 3-isopropylmalate dehydratase, or leuD subunit of 3-isopropylmalate dehydratase are present at higher or lower levels than normal or in cell types or developmental stages in which they are not normally found. This would have the effect of altering the level of branched chain amino acids in those cells. Overexpression of dihydroxyacid dehydratase may produce a greater accumulation of 2-oxo-3-methylvalerate and 2-oxoisovalerate. These two products are substrates for branched chain amino acid aminotransferase which will become the limiting factor to producing higher amounts of leucine, valine, and isoleucine. Overexpression of the 3-isopropylmalate dehydratase subunits will lead to a greater accumulation of leucine precursors, and ultimately to a greater amount of leucine in the cell.

Overexpression of the dihydroxyacid dehydratase, branched chain amino acid aminotransferase, leuC subunit of 3-isopropylmalate dehydratase, or leuD subunit of 3-isopropylmalate dehydratase proteins of the instant invention may be accomplished by first constructing a chimeric gene in which the coding region is operably linked to a promoter capable of directing expression of a gene in the desired tissues at the desired stage of development. For reasons of convenience, the chimeric gene may comprise promoter sequences and translation leader sequences derived from the same genes. 3' Non-coding sequences encoding transcription termination signals may also be provided. The instant chimeric gene may also comprise one or more introns in order to facilitate gene expression.

Plasmid vectors comprising the instant chimeric gene can then constructed. The choice of plasmid vector is dependent upon the method that will be used to transform host plants. The skilled artisan is well aware of the genetic elements that must be present on the plasmid vector in order to successfully transform, select and propagate host cells containing the chimeric gene. The skilled artisan will also recognize that different independent transformation events will result in different levels and patterns of expression (Jones et al., (1985) *EMBO J.* 4:2411–2418; De Almeida et al., (1989) *Mol. Gen. Genetics* 218:78–86), and thus that multiple events must be screened in order to obtain lines displaying the desired expression level and pattern. Such screening may be accomplished by Southern analysis of DNA, Northern analysis of mRNA expression, Western analysis of protein expression, or phenotypic analysis.

For some applications it may be useful to direct the instant branched chain amino acid biosynthetic enzymes to different cellular compartments, or to facilitate its secretion from the cell. It is thus envisioned that the chimeric gene described above may be further supplemented by altering the coding sequence to encode dihydroxyacid dehydratase, a branched chain amino acid aminotransferase, a leuC subunit of 3-isopropylmalate dehydratase, or a leuD subunit of 3-isopropylmalate dehydratase with appropriate intracellular targeting sequences such as transit sequences (Keegstra, K. (1989) *Cell* 56:247–253), signal sequences or sequences encoding endoplasmic reticulum localization (Chrispeels, J. J., (1991) *Ann. Rev. Plant Phys. Plant Mol. Biol.* 42:21–53), or nuclear localization signals (Raikhel, N. (1992) *Plant Phys.* 100:1627–1632) added and/or with targeting sequences that are already present removed. While the references cited give examples of each of these, the list is not exhaustive and more targeting signals of utility may be discovered in the future.

It may also be desirable to reduce or eliminate expression of genes encoding dihydroxyacid dehydratase, branched chain amino acid aminotransferase, leuC subunit of 3-isopropylmalate dehydratase, or leuD subunit of 3-isopropylmalate dehydratase in plants for some applications. In order to accomplish this, a chimeric gene designed for co-suppression of the instant amino acid biosynthetic enzymes can be constructed by linking a gene or gene fragment encoding a dihydroxyacid dehydratase, a branched chain amino acid aminotransferase, a leuC subunit of 3-isopropylmalate dehydratase, or a leuD subunit of 3-isopropylmalate dehydratase to plant promoter sequences. Alternatively, a chimeric gene designed to express antisense RNA for all or part of the instant nucleic acid fragment can be constructed by linking the gene or gene fragment in reverse orientation to plant promoter sequences. Either the co-suppression or antisense chimeric genes could be introduced into plants via transformation wherein expression of the corresponding endogenous genes are reduced or eliminated.

The instant dihydroxyacid dehydratase, branched chain amino acid aminotransferase, leuC subunit of 3-isopropylmalate dehydratase, or leuD subunit of 3-isopropylmalate dehydratase (or portions thereof) may be produced in heterologous host cells, particularly in the cells of microbial hosts, and can be used to prepare antibodies to the these proteins by methods well known to those skilled in the art. The antibodies are useful for detecting dihydroxyacid dehydratase, branched chain amino acid aminotransferase, leuC subunit of 3-isopropylmalate dehydratase, or leuD subunit of 3-isopropylmalate dehydratase in situ in cells or in vitro in cell extracts. Preferred heterologous host cells for production of the instant dihydroxyacid dehydratase, branched chain amino acid aminotransferase, leuC subunit of 3-isopropylmalate dehydratase, or leuD subunit of 3-isopropylmalate dehydratase are microbial hosts. Microbial expression systems and expression vectors containing regulatory sequences that direct high level expression of foreign proteins are well known to those skilled in the art. Any of these could be used to construct a chimeric gene for production of the instant dihydroxyacid dehydratase, branched chain amino acid aminotransferase, leuC subunit of 3-isopropylmalate dehydratase, or leuD subunit of 3-isopropylmalate dehydratase. This chimeric gene could then be introduced into appropriate microorganisms via transformation to provide high level expression of the encoded biosynthetic enzyme. An example of a vector for high level expression of the instant dihydroxyacid dehydratase, branched chain amino acid aminotransferase, leuC subunit of 3-isopropylmalate dehydratase, or leuD subunit of 3-isopropylmalate dehydratase in a bacterial host is provided (Example 9).

Additionally, the instant dihydroxyacid dehydratase, branched chain amino acid aminotransferase, leuC subunit of 3-isopropylmalate dehydratase, or leuD subunit of 3-isopropylmalate dehydratase can be used as a targets to facilitate design and/or identification of inhibitors of those enzymes that may be useful as herbicides. This is desirable because the dihydroxyacid dehydratase, the branched chain amino acid aminotransferase, the leuC subunit of 3-isopropylmalate dehydratase, and the leuD subunit of 3-isopropylmalate dehydratase described herein catalyze various steps in the biosynthesis and utilization of branched chain amino acids. Accordingly, inhibition of the activity of one or more of the enzymes described herein could lead to inhibition plant growth. Thus, the instant dihydroxyacid dehydratase, branched chain amino acid aminotransferase, leuC subunit of 3-isopropylmalate dehydratase, and leuD subunit of 3-isopropylmalate dehydratase could be appropriate for new herbicide discovery and design.

All or a substantial portion of the nucleic acid fragments of the instant invention may also be used as probes for genetically and physically mapping the genes that they are a part of, and as markers for traits linked to those genes. Such information may be useful in plant breeding in order to develop lines with desired phenotypes. For example, the instant nucleic acid fragments may be used as restriction fragment length polymorphism (RFLP) markers. Southern blots (Maniatis) of restriction-digested plant genomic DNA may be probed with the nucleic acid fragments of the instant invention. The resulting banding patterns may then be subjected to genetic analyses using computer programs such as MapMaker (Lander et at., (1987) *Genomics* 1:174–181) in order to construct a genetic map. In addition, the nucleic acid fragments of the instant invention may be used to probe Southern blots containing restriction endonuclease-treated genomic DNAs of a set of individuals representing parent and progeny of a defined genetic cross. Segregation of the DNA polymorphisms is noted and used to calculate the position of the instant nucleic acid sequence in the genetic map previously obtained using this population (Botstein, D. et al., (1980) *Am. J. Hum. Genet.* 32:314–331).

The production and use of plant gene-derived probes for use in genetic mapping is described in R. Bernatzky, R. and Tanksley, S. D. (1986) *Plant Mol. Biol. Reporter* 4(1):37–41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

Nucleic acid probes derived from the instant nucleic acid sequences may also be used for physical mapping (i.e., placement of sequences on physical maps; see Hoheisel, J. D., et al., In: *Nonmammalian Genomic Analysis: A Practical Guide,* Academic press 1996, pp. 319–346, and references cited therein).

In another embodiment, nucleic acid probes derived from the instant nucleic acid sequences may be used in direct fluorescence in situ hybridization (FISH) mapping (Trask, B. J. (1991) *Trends Genet.* 7:149–154). Although current methods of FISH mapping favor use of large clones (several to several hundred KB; see Laan, M. et al. (1995) *Genome Research* 5:13–20), improvements in sensitivity may allow performance of FISH mapping using shorter probes.

A variety of nucleic acid amplification-based methods of genetic and physical mapping may be carried out using the instant nucleic acid sequences. Examples include allele-specific amplification (Kazazian, H. H. (1989) *J. Lab. Clin. Med.* 114(2):95–96), polymorphism of PCR-amplified fragments (CAPS; Sheffield, V. C. et al. (1993) *Genomics* 16:325–332), allele-specific ligation (Landegren, U. et al. (1988) *Science* 241:1077–1080), nucleotide extension reactions (Sokolov, B. P. (1990) *Nucleic Acid Res.* 18:3671), Radiation Hybrid Mapping (Walter, M. A. et al. (1997) *Nature Genetics* 7:22–28) and Happy Mapping (Dear, P. H. and Cook, P. R. (1989) *Nucleic Acid Res.* 1 7:6795–6807). For these methods, the sequence of a nucleic acid fragment is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

Loss of function mutant phenotypes may be identified for the instant cDNA clones either by targeted gene disruption protocols or by identifying specific mutants for these genes contained in a maize population carrying mutations in all possible genes (Ballinger and Benzer, (1989) *Proc. Natl. Acad. Sci USA* 86:9402; Koes et al., (1995) *Proc. Natl. Acad. Sci USA* 92:8149; Bensen et al., (1995) *Plant Cell* 7:75). The latter approach may be accomplished in two ways. First, short segments of the instant nucleic acid fragments may be used in polymerase chain reaction protocols in conjunction with a mutation tag sequence primer on DNAs prepared from a population of plants in which Mutator transposons or some other mutation-causing DNA element has been introduced (see Bensen, supra). The amplification of a specific DNA fragment with these primers indicates the insertion of the mutation tag element in or near the plant gene encoding the dihydroxyacid dehydratase, the branched chain amino acid aminotransferase, the leuC subunit of 3-isopropylmalate dehydratase, or the leuD subunit of 3-isopropylmalate dehydratase. Alternatively, the instant nucleic acid fragment may be used as a hybridization probe against PCR amplification products generated from the mutation population using the mutation tag sequence primer in conjunction with an arbitrary genomic site primer, such as that for a restriction enzyme site-anchored synthetic adaptor. With either method, a plant containing a mutation in the endogenous gene encoding a dihydroxyacid dehydratase, a branched chain amino acid aminotransferase, a leuC subunit of 3-isopropylmalate dehydratase, or a leuD subunit of 3-isopropylmalate dehydratase can be identified and obtained. This mutant plant can then be used to determine or confirm the natural function of the dihydroxyacid dehydratase, the branched chain amino acid aminotransferase, the leuC subunit of 3-isopropylmalate dehydratase, or the leuD subunit of 3-isopropylmalate dehydratase gene product.

EXAMPLES

The present invention is further defined in the following Examples, in which all parts and percentages are by weight and degrees are Celsius, unless otherwise stated. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

Example 1

Composition of cDNA Libraries; Isolation and Sequencing of cDNA Clones cDNA libraries representing mRNAs from various corn, rice, soybean, and wheat tissues were prepared. The characteristics of the libraries are described below.

TABLE 2 cDNA Libraries from Corn, Rice, Soybean, and Wheat

| Library | Tissue | Clone |
|---|---|---|
| cc71se-b | Corn Callus Type II Tissue, Somatic Embryo Formed | cc71se-b.pk0008.b5 |
| cco1 | Corn Cob of 67 Day Old Plants Grown in Green House | cco1.pk0030.d2 |
| cen1 | Corn Endosperm 10 to 11 Days After Pollination | cen1.pk0032.b1 |
| cen3n | Corn Endosperm 20 Days After Pollination* | cen3n.pk0015.g3 cen3n.pk0060.h4 cen3n.pk0121.h11 |
| cen6 | Corn Developing Embryo 40 Days After Pollination | cen6.pk0003.b5 |
| cr1 | Corn Root From 7 Day Old Seedlings | cr1.pk0032.c4 |
| cr1n | Corn Root From 7 Day Old Seedlings* | cr1n.pk0123.b7 cr1n.pk0153.e9 |
| cta1n | Corn Tassel* | cta1n.pk0070.e7 cta1n.pk0077.c7 |
| rl0n | Rice 15 Day Old Leaf* | rl0n.pk087.k16 |
| rls12 | Rice Leaf 15 Days After Germination, 12 hours after infection of strain *Magaporthe grisea* 4360-R-67 (AVR2-YAMO); Susceptible | rls12.pk0001.c2 |
| rls24 | Rice Leaf 15 Days After Germination, 24 Hours After Infection of Strain *Magaporthe grisea* 4360-R-67 (AVR2-YAMO); Susceptible | rls24.pk0025.f6 |
| rls72 | Rice Leaf 15 Days After Germination, 72 Hours After Infection of Strain *Magaporthe grisea* 4360-R-67 (AVR2-YAMO); Susceptible | rls72.pk0014.a3 |
| sdp3c | Soybean Developing Pods (8–9 mm) | sdp3c.pk008.k13 |
| se3 | Soybean Embryo, 17 Days After Flowering | se3.pk0006.g4 |
| ses8w | Soybean Mature Embryo 8 Weeks After Subculture | ses8w.pk0032.e9 |
| ses9c | Soybean Embryogenic Suspension | ses9c.pk001.o8 |
| sre | Soybean Root Elongation Zone 4 to 5 Days After Germination | sre.pk0001.d1 |
| srm | Soybean Root Meristem | srm.pk0006.h5 |
| srr1c | Soybean 8-Day-Old Root | srr1c.pk003.c2 |
| srr2c | Soybean 8-Day-Old Root | srr2c.pk003.d20 |
| wkm1c | Wheat Kernel Malted 55 Hours at 22 Degrees Celsius | wkm1c.pk0004.c7 |
| wkm2c | Wheat Kernel Malted 175 Hours at 4 Degrees Celsius | wkm2c.pk005.c12 |
| wl1n | Wheat Leaf From 7 Day Old Seedling* | wl1n.pk0048.a6 wl1n.pk0123.c11 |

TABLE 2-continued cDNA Libraries from Corn, Rice, Soybean, and Wheat

| Library | Tissue | Clone |
|---|---|---|
| wlm96 | Wheat Seedlings 96 Hours After Inoculation With *Erysiphe graminis f. sp tritici* | wlm96.pk027.n2 |
| wre1n | Wheat Root From 7 Day Old Etiolated Seedling* | wre1n.pk0045.b10 |

*These libraries were normalized essentially as described in U.S. Pat. No. 5,482,845, incorporated herein by reference cDNA libraries were prepared in Uni-ZAP™ XR vectors according to the manufacturer's protocol (Stratagene Cloning Systems, La Jolla, Calif.). Conversion of the Uni-ZAP™ XR libraries into plasmid libraries was accomplished according to the protocol provided by Stratagene. Upon conversion, cDNA inserts were contained in the plasmid vector pBluescript. cDNA inserts from randomly picked bacterial colonies containing recombinant pBluescript plasmids were amplified via polymerase chain reaction using primers specific for vector sequences flanking the inserted cDNA sequences or plasmid DNA was prepared from cultured bacterial cells. Amplified insert DNAs or plasmid DNAs were sequenced in dye-primer sequencing reactions to generate partial cDNA sequences (expressed sequence tags or "ESTs"; see Adams, M. D. et al., (1991) *Science* 252:1651). The resulting ESTs were analyzed using a Perkin Elmer Model 377 fluorescent sequencer.

Example 2

Identification of cDNA Clones

ESTs encoding branched chain biosynthetic enzymes were identified by conducting BLAST (Basic Local Alignment Search Tool; Altschul, S. F., et al., (1993) *J. Mol. Biol.* 215:403–410; see also www.ncbi.nlm.nih.gov/BLAST/) searches for similarity to sequences contained in the BLAST "nr" database (comprising all non-redundant GenBank CDS translations, sequences derived from the 3-dimensional structure Brookhaven Protein Data Bank, the last major release of the SWISS-PROT protein sequence database, EMBL, and DDBJ databases). The cDNA sequences obtained in Example 1 were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D. J. (1993) *Nature Genetics* 3:266–272) provided by the NCBI. For convenience, the P-value (probability) of observing a match of a cDNA sequence to a sequence contained in the searched databases merely by chance as calculated by BLAST are reported herein as "pLog" values, which represent the negative of the logarithm of the reported P-value. Accordingly, the greater the pLog value, the greater the likelihood that the cDNA sequence and the BLAST "hit" represent homologous proteins.

Example 3

Characterization of cDNA Clones Encoding Dihydroxyacid Dehydratase

The BLASTX search using the nucleotide sequences from clones se3.pk0006.g4, ses4d.pk0014.h5, ssl.pk0021.g5, sre.pk0012.h2, ses8w.pk0010.e5, se4.03a05, ssm.pk0004.h12, ssm.pk0033.d5, cr1.pk0032.c4, cen1.pk0015.f5, cen3n.pk0071.h6, cen3n.pk0031.g9 and wre1n.pk0007.a4 revealed similarity of the proteins encoded by the cDNAs to dihydroxyacid dehydratases from several organisms, including *Lactococcus lactis* (SWISS-PROT Accession No. Q02139, NCBI gi Accession No. 400054) and *Saccharomyces cerevisiae* (SWISS-PROT Accession No. P39522, NCBI gi Accession No. 1170543). The BLAST results for each of these ESTs are shown in Table 3:

TABLE 3

BLAST Results for Clones Encoding Polypeptides Homologous to Dihydroxyacid Dehydratases

| | BLAST pLog Score | |
|---|---|---|
| Clone | Q02139 (*Lactococcus lactis*) | P39522 (*Saccharomyces cerevisiae*) |
| cen1.pk0015.f5 | 41.03 | 21.43 |
| cen3n.pk0031.g9 | 38.89 | 40.35 |
| cen3n.pk0071.h6 | 32.62 | 34.55 |
| cr1.pk0032.c4 | 5.64 | 8.33 |
| se3.pk0006.g4 | 26.64 | 37.80 |
| se4.03a05 | 12.41 | 19.03 |
| ses4d.pk0014.h5 | 4.89 | na* |
| ses8w.pk0010.e5 | 37.34 | 33.74 |
| sre.pk0012.h2 | 41.54 | 37.96 |
| ssl.pk0021.g5 | 38.66 | 33.92 |
| ssm.pk0004.h12 | 5.74 | 10.82 |
| ssm.pk0033.d5 | 23.30 | 28.59 |
| wre1n.pk0007.a4 | 6.39 | 7.29 | na* = no data available

The sequence of the entire cDNA insert in clone cr1.pk0032.c4 was determined and is shown in SEQ ID NO:1. This sequence encodes a full-length dihydroxyacid dehydratase, and includes the sequences from clones cen1.pk0015.f5, cen3n.pk0031.g9, and cen3n.pk0071.h6. The deduced amino acid sequence of this cDNA is shown in SEQ ID NO:2. The amino acid sequence set forth in SEQ ID NO:2 was evaluated by BLASTP, yielding a pLog value larger than 254 versus the *Saccharomyces cerevisiae* sequence.

A sequence encoding a full-length dihydroxyacid dehydratase was formed by assembling a contig with the nucleotides of the entire cDNA insert in clone se3.pk0006.g4 and a portion of the cDNA insert from clone ses9c.pk001.o8. This sequence includes the nucleotide sequences from clones se4.03a05, ses4d.pk0014.h5, ses8w.pk0010.e5, sre.pk0012.h2, ssl.pk0021.g5, and ssm.pk0004.h12. The nucleotide sequence of this contig is shown in SEQ ID NO:3; the deduced amino acid sequence of this cDNA is shown in SEQ ID NO:4. The amino acid sequence set forth in SEQ ID NO:4 was evaluated by BLASTP, yielding a pLog value larger than 254 versus the *Saccharomyces cerevisiae* sequence.

The sequence of a portion of the cDNA insert from clone wkm2c.pk005.c12 was determined and found to contain the sequence from clone wre1n.pk0007.a4. The BLASTX search using the nucleotide sequence from clone wkm2c.pk005.c12 resulted in a pLog value of 49 against the *Saccharomyces cerevisiae* dihydroxyacid dehydratase and a pLog value of 47 against the *Lactococcus lactis* sequence. The sequence for clone wkm2c.pk005.c12 is shown in SEQ ID NO:5; the deduced amino acid sequence of this cDNA is shown in SEQ ID NO:6.

FIG. 2 presents an alignment of the amino acid sequences set forth in SEQ ID NOs:2, 4, and 6 and the *Saccharomyces* cerevisiae sequence (SEQ ID NO:7). The data in Table 4 represents a calculation of the percent identity of the amino acid sequences set forth in SEQ ID NOs:2, 4, and 6 and the *Saccharomyces cerevisiae* dihydroxyacid dehydratase sequence.

TABLE 4

Percent Identity of Amino Acid Sequences Deduced From the Nucleotide Sequences of cDNA Clones Encoding Polypeptides Homologous to Dihydroxyacid Dehydratase

| Clone | SEQ ID NO. | Percent Identity to NCBI gi Accession No. 1170543 (*Saccharomyces cerevisiae*) |
|---|---|---|
| cr1.pk0032.c4 | 2 | 58.5 |
| Contig of: | 4 | 58.8 |
| se3.pk0006.g4 | | |
| ses9c.pk001.o8 | | |
| wkm2c.pk005.c12 | 6 | 55.8 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151–153) using the default parameters (GAP PENALTY=10, GAP LENGHT PENALTY=10). Sequence percent identity calculations were performed by the Jotun Hein method (Hein. J. J. (1990) *Meth. Enz.* 183:626–645). Sequence alignments and BLAST scores and probabilities indicate that the instant nucleic acid fragments encode entire corn and soybean dihydroxyacid dehydratase and a portion of a wheat dihydroxyacid dehydratase. These sequences represent the first plant sequences encoding a dihydroxyacid dehydratase enzyme.

Example 4

Characterization of cDNA Clones Encoding Branched-Chain Amino Acid Aminotransferases The BLASTX search using the nucleotide sequences of clones ses8w.pk0032.e9, cco1.pk0030.d2 and cen6.pk0003.b5 revealed similarity of the proteins encoded by the cDNAs to putative branched chain amino acid aminotransferases from *Bacillus subtilis* (SWISS-PROT Accession No. P39576, NCBI gi Accession No. 1176947) and *Mycobacterium tuberculosis* (SWISS-PROT Accession No. Q10399, NCBI gi Accession No. 1708468). A further BLASTX search using the nucleotide sequences from clones cc71se-b.pk0008.b5, cta1n.pk0070.e7, rls24.pk0025.f6, and wlm96.pk027.n2 also revealed similarity of the proteins encoded by the cDNAs to putative branched chain amino acid aminotransferases from *Bacillus subtilis* and *Mycobacterium tuberculosis*. The BLASTX search using the nucleotide sequences from clones rls72.pk0014.a3, sre.pk0001.d1, srr2c.pk003.d20, and wl1n.pk0123.c11 revealed similarity of the proteins encoded by the cDNAs to putative branched chain amino acid aminotransferase from *Methanococcus jannaschii* (NCBI gi Accession No. 3122287). The BLASTX search using the nucleotide sequences from clones cco1.pk0030.d2, and wkm1c.pk0004.c7 revealed similarity of the proteins encoded by the cDNAs to branched chain amino acid aminotransferase from *Escherichia coli* (NCBI gi Accession No. 124380). The BLASTX results for each of these sequences are shown in Table 5:

TABLE 5

BLASTX Results for Clones Encoding Polypeptides Homologous to Branched-Chain Amino Acid Aminotransferases

| Clone | Accession No. | BLAST pLog Score | Accession No. | BLAST pLog Score |
|---|---|---|---|---|
| cc71se-b.pk0008.b5 | 1176947 | 16.22 | 1708468 | 18.10 |
| cen6.pk0003.b5 | 1176947 | 50.40 | 1708468 | 34.30 |
| cta1n.pk0070.e7 | 1176947 | 12.00 | 1708468 | 10.50 |
| rls24.pk0025.f6 | 1176947 | 66.00 | 1708468 | 56.70 |
| ses8w.pk0032.e9 | 1176947 | 41.70 | 1708468 | 39.70 |
| wlm96.pk027.n2 | 1176947 | 88.40 | 1708468 | 67.00 |
| rls72.pk0014.a3 | 3122287 | 9.00 | | |
| sre.pk0001.d1 | 3122287 | 24.00 | | |
| srr2c.pk003.d20 | 3122287 | 21.70 | | |
| wl1n.pk0123.c11 | 3122287 | 9.40 | | |
| cco1.pk0030.d2 | 124380 | 26.70 | | |
| wkm1c.pk0004.c7 | 124380 | 19.05 | | |

The sequence of a portion of the cDNA insert in clone cc71se-b.pk0008.b5 was determined and is shown in SEQ ID NO:8; the deduced amino acid sequence of this cDNA is shown in SEQ ID NO:9. The sequence of the entire cDNA insert in clone cen6.pk0003.b5 was determined and is shown in SEQ ID NO:10; the deduced amino acid sequence of this cDNA is shown in SEQ ID NO:11. The sequence of a portion of the cDNA insert in clone cta1n.pk0070.e7 was determined and is shown in SEQ ID NO:12; the deduced amino acid sequence of this cDNA is shown in SEQ ID NO:13. The sequence of the entire cDNA insert in clone rls24.pk0025.f6 was determined and is shown in SEQ ID NO:14; the deduced amino acid sequence of this cDNA is shown in SEQ ID NO:15. The sequence of the entire cDNA insert in clone ses8w.pk0032.e9 was determined and is shown in SEQ ID NO:16; the deduced amino acid sequence of this cDNA is shown in SEQ ID NO:17. The sequence of the entire cDNA insert in clone wlm96.pk027.n2 was determined and is shown in SEQ ID NO:18; the deduced amino acid sequence of this cDNA is shown in SEQ ID NO:19. The amino acid sequences set forth in SEQ ID NO:11, SEQ ID NO:15, SEQ ID NO:17, and SEQ ID NO:19 were evaluated by BLASTP revealing similarity to the branched-chain amino acid aminotransferase from *Bacillus subtilis* (NCBI gi Accession No. 1176947); the results of these analyses are shown in Table 6. FIG. 3 presents an alignment of the amino acid sequences set forth in SEQ ID NOs:9, 11, 13, 15, 17, and 19 and the *Bacillus subtilis* sequence (SEQ ID NO:20).

The sequence of the entire cDNA insert in clone rls72.pk0014.a3 was determined and is shown in SEQ ID NO:21; the deduced amino acid sequence of this cDNA is shown in SEQ ID NO:22. The sequence of the entire cDNA insert in clone sre.pk0001.d1 was determined and is shown in SEQ ID NO:23; the deduced amino acid sequence of this cDNA is shown in SEQ ID NO:24. The sequence of the entire cDNA insert in clone srr2c.pk003.d20 was determined and is shown in SEQ ID NO:25; the deduced amino acid sequence of this cDNA is shown in SEQ ID NO:26. The sequence of the entire cDNA insert in clone wl1n.pk0123.c11 was determined and is shown in SEQ ID NO:27; the deduced amino acid sequence of this cDNA is shown in SEQ ID NO:28. The amino acid sequences set forth in SEQ ID NO:22, SEQ ID NO:24, SEQ ID NO:26, and SEQ ID NO:28, were evaluated by BLASTP revealing similarity to the branched-chain amino acid aminotransferase from *Methanococcus jannaschii* (NCBI gi Accession No. 3122287), the results of these analyses are shown in Table 6. FIG. 4 presents an alignment of the amino acid sequences set forth in SEQ ID NOs:22, 24, 26, and 28 and the *Methanococcus jannaschii* sequence (SEQ ID NO:29).

The sequence of the entire cDNA insert in clone cco1.pk0030.d2 was determined and is shown in SEQ ID NO:30; the deduced amino acid sequence of this cDNA is shown in SEQ ID NO:31. The sequence of the entire cDNA insert in clone wkm1c.pk0004.c7 was determined and is shown in SEQ ID NO:32; the deduced amino acid sequence of this cDNA is shown in SEQ ID NO:33. The amino acid sequences set forth in SEQ ID NO:31, and SEQ ID NO:33 were evaluated by BLASTP revealing similarity to the branched-chain amino acid aminotransferase from *Escherichia coli* (NCBI gi Accession No. 124380), the results of these analyses are shown in Table 6. FIG. 5 presents an alignment of the amino acid sequences set forth in SEQ ID NOs:31, and 33 and the *Escherichia coli* sequence (SEQ ID NO:34).

TABLE 6

BLASTP Results for Clones Encoding Polypeptides Homologous to Branched-Chain Amino Acid Aminotransferases

| Clone | Accession No. | BLASTP pLog Score |
|---|---|---|
| cen6.pk0003.b5 | 1176947 | 45.00 |
| rls24.pk0025.f6 | 1176947 | 63.00 |
| ses8w.pk0032.e9 | 1176947 | 35.00 |
| wlm96.pk027.n2 | 1176947 | 77.22 |
| rls72.pk0014.a3 | 3122287 | 11.70 |
| sre.pk0001.d1 | 3122287 | 24.22 |
| srr2c.pk003.d20 | 3122287 | 22.52 |
| wl1n.pk0123.c11 | 3122287 | 12.40 |
| cco1.pk0030.d2 | 124380 | 31.00 |
| wkm1c.pk0004.c7 | 124380 | 21.00 |

The data in Table 7 represents a calculation of the percent identity of the amino acid sequences set forth in SEQ ID NOs:9, 11, 13, 15, 17, and 19 and the *Bacillus subtilis* sequence; a percent identity of the amino acid sequences set forth in SEQ ID NOs:22, 24, 26, and 28 and the *Methanococcus jannaschii* sequence; and a percent identity of the amino acid sequences set forth in SEQ ID NOs:3 1, and 33 and the *Escherichia coli* sequence.

TABLE 7

Percent Identity of Amino Acid Sequences Deduced From the Nucleotide Sequences of cDNA Clones Encoding Polypeptides Homologous to Branched-Chain Amino Acid Aminotransferases

| Clone | SEQ ID NO. | Accession No. | Percent Identity |
|---|---|---|---|
| cc71se-b.pk0008.b5 | 9 | 1176947 | 11.3 |
| cen6.pk0003.b5 | 11 | 1176947 | 45.2 |
| cta1n.pk0070.e7 | 13 | 1176947 | 41.1 |
| rls24.pk0025.f6 | 15 | 1176947 | 40.6 |
| ses8w.pk0032.e9 | 17 | 1176947 | 12.2 |
| wlm96.pk027.n2 | 19 | 1176947 | 44.7 |
| rls72.pk0014.a3 | 22 | 3122287 | 25.5 |
| sre.pk0001.d1 | 24 | 3122287 | 30.7 |
| srr2c.pk003.d20 | 26 | 3122287 | 26.3 |
| wl1n.pk0123.c11 | 28 | 3122287 | 30.6 |
| cco1.pk0030.d2 | 31 | 124380 | 32.7 |
| wkm1c.pk0004.c7 | 33 | 124380 | 30.8 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS*. 5:151–153) using the default parameters (GAP PENALTY=10, GAP LENGHT PENALTY=10). Sequence percent identity calculations were performed by the Jotun Hein method (Hein. J. J. (1990) *Meth. Enz.* 183:626–645).

Sequence alignments and BLAST scores and probabilities indicate that the instant nucleic acid fragments encode three distinct classes of branched-chain amino acid aminotransferases. Fragments from corn, rice, soybean, and wheat are similar to the *Bacillus subtilis* putative branched-chain amino acid aminotransferase, full-length soybean, and fragments from rice, and wheat similar to the *Methanococcus jannaschii* enzyme, and a full-length corn, and most of a wheat branched chain amino acid aminotransferase similar to the *Escherichia coli* enzyme. These sequences represent the first plant sequences encoding branched-chain amino acid aminotransferase enzymes.

Example 5

Characterization of cDNA Clones Encoding Large Subunit of 3-Isopropylmalate Dehydratase The BLASTX search using the nucleotide sequences from clones srm.pk0006.h5, ceb3.pk0001.b5, cen1.pk0032.b1, cen3n.pk0015.g3 and cen3n.pk0060.h4 revealed similarity of the proteins encoded by the cDNAs to the large subunit of 3-isopropylmalate dehydratase, which is encoded by the gene designated leuC in *E. coli* and *Salmonella typhumurium*. Similarity of the proteins is greatest to enzymes encoded by GenBank Accession No. U67499 and GenBank Accession No. U67543 from *Methanococcus jannaschii* (NCBI gi Accession No. 3219823, and 3122347, respectively). Both of these GenBank Accessions show strong similarity to the leuC subunit of 3-isopropylmalate dehydratase, but have been mis-labelled as aconitase and homoaconitase. Neither aconitase nor homoaconitase are expected to be present in *Methanococcus jannaschii* (see Selkov et al. (1997) *Gene* 197:GC1 1-GC26; this paper can be accessed via the World Wide Web at http://www.cme.msu.edu/wit/Doc/mj_recon.html). The BLAST results for each of these ESTs are shown in Table 8:

TABLE 8

BLAST Results for Clones Encoding Polypeptides Homologous to the leuC Protein Subunit of 3-Isopropylmalate Dehydratase Enzymes

| | BLAST pLog Score | |
|---|---|---|
| Clone | U67499 | U67543 |
| srm.pk0006.h5 | 6.92 | 8.80 |
| ceb3.pk0001.b5 | 52.08 | 23.68 |
| cen1.pk0032.b1 | 44.89 | 43.01 |
| cen3n.pk0015.g3 | 12.24 | 11.92 |
| cen3n.pk0060.h4 | 14.17 | 14.74 |

The BLASTX search using the nucleotide sequences from the contig assembled of clones cen1.pk0032.b1, cta1n.pk0077.c7, cen3n.pk0015.g3, cen3n.pk0060.h4, and cen3n.pk0121.h11 (the clone ceb3.pk0001.b5 is included in the contig), the nucleotide sequences from clones cr1n.pk0153.e9, r10n.pk087.k16, and wre1n.pk0045.b10, and the nucleotide sequences from the contig assembled of clones sdp3c.pk008.k13 and srm.pk0006.h5 revealed similarity of the same proteins. The BLAST results for each of these sequences are shown in Table 9:

TABLE 9

BLAST Results for Clones Encoding Polypeptides Homologous
to the leuC Protein Subunit of 3-Isopropylmalate
Dehydratase Enzymes

| | BLASTX pLog Score | |
|---|---|---|
| Clone | NCBI gi Accession No. 3219823 | NCBI gi Accession No. 3122347 |
| Contig of: | 91.22 | 66.30 |
| cen1.pk0032.b1 | | |
| cta1n.pk0077.c7 | | |
| cen3n.pk0015.g3 | | |
| cen3n.pk0060.h4 | | |
| cen3n.pk0121.h11 | | |
| cr1n.pk0153.e9 | 94.22 | 69.22 |
| rl0n.pk087.k16 | 44.00 | 27.40 |
| Contig of: | 28.15 | 25.40 |
| sdp3c.pk008.k13 | | |
| srm.pk0006.h5 | | |
| wre1n.pk0045.b10 | 12.00 | 11.52 |

The sequence of the contig assembled of the cDNA insert in clones cen1.pk0032.b1, cta1n.pk0077.c7, cen3n.pk0015.g3, cen3n.pk0060.h4, and cen3n.pk0121.h11 was determined and is shown in SEQ ID NO:35; the deduced amino acid sequence of this cDNA is shown in SEQ ID NO:36. The amino acid sequence set forth in SEQ ID NO:36 was evaluated by BLASTP, yielding a pLog value of 93.00 versus the *Methanococcus jannaschii* sequence (NCBI gi Accession No. 3219823). The sequence of the entire cDNA insert in clone cr1n.pk0153.e9 was determined and is shown in SEQ ID NO:37; the deduced amino acid sequence of this cDNA is shown in SEQ ID NO:38. The amino acid sequence set forth in SEQ ID NO:38 was evaluated by BLASTP, yielding a pLog value of 91.00 versus the *Methanococcus jannaschii* sequence (NCBI gi Accession No. 3219823). The sequence of a portion of the cDNA insert in clone r10n.pk087.k16 was determined and is shown in SEQ ID NO:39; the deduced amino acid sequence of this cDNA is shown in SEQ ID NO:40. The sequence of the contig assembled of the cDNA insert in clones sdp3c.pk008.k13 and srm.pk0006.h5 was determined and is shown in SEQ ID NO:41; the deduced amino acid sequence of this cDNA is shown in SEQ ID NO:42. The sequence of a portion of the cDNA insert in clone wre1n.pk0045.b10 was determined and is shown in SEQ ID NO:43; the deduced amino acid sequence of this cDNA is shown in SEQ ID NO:44.

FIG. 6 presents an alignment of the amino acid sequences set forth in SEQ ID NOs:36, 38, 40, 42, and 44 and the *Methanococcus jannaschii* sequence (SEQ ID NO:45). The data in Table 10 represents a calculation of the percent identity of the amino acid sequences set forth in SEQ ID NOs:36, 38, 40, 42, and 44 and the *Methanococcus jannaschii* sequence.

TABLE 10

Percent Identity of Amino Acid Sequences Deduced From the
Nucleotide Sequences of cDNA Clones Encoding Polypeptides
Homologous to the leuC Protein Subunit of
3-Isopropylmalate Dehydratase Enzymes

| Clone | SEQ ID NO. | Percent Identity to NCBI gi Accession No. 3219823 |
|---|---|---|
| Contig of: | 36 | 45.8 |
| cen1.pk0032.b1 | | |
| cta1n.pk0077.c7 | | |
| cen3n.pk0015.g3 | | |
| cen3n.pk0060.h4 | | |
| cen3n.pk0121.h11 | | |
| cr1n.pk0153.e9 | 38 | 45.6 |
| rl0n.pk087.k16 | 40 | 55.5 |
| Contig of: | 42 | 15.4 |
| sdp3c.pk008.k13 | | |
| srm.pk0006.h5 | | |
| wre1n.pk0045.b10 | 44 | 16.5 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS.* 5:151–153) using the default parameters (GAP PENALTY=10, GAP LENGHT PENALTY=10). Sequence percent identity calculations were performed by the Jotun Hein method (Hein, J. J. (1990) *Meth. Enz.* 183:626–645).

Sequence alignments and BLAST scores and probabilities indicate that the instant nucleic acid fragments encode two distinct entire corn the leuC subunit of 3-isopropylmalate dehydratases, a central fragment of a rice leuC subunit of 3-isopropylmalate dehydratase, and the C-terminal half of a soybean, and a wheat leuC subunit of 3-isopropylmalate dehydratase. These sequences represent the first plant sequences encoding leuC subunit of 3-isopropylmalate dehydratase enzyme.

Example 6

Characterization of cDNA Clones Encoding the leuD Subunit of 3-Isopropylmalate Dehydratase The BLASTX search using the nucleotide sequences from EST clones cr1n.pk0123.b7 and rls12.pk0001.c2 revealed similarity of the proteins encoded by the cDNAs to the small subunit of 3-isopropylmalate dehydratase enzymes from several organisms, including *Methanococcus jannaschii* (GenBank Accession No. U67568) and *Lactococcus lactis* (SWISS-PROT Accession No. Q02144). This subunit is encoded by the gene designated leuD in *E. coli* and *Salmonella typhimurium*. The BLAST results for each of these ESTs are shown in Table 11:

TABLE 11

BLAST Results for Clones Encoding Polypeptides Homologous
to the leuD Protein Subunit of 3-Isopropylmalate
Dehydratase Enzymes

| | BLAST pLog Score | |
|---|---|---|
| Clone | U67568 | Q02144 |
| cr1n.pk0123.b7 | 3.70 | 1.80 |
| rls12.pk0001.c2 | 5.14 | 3.96 |

The BLASTX search using the nucleotide sequences of the entire insert from clones cr1n.pk0123.b7, rls12.pk0001.c2, srr1c.pk003.c2, and w1n.pk0048.a6 also revealed similarity of the proteins encoded by the cDNAs to the small subunit of 3-isopropylmalate dehydratase enzymes from several organisms, including *Methanococcus jannaschii* (NCBI gi Accession No. 3122345) and *Lactococcus lactis* (NCBI gi Accession No. 400187). The BLAST results for each of these sequences are shown in Table 12:

TABLE 12

BLAST Results for Clones Encoding Polypeptides Homologous to the leuD Protein Subunit of 3-Isopropylmalate Dehydratase Enzymes

| | BLAST pLog Score | |
|---|---|---|
| Clone | NCBI gi Accession No. 3122345 | NCBI gi Accession No. 400187 |
| cr1n.pk0123.b7 | 16.70 | 12.30 |
| rls12.pk0001.c2 | 16.40 | 11.30 |
| srr1c.pk003.c2 | 18.70 | 11.52 |
| w1n.pk0048.a6 | 17.05 | 12.22 |

The sequence of the entire cDNA insert in clone cr1n.pk0123.b7 was determined and is shown in SEQ ID NO:46; the deduced amino acid sequence of this cDNA is shown in SEQ ID NO:47. The sequence of the entire cDNA insert in clone rls12.pk0001.c2 was determined and is shown in SEQ ID NO:48; the deduced amino acid sequence of this cDNA is shown in SEQ ID NO:49. The sequence of the entire cDNA insert in clone srr1c.pk003.c2 was determined and is shown in SEQ ID NO:50; the deduced amino acid sequence of this cDNA is shown in SEQ ID NO:51. The sequence of the entire cDNA insert in clone w11n.pk0048.a6 was determined and is shown in SEQ ID NO:52 the deduced amino acid sequence of this cDNA is shown in SEQ ID NO:53. The amino acid sequences set forth in SEQ ID NOs:47, 49, 51, and 53 were evaluated by BLASTP, yielding the pLog values shown in Table 13 versus the *Methanococcus jannaschii* (NCBI gi Accession No. 3122345) and *Lactococcus lactis* (NCBI gi Accession No. 400187) sequences.

TABLE 13

BLASTP Results for Clones Encoding Polypeptides Homologous to the leuD Protein Subunit of 3-Isopropylmalate Dehydratase Enzymes

| | BLASTP pLog Score | |
|---|---|---|
| Clone | NCBI gi Accession No. 3122345 | NCBI gi Accession No. 400187 |
| cr1n.pk0123.b7 | 16.70 | 12.30 |
| rls12.pk0001.c2 | 16.40 | 11.30 |
| srr1c.pk003.c2 | 18.70 | 11.52 |
| w1n.pk0048.a6 | 17.05 | 12.22 |

FIG. 7 presents an alignment of the amino acid sequences set forth in SEQ ID NOs:47, 49, 51, and 53 and the *Lactococcus lactis* sequence (SEQ ID NO:54). The data in Table 14 represents a calculation of the percent identity of the amino acid sequences set forth in SEQ ID NOs:47, 49, 51, and 53 and the *Lactococcus lactis* sequence.

TABLE 14

Percent Identity of Amino Acid Sequences Deduced From the Nucleotide Sequences of cDNA Clones Encoding Polypeptides Homologous to the leuD Protein Subunit of 3-Isopropylmalate Dehydratase Enzymes

| Clone | SEQ ID NO. | Percent Identity to 400187 |
|---|---|---|
| cr1n.pk0123.b7 | 47 | 35.8 |
| rls12.pk0001.c2 | 49 | 34.5 |
| srr1c.pk003.c2 | 51 | 38.0 |
| w11n.pk0048.a6 | 53 | 36.0 |

Sequence alignments and percent identity calculations were performed using the Megalign program of the LASARGENE bioinformatics computing suite (DNASTAR Inc., Madison, Wis.). Multiple alignment of the sequences was performed using the Clustal method of alignment (Higgins, D. G. and Sharp, P. M. (1989) *CABIOS.* 5:151–153) using the default parameters (GAP PENALTY=10, GAP LENGHT PENALTY=10). Sequence percent identity calculations were performed by the Jotun Hein method (Hein, J. J. (1990) *Meth. Enz.* 183:626–645).

Sequence alignments and BLAST scores and probabilities indicate that the instant nucleic acid fragments encode entire corn, rice, soybean, and wheat leuD protein subunit of 3-isopropylmalate dehydratase enzymes. These sequences represent the first plant sequences encoding leuD protein subunit of 3-isopropylmalate dehydratase.

Example 7

Expression of Chimeric Genes in Monocot Cells

A chimeric gene comprising a cDNA encoding a branched-chain biosynthetic enzyme in sense orientation with respect to the maize 27 kD zein promoter that is located 5' to the cDNA fragment, and the 10 kD zein 3' end that is located 3' to the cDNA fragment, can be constructed. The cDNA fragment of this gene may be generated by polymerase chain reaction (PCR) of the cDNA clone using appropriate oligonucleotide primers. Cloning sites (NcoI or SmaI) can be incorporated into the oligonucleotides to provide proper orientation of the DNA fragment when inserted into the digested vector pML103 as described below. Amplification is then performed in a standard PCR. The amplified DNA is then digested with restriction enzymes NcoI and SmaI and fractionated on an agarose gel. The appropriate band can be isolated from the gel and combined with a 4.9 kb NcoI-SmaI fragment of the plasmid pML103. Plasmid pML103 has been deposited under the terms of the Budapest Treaty at ATCC (American Type Culture Collection, 10801 University Blvd., Manassas, Va. 20110-2209), and bears accession number ATCC 97366. The DNA segment from pML103 contains a 1.05 kb SalI-NcoI promoter fragment of the maize 27 kD zein gene and a 0.96 kb SmaI-SalI fragment from the 3' end of the maize 10 kD zein gene in the vector pGem9Zf(+) (Promega). Vector and insert DNA can be ligated at 15° C. overnight, essentially as described (Maniatis). The ligated DNA may then be used to transform *E. coli* XL1-Blue (*Epicurian Coli* XL-1 Blue™; Stratagene). Bacterial transformants can be screened by restriction enzyme digestion of plasmid DNA and limited nucleotide sequence analysis using the dideoxy chain termination method (Sequenase™ DNA Sequencing Kit; U.S. Biochemical). The resulting plasmid construct would comprise a chimeric gene encoding, in the 5' to 3' direction, the maize 27 kD zein promoter, a cDNA fragment encoding a branched-chain biosynthetic enzyme, and the 10 kD zein 3' region.

The chimeric gene described above can then be introduced into corn cells by the following procedure. Immature corn embryos can be dissected from developing caryopses derived from crosses of the inbred corn lines H99 and LH132. The embryos are isolated 10 to 11 days after pollination when they are 1.0 to 1.5 mm long. The embryos are then placed with the axis-side facing down and in contact with agarose-solidified N6 medium (Chu et al., (1975) *Sci. Sin. Peking* 18:659–668). The embryos are kept in the dark at 27° C. Friable embryogenic callus consisting of undifferentiated masses of cells with somatic proembryoids and embryoids borne on suspensor structures proliferates from the scutellum of these immature embryos. The embryogenic callus isolated from the primary explant can be cultured on N6 medium and sub-cultured on this medium every 2 to 3 weeks.

The plasmid, p35S/Ac (obtained from Dr. Peter Eckes, Hoechst Ag, Frankfurt, Germany) may be used in transformation experiments in order to provide for a selectable marker. This plasmid contains the Pat gene (see European Patent Publication 0 242 236) which encodes phosphinothricin acetyl transferase (PAT). The enzyme PAT confers resistance to herbicidal glutamine synthetase inhibitors such as phosphinothricin. The pat gene in p35S/Ac is under the control of the 35S promoter from Cauliflower Mosaic Virus (Odell et al. (1985) *Nature* 313:810–812) and the 3' region of the nopaline synthase gene from the T-DNA of the Ti plasmid of *Agrobacterium tumefaciens*.

The particle bombardment method (Klein et al., (1987) *Nature* 327:70–73) may be used to transfer genes to the callus culture cells. According to this method, gold particles (1 μm in diameter) are coated with DNA using the following technique. Ten μg of plasmid DNAs are added to 50 μL of a suspension of gold particles (60 mg per mL). Calcium chloride (50 μL of a 2.5 M solution) and spermidine free base (20 μL of a 1.0 M solution) are added to the particles. The suspension is vortexed during the addition of these solutions. After 10 minutes, the tubes are briefly centrifuged (5 sec at 15,000 rpm) and the supernatant removed. The particles are resuspended in 200 μL of absolute ethanol, centrifuged again and the supernatant removed. The ethanol rinse is performed again and the particles resuspended in a final volume of 30 μL of ethanol. An aliquot (5 μL) of the DNA-coated gold particles can be placed in the center of a Kapton™ flying disc (Bio-Rad Labs). The particles are then accelerated into the corn tissue with a Biolistic™ PDS-1000/ He (Bio-Rad Instruments, Hercules Calif.), using a helium pressure of 1000 psi, a gap distance of 0.5 cm and a flying distance of 1.0 cm.

For bombardment, the embryogenic tissue is placed on filter paper over agarose-solidified N6 medium. The tissue is arranged as a thin lawn and covered a circular area of about 5 cm in diameter. The petri dish containing the tissue can be placed in the chamber of the PDS-1000/He approximately 8 cm from the stopping screen. The air in the chamber is then evacuated to a vacuum of 28 inches of Hg. The macrocarrier is accelerated with a helium shock wave using a rupture membrane that bursts when the He pressure in the shock tube reaches 1000 psi.

Seven days after bombardment the tissue can be transferred to N6 medium that contains gluphosinate (2 mg per liter) and lacks casein or proline. The tissue continues to grow slowly on this medium. After an additional 2 weeks the tissue can be transferred to fresh N6 medium containing gluphosinate. After 6 weeks, areas of about 1 cm in diameter of actively growing callus can be identified on some of the plates containing the gluphosinate-supplemented medium. These calli may continue to grow when sub-cultured on the selective medium.

Plants can be regenerated from the transgenic callus by first transferring clusters of tissue to N6 medium supplemented with 0.2 mg per liter of 2,4-D. After two weeks the tissue can be transferred to regeneration medium (Fromm et al., (1990) *Bio/Technology* 8:833–839).

Example 8

Expression of Chimeric Genes in Dicot Cells

A seed-specific expression cassette composed of the promoter and transcription terminator from the gene encoding the β subunit of the seed storage protein phaseolin from the bean *Phaseolus vulgaris* (Doyle et al. (1986) *J. Biol. Chem.* 261:9228–9238) can be used for expression of the instant branched-chain amino acid biosynthetic enzymes in transformed soybean. The phaseolin cassette includes about 500 nucleotides upstream (5') from the translation initiation codon and about 1650 nucleotides downstream (3') from the translation stop codon of phaseolin. Between the 5' and 3' regions are the unique restriction endonuclease sites Nco I (which includes the ATG translation initiation codon), Sma I, Kpn I and Xba I. The entire cassette is flanked by Hind III sites.

The cDNA fragment of this gene may be generated by polymerase chain reaction (PCR) of the cDNA clone using appropriate oligonucleotide primers. Cloning sites can be incorporated into the oligonucleotides to provide proper orientation of the DNA fragment when inserted into the expression vector. Amplification is then performed as described above, and the isolated fragment is inserted into a pUC18 vector carrying the seed expression cassette.

Soybean embryos may then be transformed with the expression vector comprising sequences encoding a branched-chain amino acid biosynthetic enzyme. To induce somatic embryos, cotyledons, 3–5 mm in length dissected from surface sterilized, immature seeds of the soybean cultivar A2872, can be cultured in the light or dark at 26° C. on an appropriate agar medium for 6–10 weeks. Somatic embryos which produce secondary embryos are then excised and placed into a suitable liquid medium. After repeated selection for clusters of somatic embryos which multiplied as early, globular staged embryos, the suspensions are maintained as described below.

Soybean embryogenic suspension cultures can maintained in 35 mL liquid media on a rotary shaker, 150 rpm, at 26° C. with florescent lights on a 16:8 hour day/night schedule. Cultures are subcultured every two weeks by inoculating approximately 35 mg of tissue into 35 mL of liquid medium.

Soybean embryogenic suspension cultures may then be transformed by the method of particle gun bombardment (Kline et al. (1987) *Nature* (London) 327:70, U.S. Pat. No. 4,945,050). A Du Pont Biolistic™ PDS1000/HE instrument (helium retrofit) can be used for these transformations.

A selectable marker gene which can be used to facilitate soybean transformation is a chimeric gene composed of the 35S promoter from Cauliflower Mosaic Virus (Odell et al. (1985) *Nature* 313:810–812), the hygromycin phosphotransferase gene from plasmid pJR225 (from *E. coli* ; Gritz et al.(1983) *Gene* 25:179–188) and the 3' region of the nopaline synthase gene from the T-DNA of the Ti plasmid of *Agrobacterium tumefaciens*. The seed expression cassette comprising the phaseolin 5' region, the fragment encoding the branched-chain amino acid enzyme and the phaseolin 3' region can be isolated as a restriction fragment. This fragment can then be inserted into a unique restriction site of the vector carrying the marker gene.

To 50 μL of a 60 mg/mL 1 μm gold particle suspension is added (in order): 5 μL DNA (1 μg/μL), 20 μl spermidine (0.1 M), and 50 μL CaCl$_2$ (2.5 M). The particle preparation is then agitated for three minutes, spun in a microfuge for 10 seconds and the supernatant removed. The DNA-coated particles are then washed once in 400 μL 70% ethanol and resuspended in 40 μL of anhydrous ethanol. The DNA/particle suspension can be sonicated three times for one second each. Five μL of the DNA-coated gold particles are then loaded on each macro carrier disk.

Approximately 300–400 mg of a two-week-old suspension culture is placed in an empty 60×15 mm petri dish and the residual liquid removed from the tissue with a pipette. For each transformation experiment, approximately 5–10 plates of tissue are normally bombarded. Membrane rupture pressure is set at 1100 psi and the chamber is evacuated to a vacuum of 28 inches mercury. The tissue is placed approximately 3.5 inches away from the retaining screen and bombarded three times. Following bombardment, the tissue can be divided in half and placed back into liquid and cultured as described above.

Five to seven days post bombardment, the liquid media may be exchanged with fresh media, and eleven to twelve days post bombardment with fresh media containing 50 mg/mL hygromycin. This selective media can be refreshed weekly. Seven to eight weeks post bombardment, green, transformed tissue may be observed growing from untransformed, necrotic embryogenic clusters. Isolated green tissue is removed and inoculated into individual flasks to generate new, clonally propagated, transformed embryogenic suspension cultures. Each new line may be treated as an independent transformation event. These suspensions can then be subcultured and maintained as clusters of immature embryos or regenerated into whole plants by maturation and germination of individual somatic embryos.

Example 9

Expression of Chimeric Genes in Microbial Cells

The cDNAs encoding the instant branched-chain amino acid biosynthetic enzyme can be inserted into the T7 *E. coli* expression vector pBT430. This vector is a derivative of pET-3a (Rosenberg et al. (1987) *Gene* 56:125–135) which employs the bacteriophage T7 RNA polymerase/T7 promoter system. Plasmid pBT430 was constructed by first destroying the EcoR I and Hind III sites in pET-3a at their original positions. An oligonucleotide adaptor containing EcoR I and Hind III sites was inserted at the BamH I site of pET-3a. This created pET-3aM with additional unique cloning sites for insertion of genes into the expression vector. Then, the Nde I site at the position of translation initiation was converted to an Nco I site using oligonucleotide-directed mutagenesis. The DNA sequence of pET-3aM in this region, 5'-CATATGG, was converted to 5'-CCCATGG in pBT430.

Plasmid DNA containing a cDNA may be appropriately digested to release a nucleic acid fragment encoding the protein. This fragment may then be purified on a 1% NuSieve GTG™ low melting agarose gel (FMC). Buffer and agarose contain 10 μg/ml ethidium bromide for visualization of the DNA fragment. The fragment can then be purified from the agarose gel by digestion with GELase™ (Epicentre Technologies) according to the manufacturer's instructions, ethanol precipitated, dried and resuspended in 20 μL of water. Appropriate oligonucleotide adapters may be ligated to the fragment using T4 DNA ligase (New England Biolabs, Beverly, Mass.). The fragment containing the ligated adapters can be purified from the excess adapters using low melting agarose as described above. The vector pBT430 is digested, dephosphorylated with alkaline phosphatase (NEB) and deproteinized with phenol/chloroform as described above. The prepared vector pBT430 and fragment can then be ligated at 16° C. for 15 hours followed by transformation into DH5 electrocompetent cells (GIBCO BRL). Transformants can be selected on agar plates containing LB media and 100 μg/mL ampicillin. Transformants containing the gene encoding the branched-chain amino acid biosynthetic enzyme are then screened for the correct orientation with respect to the T7 promoter by restriction enzyme analysis.

For high level expression, a plasmid clone with the cDNA insert in the correct orientation relative to the T7 promoter can be transformed into *E. coli* strain BL21 (DE3) (Studier et al. (1986) *J. Mol. Biol.* 189:113–130). Cultures are grown in LB medium containing ampicillin (100 mg/L) at 25° C. At an optical density at 600 nm of approximately 1, IPTG (isopropylthio-β-galactoside, the inducer) can be added to a final concentration of 0.4 mM and incubation can be continued for 3 h at 25°. Cells are then harvested by centrifugation and re-suspended in 50 μL of 50 mM Tris-HCl at pH 8.0 containing 0.1 mM DTT and 0.2 mM phenyl methylsulfonyl fluoride. A small amount of 1 mm glass beads can be added and the mixture sonicated 3 times for about 5 seconds each time with a microprobe sonicator. The mixture is centrifuged and the protein concentration of the supernatant determined. One μg of protein from the soluble fraction of the culture can be separated by SDS-polyacrylamide gel electrophoresis. Gels can be observed for protein bands migrating at the expected molecular weight.

Example 10

Evaluating Compounds for Their Ability to Inhibit the Activity of a Plant Branched Chain Amino Acid Biosynthetic Enzyme The branched-chain amino acid biosynthetic enzymes described herein may be produced using any number of methods known to those skilled in the art. Such methods include, but are not limited to, expression in bacteria as described in Example 9, or expression in eukaryotic cell culture, in planta, and using viral expression systems in suitably infected organisms or cell lines. The instant branched-chain amino acid biosynthetic enzymes may be expressed either as mature forms of the proteins as observed in vivo or as fusion proteins by covalent attachment to a variety of enzymes, proteins or affinity tags. Common fusion protein partners include glutathione S-transferase ("GST"), thioredoxin ("Trx"), maltose binding protein, and C- and/or N-terminal hexahistidine polypeptide ("(His)$_6$"). The fusion proteins may be engineered with a protease recognition site at the fusion point so that fusion partners can be separated by protease digestion to yield intact mature enzyme. Examples of such proteases include thrombin, enterokinase and factor Xa. However, any protease can be used which specifically cleaves the peptide connecting the fusion protein and the enzyme.

Purification of the instant branched-chain amino acid biosynthetic enzyme, if desired, may utilize any number of separation technologies familiar to those skilled in the art of protein purification. Examples of such methods include, but are not limited to, homogenization, filtration, centrifugation, heat denaturation, ammonium sulfate precipitation, desalting, pH precipitation, ion exchange chromatography, hydrophobic interaction chromatography and affinity chromatography, wherein the affinity ligand represents a substrate, substrate analog or inhibitor. When the branched-chain amino acid biosynthetic enzymes are expressed as fusion proteins, the purification protocol may include the use of an affinity resin which is specific for the fusion protein tag attached to the expressed enzyme or an affinity resin containing ligands which are specific for the enzyme. For example, a branched-chain amino acid biosynthetic enzyme may be expressed as a fusion protein coupled to the C-terminus of thioredoxin. In addition, a (His)$_6$ peptide may be engineered into the N-terminus of the fused thioredoxin moiety to afford additional opportunities for affinity purification. Other suitable affinity resins could be synthesized by linking the appropriate ligands to any suitable resin such as Sepharose-4B. In an alternate embodiment, a thioredoxin fusion protein may be eluted using dithiothreitol; however, elution may be accomplished using other reagents which interact to displace the thioredoxin from the resin. These reagents include β-mercaptoethanol or other reduced thiol. The eluted fusion protein may be subjected to further purification by traditional means as stated above, if desired. Proteolytic cleavage of the thioredoxin fusion protein and the enzyme may be accomplished after the fusion protein is purified or while the protein is still bound to the ThioBond™ affinity resin or other resin.

Crude, partially purified or purified enzyme, either alone or as a fusion protein, may be utilized in assays for the evaluation of compounds for their ability to inhibit enzymatic activation of the branched-chain amino acid biosynthetic enzymes disclosed herein. Assays may be conducted under well known experimental conditions which permit optimal enzymatic activity. Examples of assays for these enzymes can be found in *Methods in Enzymology* (1970) Vol. XVII, Part A, (Tabor and Tabor eds.) Academic Press, New York. Assays for branched-chain amino acid transferase are presented by Jenkins et al., pp 802–807, Aki et al., pp 807–811, and Aki et al., pp 811–814 of the above volume. An assay for dihyroxyacid dehydratase is presented by Kiritani et al., pp 755–764. Assays for isopropylmalate dehydratase (which is refered to as isopropylmalate isomerase) are presented by Gross, pp 786–790, and by Cho-Chung et al., pp 782–785.

What is claimed is:

1. An isolated polynucleotide comprising a nucleotide sequence that encodes a dihydroxyacid dehydratase polypeptide, wherein said nucleotide sequence has a sequence identity of at least 80% based on the Clustal method of alignment when compared to a polynucleotide selected from the group consisting of SEQ ID NOs:1, 3, and 5.

2. The polynucleotide of claim 1 wherein the sequence identity is at least 85%.

3. The polynucleotide of claim 1 wherein the sequence identity is at least 90%.

4. The polynucleotide of claim 1 wherein the sequence identity is at least 95%.

5. The polynucleotide of claim 1 wherein the polynucleotide encodes a polypeptide selected from the group consisting of SEQ ID NOs:2, 4, and 6.

6. The polynucleotide of claim 1, wherein the polynucleotide comprises a nucleotide sequence selected from the group consisting of SEQ ID NO:1, 3, and 5.

7. An isolated complement of the polynucleotide of claim 1, wherein (a) the complement and the polynucleotide consist of the same number of nucleotides, and (b) the nucleotide sequences of the complement and the polynucleotide have 100% complementarity.

8. A recombinant DNA construct comprising the polynucleotide of claim 1 operably linked to at least one suitable regulatory sequence.

9. A cell comprising the polynucleotide of claim 1.

10. The cell of claim 9, wherein the cell is selected from the group consisting of a yeast cell, a bacterial cell and a plant cell.

11. A virus comprising the polynucleotide of claim 1.

12. A transgenic plant comprising the polynucleotide of claim 1.

* * * * *